United States Patent
Pan et al.

(10) Patent No.: US 10,804,470 B2
(45) Date of Patent: Oct. 13, 2020

(54) ORGANIC COMPOUND

(71) Applicant: GUANGZHOU CHINARAY OPTOELECTRONIC MATERIALS LTD., Guangzhou, Guangdong (CN)

(72) Inventors: Junyou Pan, Guangdong (CN); Hong Huang, Guangdong (CN)

(73) Assignee: GUANGZHOU CHINARAY OPTOELECTRONIC MATERIALS LTD, Guangdong (CN)

( * ) Notice: Subject to any disclaimer, the term of this patent is extended or adjusted under 35 U.S.C. 154(b) by 0 days.

(21) Appl. No.: 16/463,355

(22) PCT Filed: Nov. 23, 2017

(86) PCT No.: PCT/CN2017/112709
§ 371 (c)(1),
(2) Date: May 22, 2019

(87) PCT Pub. No.: WO2018/095388
PCT Pub. Date: May 31, 2018

(65) Prior Publication Data
US 2019/0355909 A1   Nov. 21, 2019

(30) Foreign Application Priority Data

Nov. 23, 2016 (CN) .......................... 2016 1 1046912

(51) Int. Cl.
*H01L 51/00* (2006.01)
*H01L 51/50* (2006.01)

(52) U.S. Cl.
CPC ...... *H01L 51/0058* (2013.01); *H01L 51/0054* (2013.01); *H01L 51/0072* (2013.01); *H01L 51/5016* (2013.01); *H01L 51/5056* (2013.01); *H01L 51/5072* (2013.01); *H01L 51/5092* (2013.01)

(58) Field of Classification Search
CPC ............. H01L 51/0058; H01L 51/0072; H01L 51/0054; H01L 51/5092; H01L 51/5072; H01L 51/5056; H01L 51/5016; H01L 51/0052; H01L 51/5012; C09K 11/06; C07D 247/00; C07D 221/06; C07C 15/38; C07C 15/24; C07C 15/20
See application file for complete search history.

(56) References Cited

U.S. PATENT DOCUMENTS

| | | | |
|---|---|---|---|
| 6,824,895 B1 | 11/2004 | Sowinski et al. | |
| 6,830,828 B2 | 12/2004 | Thompson et al. | |
| 6,835,469 B2 | 12/2004 | Kwong et al. | |
| 7,029,766 B2 | 4/2006 | Huo et al. | |
| 2001/0053462 A1 | 12/2001 | Mishima | |
| 2005/0025874 A1 | 2/2005 | Carlson | |
| 2007/0087219 A1 | 4/2007 | Ren et al. | |
| 2007/0252517 A1 | 11/2007 | Owczarczyk et al. | |
| 2008/0027220 A1 | 1/2008 | Stossel et al. | |
| 2009/0061681 A1 | 3/2009 | McMunigal et al. | |
| 2009/0134784 A1 | 5/2009 | Lin et al. | |
| 2012/0004407 A1 | 1/2012 | Stoessel et al. | |
| 2012/0217869 A1 | 8/2012 | Adachi et al. | |
| 2018/0312531 A1* | 11/2018 | Pan .......................... | C07F 7/12 |
| 2019/0334093 A1* | 10/2019 | Hu ...................... | H01L 51/5072 |

FOREIGN PATENT DOCUMENTS

| | | |
|---|---|---|
| CN | 102282150 A1 | 12/2011 |
| CN | 103483332 A1 | 1/2014 |
| CN | 103534331 | 6/2016 |
| CN | 106083606 | 11/2016 |
| EP | 1191613 B1 | 3/2006 |
| EP | 1191614 B1 | 5/2009 |
| EP | 1191612 B1 | 9/2009 |
| JP | 2009221442 | 10/2009 |
| KR | 20120110234 | 10/2012 |
| TW | 201305696 A1 | 3/2013 |
| TW | 201309778 A1 | 3/2013 |
| TW | 2013133359 A1 | 9/2013 |
| TW | 2013154064 A1 | 10/2013 |
| TW | 201343874 A1 | 11/2013 |
| TW | 201350558 A1 | 12/2013 |

(Continued)

OTHER PUBLICATIONS

PCT/CN2017/112709, "International Search Report", dated Feb. 14, 2018, 2 pages.
Kenichi Goushi et al., Organic light-emitting diodes employing efficient reverse intersystem crossing for triplet-to-singlet state conversion, Nature Photonics, 2012, p. 253-258.
Hiroki Uoyama, Kenichi Goushi, Katsuyuki Shizu, Hiroko Nomura, et.al., Highly efficient organic light-emitting diodes from delayed fluorescence, Nature, 492, 2012, 234.
Ed. George R. Newkome, Charles N. Moorefied, Fritz Vogtle, Dendrimers and Dendrons, Wiley-VCH Verlag GmbH & Co. KGaA, 2002, p. 1-21, 51-76, 76-102, 102-118, 191-234, 234-282, 282-309, 331-365, 366-393, 395-431, 431-455.
M. A. Baldo, M. E. Thompson, S. R. Forrest, High-efficiency fluorescent organic light-emitting devices using a phosphorescent sensitizer, Nature 403, (2000), 750-753.

(Continued)

*Primary Examiner* — Ahmed N Sefer
(74) *Attorney, Agent, or Firm* — Kilpatrick Townsend & Stockton LLP

(57) ABSTRACT

An organic compound, applications thereof, an organic mixture, and an organic electronic device. The structure of the organic compound is represented by formula (1), and definitions of substituent groups in the formula (1) are the same as those in the specifications.

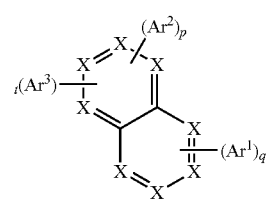

(1)

12 Claims, No Drawings

(56) References Cited

FOREIGN PATENT DOCUMENTS

| WO | 200070655 A2 | 11/2000 |
|---|---|---|
| WO | 2009146770 A2 | 12/2000 |
| WO | 200141512 A1 | 6/2001 |
| WO | 200202714 A2 | 1/2002 |
| WO | 200215645 A1 | 2/2002 |
| WO | 2005019373 A2 | 3/2005 |
| WO | 2005033244 A1 | 4/2005 |
| WO | 2007095118 A2 | 8/2007 |
| WO | 2009118067 A1 | 10/2009 |
| WO | 2010015307 A1 | 2/2010 |
| WO | 2010031485 A1 | 3/2010 |
| WO | 2010054728 A1 | 5/2010 |
| WO | 2010054731 A1 | 5/2010 |
| WO | 2010086089 A1 | 8/2010 |
| WO | 2010099852 A1 | 9/2010 |
| WO | 2010102709 A1 | 9/2010 |
| WO | 2010135519 A1 | 11/2010 |
| WO | 2011110277 A1 | 9/2011 |
| WO | 2011157339 A1 | 12/2011 |
| WO | 2012001086 A1 | 1/2012 |
| WO | 2012004407 A1 | 1/2012 |
| WO | 2012007087 A1 | 1/2012 |
| WO | 2012007088 A1 | 1/2012 |

OTHER PUBLICATIONS

Chihaya Adachi, Marc A. Baldo, Stephen R. Forrest, et. al., High-efficiency red electrophosphorescence devices, Appl. Phys. Lett.78 (2001), 1622-1624.
Junji Kido, Hiromichi Hayase, Kenichi Hongawa, et. al., Bright red lightemitting organic electroluminescent devices having a europium complex as an emitter, Appl. Phys. Lett.65 (1994), 2124.
Junji Kido, Katsutoshi Nagai, Yutaka Ohashi, Electroluminescence in a Terbium Complex,Chem. Lett. 657, 1990.
Curtis E. Johnson, Richard Eisenberg, Ted R. Evans, et. al., Luminescent Iridium(I), Rhodium(I), and Platinum(II) Dithiolate Complexes, JACS 105, 1983, 1795.
Mark Wrighton, David L. Morse, The Nature of the Lowest Excited State in Tricarbonylchloro-1, 10-phenanthrolinerhenium(I) and Related Complexes, JACS 96, 1974, 998.
Vuguang Ma, Houyu Zhang, Jiacong Shen, et al., Electroluminescence from triplet metal-ligand change-transfer exceited state of transition metal complexes, Synth. Metals 94, 1998, 245.
Ayataka Endo, Mai Ogasawara, Atsushi Takahashi, et. al., Thermally Activated Delayed Fluorescence from Sn4+-Porphyrin Complexes and Their Application to Organic Light-Emitting Diodes—a Novel Mechanism for Electroluminescence, Adv. Mater., 21, 2009, 4802.
Ayataka Endo, Keigo Sato, Kazuaki Yoshimura, et. al., Efficient up-conversion of triplet excitons into a singlet state and its application for organic light emitting diodes, Appl. Phys. Lett., 2011, 083302, 98.
Sae Youn Lee, Takuma Yasuda, Hiroko Nomura, High-efficiency organic light-emitting diodes utilizing thermally activated delayed fluorescence from triazine-based donor-acceptor hybrid molecules, Appl. Phys. Lett., 2012, 093306, 101.
Hiroyuki Tanaka, Katsuyuki Shizu, Hiroshi Miyazaki, Efficient green thermally activated delayed fluorescence (TADF) from a phenoxazine-triphenyltriazine (PXZ-TRZ) derivativew, Chem. Commun., 2012, 11392,48.
Kenichi Goushi, Kou Yoshida, Keigo Sato et al., Organic light-emitting diodes employing efficient reverse intersystem crossing for triplet-to-singlet state conversion, Nature Photonics, 6, 2012, 253.
Qisheng Zhang, Jie Li, Katsuyuki Shizu, et.al., Design of Efficient Thermally Activated Delayed Fluorescence Materials for Pure Blue Organic Light Emitting Diodes, J. Am. Chem. Soc, 2012, 14706, 134.
Gabor Mehes, Hiroko Nomura, Qisheng Zhang, et.al., Enhanced Electroluminescence Efficiency in a Spiro-Acridine Derivative through Thermally Activated Delayed Fluorescence, Angew. Chem. Int. Ed. 2012, 11311, 51.
Tetsuya Nakagawa,a Sung-Yu Ku,b Ken-Teung Wong, et.al., Electroluminescence based on thermally activated delayed fluorescence generated by a spirobifluorene donor-acceptor structure, Chem. Commun., 2012, 9580, 48.
Keiro Nasu,a Tetsuya Nakagativa,a Hiroko Nomura, et.al., A highly luminescent spiro-anthracenone-based organic light-emitting diode exhibiting thermally activated delayed fluorescence, Chem. Commun., 2013, 10385, 49.
Jie Li, Tetsuya Nakagawa, Qisheng Zhang, et.al.,Highly Effi cient Organic Light-Emitting Diode Based on a Hidden Thermally Activated Delayed Fluorescence Channel in a Heptazine Derivative, Adv. Mater., 2013, 3319, 25.
Fernando B. Dias, Konstantinos N. Bourdakos, Vygintas Jankus, et al., Triplet Harvesting with 100% Effi ciency by Way of Thermally Activated Delayed Fluorescence in Charge Transfer OLED Emitters, Adv. Mater., 2013, 3707, 25.
Takeshi Komino, Hiroko Nomura, Takahiro Koyanagi, et.al., Suppression of Efficiency Roll-Off Characteristics in Thermally Activated Delayed Fluorescence Based Organic Light-EmittingDiodes Using Randomly Oriented Host Molecules, Chem. Mater., 2013; 3038, 25.
Hiroyuki Tanaka, Katsuyuki Shizu, Hajime Nakanotani, et.al., Twisted Intramolecular Charge Transfer State for Long-Wavelength Thermally Activated Delayed Fluorescence, Chem. Mater., 2013, 3766, 25.
Jiyoung Lee, Katsuyuki Shizu, Hiroyuki Tanaka, et.al., Oxadiazole- and triazole-based highly-efficient thermally activated delayed fluorescence emitters for organic light-emitting diodes, J. Mater. Chem. C., 2013, 4599, 1.
Ryoichi Ishimatsu, Shigeyuki Matsunami, Katsuyuki Shizu, et.al., Solvent Effect on Thermally Activated Delayed Fluorescence by 1,2,3,5-Tetrakis(carbazol-9-yl)-4.6-dicyanobenzene, J. Phys. Chem. A., 2013, 5607, 117.
Helmut Kipphan, Handbook of Print Media : Technologies and Production Methods, (2004), 40-67, 117-144, 711-730.
V. Bulovic, G. Gu, P. E. Burrows, et. al., Transparent light-emitting devices, Nature, 1996, 380, p. 29.
G. Gu, V. Bulovic, P. E. Burrows, et. al., Transparent organic light emitting device, Appl. Phys. Lett. 1996, 68, p. 2605.

\* cited by examiner

ORGANIC COMPOUND

The present disclosure is a national stage for International Application PCT/CN2017/112709, filed on Nov. 23, 2017, which claims priority to Chinese Patent Application No. 201611046912.8 filed on Nov. 23, 2016, and entitled "THERMALLY ACTIVATED DELAYED FLUORESCENCE MATERIALS AND APPLICATIONS THEREOF", the entire content of which is incorporated by reference herein in its entirety.

TECHNICAL FIELD

The present disclosure relates to the technical field of organic optoelectronic materials, and in particular to an organic compound and an application thereof, a mixture and an organic electronic device.

BACKGROUND

Organic light-emitting diodes (OLEDs) show great potentials in the applications of optoelectronic devices (such as flat-panel display and lighting) due to the synthetic diversities, relatively low manufacturing costs, and excellent optical and electrical properties of organic semiconductive materials.

In order to improve the emitting efficiency of the organic light-emitting diodes, various light-emitting materials based on fluorescent and phosphorescent materials have been developed. The organic light-emitting diodes based on fluorescent materials have high reliability, but their internal electroluminescence quantum efficiency is limited to 25% under electric field excitation, since the probability ratio of the exciton generating a singlet excited state to a triplet excited state is 1:3. In contrast, organic light-emitting diodes based on phosphorescent materials have achieved an internal luminescence quantum efficiency of around 100%. However, phosphorescent OLED has a significant problem of the Roll-off effect, that is, luminous efficiency decreases rapidly as the current or brightness increases, which is particularly unfavorable for high-brightness applications.

In general, the commercialized phosphorescent materials are iridium and platinum complexes. Such raw materials are rare and expensive, while the synthesis of complex is complicated, resulting in high costs. In order to overcome problem of rare and expensive raw materials and complicated synthesis of iridium and platinum complexes, Adachi proposed a concept of reverse intersystem crossing so that organic compounds can be used instead of metal complexes to achieve high efficiency comparable with phosphorescent OLEDs. This concept has been achieved through various combinations of materials, such as: 1) using exciplex, see Adachi et al., Nature Photonics, Vol. 6, p 253 (2012); 2) using thermally activated delayed fluorescence (TADF) materials, see Adachi et al., Nature, Vol. 492, 234, (2012). However, most organic compounds with TADF used the form of donor groups connected with electron-deficient or electron-accepting groups, resulting in the complete separation of the electron cloud distributions of the highest occupied molecular orbital (HOMO) from that of the lowest unoccupied molecular orbit (LUMO), which reduces the difference ($\Delta E_{ST}$) between the singlet state ($S_1$) and the triplet state ($T_1$) of organic compounds. The red and green TADF materials have been developed and achieved certain progress in many aspects of performance. However, the device has a low light-emitting efficiency due to the separation of the electron cloud of HOMO from that of LUMO, especially, the performance of blue TADF light-emitting materials still has a gap compared with the phosphorescent light-emitting materials.

SUMMARY

According to various embodiments of the present application, an organic compound, an application thereof, an organic mixture, and an organic electronic device are provided, solving one or more problems involved in background.

An organic compound for an organic electronic device has a structure represented by a general formula (1):

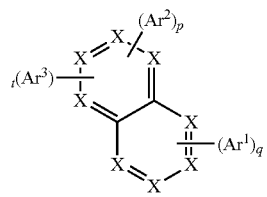

wherein, $Ar^1$, $Ar^2$ and $Ar^3$ are independently selected from fused aromatic rings containing more than 6 ring atoms or fused heteroaromatic rings containing more than 6 ring atoms;

p is selected from 0, 1, 2 or 3, q is selected from 0, 1, 2, 3 or 4, t is selected from 0, 1, 2, 3, 4 or 5; and p+t+q≥3;

X is selected from N or $CR^1$, and adjacent Xs are not N simultaneously;

$R^1$ is one or more groups selected from the group consisting of H, D, a linear alkyl group containing 1 to 20 C atoms, an linear alkoxy group containing 1 to 20 C atoms, a linear thioalkoxy group containing 1 to 20 C atoms, a branched or cyclic alkyl group containing 3 to 20 C atoms, a branched or cyclic alkoxy group containing 3 to 20 C atoms, a branched or cyclic thioalkoxy group containing 3 to 20 C atoms, a silyl group, a substituted ketone group containing 1 to 20 C atoms, an alkoxycarbonyl group containing 2 to 20 C atoms, an aryloxycarbonyl group containing 7 to 20 C atoms, a cyano group, a carbamoyl group, a haloformyl group, a formyl group, an isocyano group, an isocyanate group, a thiocyanate group, an isothiocyanate group, a hydroxyl group, a nitro group, a $CF_3$ group, Cl, Br, F, a crosslinkable group, a substituted or unsubstituted aromatic ring system containing 5 to 40 ring atoms or substituted or unsubstituted heteroaromatic ring system containing 5 to 40 ring atoms, and an aryloxy group containing 5 to 40 ring atoms or heteroaryloxy group containing 5 to 40 ring atoms; and $R^1$ forms a monocyclic or polycyclic aliphatic or aromatic ring with a ring bonded to the group, or a plurality of $R^1$s form a monocyclic or polycyclic aliphatic or aromatic ring with each other.

An application of the organic compound described above in an organic electronic device is further provided.

A polymer having at least one repeating unit comprising the organic compound described above is provided.

A mixture comprises at least one organic functional material and the organic compound described above, and the organic functional material is selected from the group consisting of a hole injection material, a hole transport material, a hole blocking material, an electron injection material, an electron transport material, an electron blocking material, an organic host material, or a light-emitting material.

A formulation comprises the organic compound described above or the polymer described above, and at least one organic solvent.

An organic electronic device comprises a functional layer, the functional layer comprising the organic compound described above or the polymer described above or the mixture described above, or being prepared from the formulation described above.

The details of one or more embodiments of the present disclosure are set forth in the accompanying drawings and the description below. Other features, objects and advantages of the present disclosure will become apparent from the description, the accompanying drawings, and claims.

DETAILED DESCRIPTION OF THE EMBODIMENTS

The objects, technical solution and advantages of the present application will become more clearly and understandable by further describing the present disclosure in detail with reference to the accompanying drawings and embodiments. It should be noted that, specific embodiments illustrated herein is merely for the purpose of explanation, and should not be deemed to limit the disclosure.

The formulation, the printing ink and the ink herein have the same meaning and may be used interchangeably. The main material, the matrix material, Host or Matrix material have the same meaning and may be used interchangeably. Metal organic clathrate, metal organic complex, and organometallic complex have the same meaning and may be used interchangeably.

An organic compound for an organic electronic device according to an embodiment has a structure represented by a general formula (1):

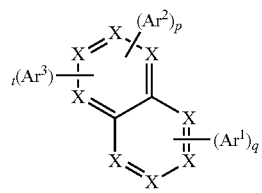

(1)

wherein, $Ar^1$, $Ar^2$ and $Ar^3$ are independently selected from fused aromatic rings containing more than 6 ring atoms or fused heteroaromatic rings containing more than 6 ring atoms;

p is selected from 0, 1, 2 or 3, q is selected from 0, 1, 2, 3 or 4, t is selected from 0, 1, 2, 3, 4 or 5; and p+t+q≥3;

X is selected from N or $CR^1$, and adjacent Xs are not N simultaneously;

$R^1$ is one or more groups selected from the group consisting of H, D, a linear alkyl group containing 1 to 20 C atoms, an linear alkoxy group containing 1 to 20 C atoms, a linear thioalkoxy group containing 1 to 20 C atoms, a branched or cyclic alkyl group containing 3 to 20 C atoms, a branched or cyclic alkoxy group containing 3 to 20 C atoms, a branched or cyclic thioalkoxy group containing 3 to 20 C atoms, a silyl group, a substituted ketone group containing 1 to 20 C atoms, an alkoxycarbonyl group containing 2 to 20 C atoms, an aryloxycarbonyl group containing 7 to 20 C atoms, a cyano group, a carbamoyl group, a haloformyl group, a formyl group, an isocyano group, an isocyanate group, a thiocyanate group, an isothiocyanate group, a hydroxyl group, a nitro group, a $CF_3$ group, Cl, Br, F, a crosslinkable group, a substituted or unsubstituted aromatic or heteroaromatic ring system containing 5 to 40 ring atoms, and an aryloxy or heteroaryloxy group containing 5 to 40 ring atoms; and $R^1$ forms a monocyclic or polycyclic aliphatic or aromatic ring with a ring bonded to the group, or a plurality of $R^1$s form a monocyclic or polycyclic aliphatic or aromatic ring with each other.

The above organic compound contains at least three or more fused aromatic or heteroaromatic rings in order to have a thermally-activated delayed fluorescence luminescence (TADF) properties. The organic compound can be used as a TADF luminescent material, which may have improved luminous efficiency and lifetime as an electroluminescent device by combining with a suitable host material, providing a solution for light emitting device with low cost, high efficiency, long life and low roll-off. Meanwhile, the organic compound can also be used as a blue fluorescent host material, and improve the efficiency and lifetime of the blue light-emitting device by combining with a suitable blue-light guest material, thereby providing a wider range of choices for blue light-emitting host materials.

It should be noted that $Ar^1$, $Ar^2$ or $Ar^3$ may have a substituent R in the ring, and R is selected from —H, —F, —Cl, Br, I, —D, —CN, —$NO_2$, —$CF_3$, $B(OR^3)_2$, $Si(R^3)_3$, linear alkanes, alkane ethers, alkane thioethers containing 1 to 10 carbon atoms, branched alkanes, and cycloalkanes.

In an embodiment, p is 1. In an embodiment, q is 1 or 2. In an embodiment, t is 1 or 2.

In another embodiment, p is selected from 1, 2 or 3, q is selected from 1, 2, 3 or 4, t is selected from 2, 3, 4 or 5; in still another embodiment, p is selected from 1, 2 or 3, q is selected from 1, 2, 3 or 4, t is selected from 3, 4 or 5.

In an embodiment, $Ar^1$, $Ar^2$, $Ar^3$ and $R^1$ are independently selected from naphthalene, and p is selected from 1, 2 or 3, q is selected from 1, 2, 3 or 4, and t is selected from 2, 3, 4 or 5.

In an embodiment, when X is bond to $Ar^1$, $Ar^2$, or $Ar^3$ at any position, respectively, X is CH.

In an embodiment, $Ar^1$, $Ar^2$, and $Ar^3$ are independently selected from fused aromatic rings containing more than 7 ring atoms or fused heteroaromatic rings containing more than 7 ring atoms. $Ar^1$, $Ar^2$ and $Ar^3$ in independent multiple occurrences may be the same or different.

In an embodiment, the fused aromatic ring contains 7 to 22 ring atoms or fused heteroaromatic ring contains 7 to 22 ring atoms. In an embodiment, the fused aromatic ring contains 7 to 20 ring atoms or fused heteroaromatic ring contains 7 to 20 ring atoms. Further, in an embodiment, the fused aromatic ring contains 7 to 18 ring atoms or fused heteroaromatic ring contains 7 to 18 ring atoms. The heteroatom is selected from Si, N, O, S, C(=O) or P. In an embodiment, the heteroatom is selected from N, O, or S.

The aromatic group refers to a hydrocarbyl group comprising at least one aromatic ring, and the fused aromatic ring system refers to a ring system including a monocyclic group or polycyclic ring system. The heteroaromatic group refers to a hydrocarbyl group (containing heteroatoms) comprising at least one heteroaromatic ring, and the fused heteroaromatic ring system refers to a ring system including a monocyclic group or a polycyclic ring system. Such polycyclic rings may have two or more rings, wherein two carbon atoms are shared by two adjacent rings, i.e., fused ring. At least one of such polycyclic rings is aromatic or heteroaromatic. Furthermore, in an embodiment, the aromatic or heteroaromatic ring systems not only include aromatic or heteroaromatic systems, but also a plurality of aryl or heteroaryl groups in the systems may be interrupted by short non-aromatic units (<10% of non-H atoms; the non-H atoms may be C, N or O atoms). In an embodiment, the plurality of aryl or heteroaryl groups in the systems may be interrupted by short non-aromatic units (<5% of non-H atoms). Therefore, systems such as 9,9'-spirobifluorene, 9,9-diarylfluorene, triarylamine, diaryl ether and the like are also considered to be aromatic ring systems for the purpose of this disclosure.

Specifically, examples of the fused aromatic ring include: naphthalene, anthracene, phenanthrene, perylene, tetracene, pyrene, benzopyrene, triphenylene, acenaphthene, fluorene, and derivatives thereof.

Specifically, examples of the suitable fused heteroaromatic ring system include: benzofuran, benzothiophene, indole, carbazole, pyrroloimidazole, pyrrolopyrrole, thienopyrrole, thienothiophene, furopyrrole, furofuran, thienofuran, benzisoxazole, benzisothiazole, benzimidazole, quinoline, isoquinoline, cinnoline, quinoxaline, phenanthridine, perimidine, quinazoline, quinazolinone and derivatives thereof.

In an embodiment, the organic compound is conjugated in a large proportion of structure. Further, the organic compound is completely conjugated in the entire molecular structure.

In an embodiment, X is selected from N or $CR^1$, wherein $R^1$ is selected from a substituted or unsubstituted aromatic ring system containing 5 to 40 ring atoms or substituted or unsubstituted heteroaromatic ring system containing 5 to 40 ring atoms.

In an embodiment, X is N or CH.

Further, in an embodiment, X is N.

In an embodiment, $R^1$ is selected from benzene, naphthalene, anthracene, phenanthrene, perylene, tetracene, pyrene, benzopyrene, triphenylene, acenaphthene, fluorene, and derivatives thereof, furan, benzofuran, thiophene, benzothiophene, pyrrole, pyrazole, triazole, imidazole, oxazole, oxadiazole, thiazole, tetrazole, indole, carbazole, pyrroloimidazole, pyrrolopyrrole, thienopyrrole, thienothiophene, furopyrrole, furofuran, thienofuran, benzisoxazole, benzisothiazole, benzimidazole, pyridine, pyrazine, pyridazine, pyrimidine, triazine, quinoline, isoquinoline, cinnoline, quinoxaline, phenanthridine, perimidine, quinazoline, quinazolinone, and derivatives thereof.

In an embodiment, $Ar^1$ to $Ar^3$ and $R^1$ are each selected from naphthalene and derivatives thereof.

In an embodiment, $Ar^1$ to $Ar^3$ and $R^1$ are each selected from naphthalene.

In an embodiment, all Xs are CH or C.

Further, in an embodiment, the organic compound is one selected from compounds represented by the following structural formulas (2) to (16):

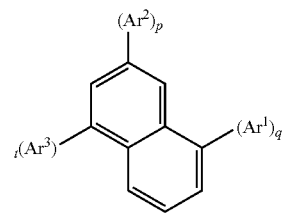

(2)

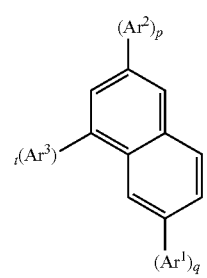

(3)

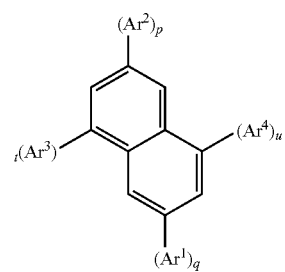

(4)

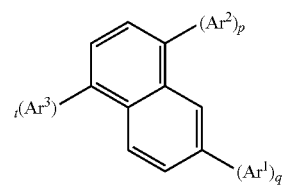

(5)

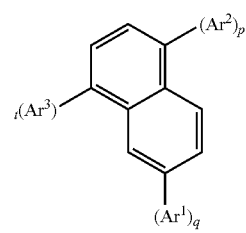

(6)

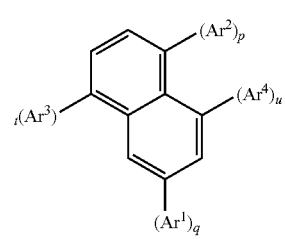

(7)

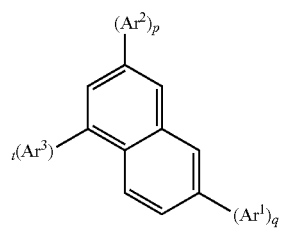

(8)

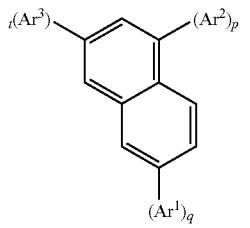

(9)

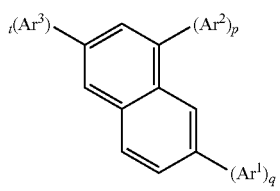

(10)

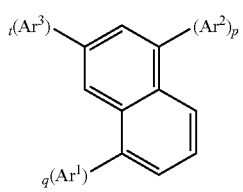

(11)

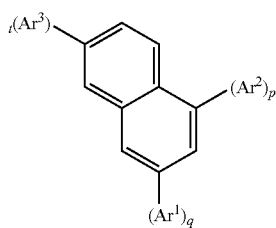

(12)

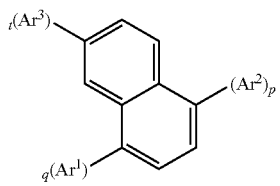

(13)

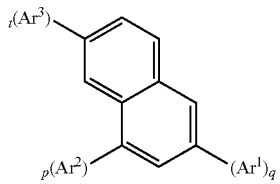

(14)

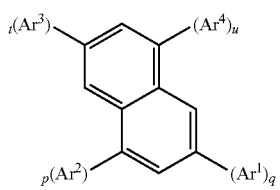

(15)

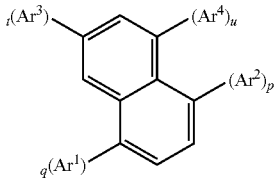

(16)

wherein $Ar^4$ is independently selected from fused aromatic rings containing more than 6 ring atoms or fused heteroaromatic rings containing more than 6 ring atoms; and u is selected from 0, 1, 2, 3, 4 or 5.

In an embodiment, p is selected from 1, 2 or 3, q is selected from 0,1, 2, 3 or 4, t is selected from 2, 3, 4 or 5, and u is selected from 1, 2, 3, 4 or 5 in formulas (8).

In still an embodiment, p is selected from 1, 2 or 3, q is selected from 0, 1, 2, 3 or 4, t is selected from 3, 4 or 5, and u is selected from 1, 2, 3, 4 or 5 in formulas (8).

In an embodiment, $Ar^1$, $Ar^2$, $Ar^3$ are independently selected from naphthalene and derivatives thereof, and p is selected from 1, 2 or 3, q is selected from 0, 1, 2, 3 or 4, and t is selected from 2, 3, 4 or 5, and u is selected from 1, 2, 3, 4 or 5 in formulas (8).

In an embodiment, $Ar^1$, $Ar^2$ or $Ar^3$ in multiple occurrences may be, independently one selected from the following structural groups or a combination thereof.

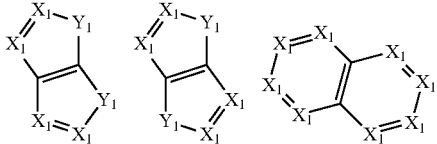

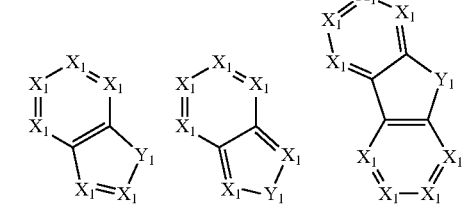

$X^1$ is selected from $CR^2$ or N;
$Y^1$ is selected from $NR^3$, C(=O), S or O;
$R^2$ and $R^3$ is one or more groups independently selected from the group consisting of H, D, a linear alkyl group containing 1 to 20 C atoms, an linear alkoxy group containing 1 to 20 C atoms, a linear thioalkoxy group containing 1 to 20 C atoms, a branched or cyclic alkyl group containing 3 to 20 C atoms, a branched or cyclic alkoxy group containing 3 to 20 C atoms, a branched or cyclic thioalkoxy group containing 3 to 20 C atoms, a branched or cyclic silyl group containing 3 to 20 C atoms, a substituted ketone group containing 1 to 20 C atoms, an alkoxycarbonyl group containing 2 to 20 C atoms, an aryloxycarbonyl group containing 7 to 20 C atoms, a cyano group, a carbamoyl group, a haloformyl group, a formyl group, an isocyano group, an isocyanate group, a thiocyanate group, an isothiocyanate group, a hydroxyl group, a nitro group, a $CF_3$ group, Cl, Br, F, a crosslinkable group, a substituted or unsubstituted aromatic ring system containing 5 to 40 ring atoms or substituted or unsubstituted heteroaromatic ring system containing 5 to 40 ring atoms, and an aryloxy group containing 5 to 40 ring atoms or heteroaryloxy group containing 5 to 40 ring atoms; and at least one of $R_2$ and $R_3$ forms a monocyclic or polycyclic aliphatic or aromatic ring with a ring bonded to the group, or $R_2$ and $R_3$ form a monocyclic or polycyclic aliphatic or aromatic ring with each other.

Further, in an embodiment, $Ar^1$, $Ar^2$ and $Ar^3$ are independently selected from any groups described above.

In an embodiment, $Ar^1$ to $Ar^3$ have any of the following structural formulas, which may be further substituted by one or more $R_a$ groups. $R_a$ is selected from the group consisting of H, D, a linear alkyl group containing 1 to 20 C atoms, a branched alkane containing 1 to 20 C atoms, and a heteroatom-containing alkane group containing 1 to 20 C atoms.

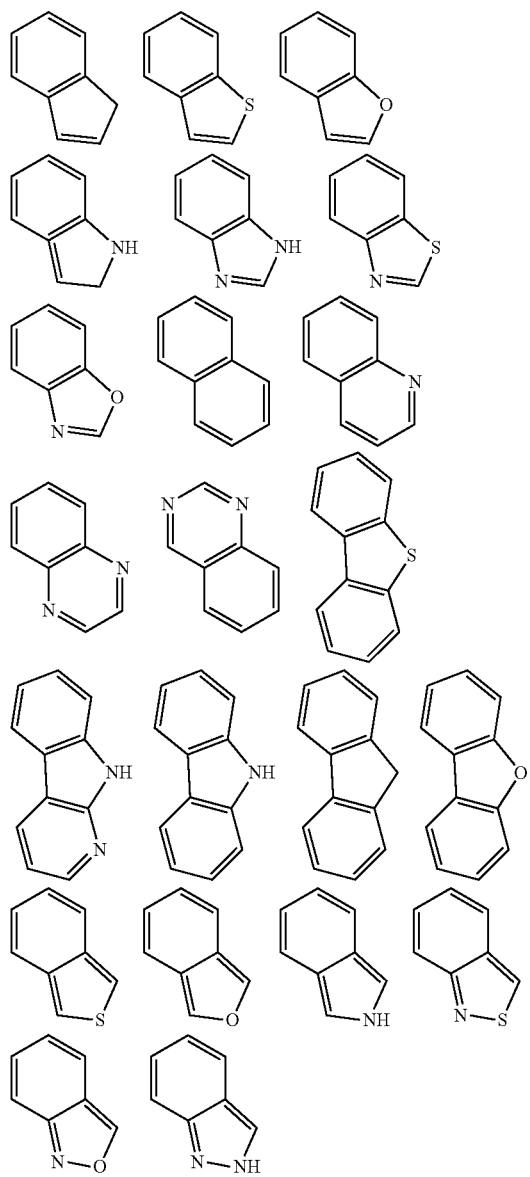

In an embodiment, $Ar^1$ to $Ar^3$ are independently selected from any of the above structural formulas. It should be noted that the definition of $Ar^1$ to $Ar^3$ in the above embodiments are also applicable to $R^1$.

In addition, other functional groups are sometimes introduced in $R^1$ for requirement for other properties of the organic materials, such as increased solubility, printability, or introduction of other electronic properties. In an embodiment, $R^1$ comprises a non-aromatic ring system.

For the purposes of the present disclosure, the non-aromatic ring system contains 1 to 10 carbon atoms in the ring system, and includes not only saturated but also partially unsaturated cyclic systems which may be unsubstituted or optionally substituted with one or more $R^1$ groups. $R^1$ may be the same or different in each occurrence. In an embodiment, the non-aromatic ring system contains 1 to 3 carbon atoms. In an embodiment, the non-aromatic ring system comprises may also comprise one or more heteroatoms, wherein the heteroatoms may be one or more groups selected from Si, N, P, O, S and Ge. In an embodiment, the heteroatoms are one or more groups selected from Si, N, P, O and S. Such non-aromatic ring system, for example, may be cyclohexyl-like or piperidine-like systems, and may also be cyclooctadiene-like ring systems. These terms are equally applicable to fused non-aromatic ring systems.

For the purposes of the present disclosure, the aromatic ring system or heteroaromatic ring system described above may be substituted by R group. In an embodiment, R is selected from (1) a C1 to C10 alkyl group, wherein the C1 to C10 alkyl group may refer to the following groups: methyl, ethyl, n-propyl, isopropyl, cyclopropyl, n-butyl, isobutyl, sec-butyl, t-butyl, cyclobutyl, 2-methylbutyl, n-hexyl, cyclohexyl, n-heptyl, cycloheptyl, n-octyl, cyclooctyl, 2-ethylhexyl, trifluoromethyl, pentafluoromethyl, 2,2,2-trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, or octynyl; (2) a C1 to C10 alkoxy group, wherein the C1 to C10 alkoxy group may be refer to methoxy, ethoxy, n-propoxy, isopropoxy, n-butoxy, isobutoxy, sec-butoxy, tert-butoxy or 2-methylbutoxy; (3) C2 to C10 aryl or heteroaryl, which may be monovalent or divalent depending on the application, and in each case can also be substituted by $R^4$ mentioned above and may be attached to an aromatic or heteroaromatic ring at any desired position. In an embodiment, the C2 to C10 aryl or heteroaryl group may be selected from the following groups: benzene, naphthalene, anthracene, dinaphthalene, dihydronaphthalene, chrysene, pyrene, fluoranthene, naphthacene, pentacene, benzopyrene, furan, benzofuran, isobenzofuran, dibenzofuran, thiophene, benzothiophene, isobenzothiophene, thiofluorene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenimidazole, pyridimidazole, pyrazine-imidazole, quinoxaline-imidazole, oxazole, benzoxazole, naphthoxazole, anthracenazole, phenoxazole, isoxazole, 1,2-thiazole, 1,3-thiazole, benzothiazole, pyridazine, benzopyridazine, pyrimidine, benzopyrimidine, quinoxaline, pyrazine, phenazine, 1,5-naphthyridine, carbazole, benzocholine, phenanthroline, 1,2,3-triazole, 1,2,4-triazole, benzotriazole, 1,2,3-oxadiazole, 1,2,4-oxadiazole, 1,2,5- oxadiazole, 1,3,4-oxadiazole, 1,2,3-thiadiazole, 1,2,4-thiadiazole, 1,2,5-thiadiazole, 1,3,4- thiadiazole, 1,3,5-triazine, 1,2,4-triazine, 1,2,3-triazine, tetrazole. 1,2,4,5-tetrazine, 1,2,3,4-tetrazine, 1,2,3,5-tetrazine, purine, pteridine, indolizine or benzothiadiazole. For the purposes of the present disclosure, aromatic and heteroaromatic ring systems are particularly considered to, in addition to the above-mentioned aryl and heteroaryl groups, also refer to Biphenylene, terphenylene, fluorene, spirofluorene, dihydrophenanthrene, tetrahydropyrene, and cis- or trans-indenofluorene.

In an embodiment, $R^1$ in multiple occurrences may identically or differently contain the following structural units or a combination thereof.
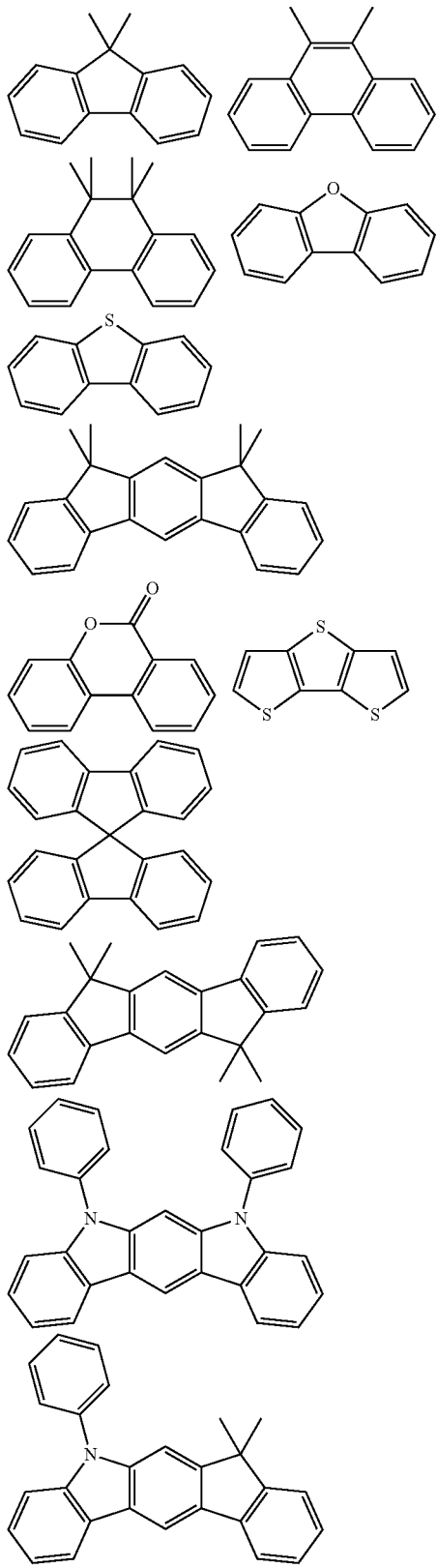
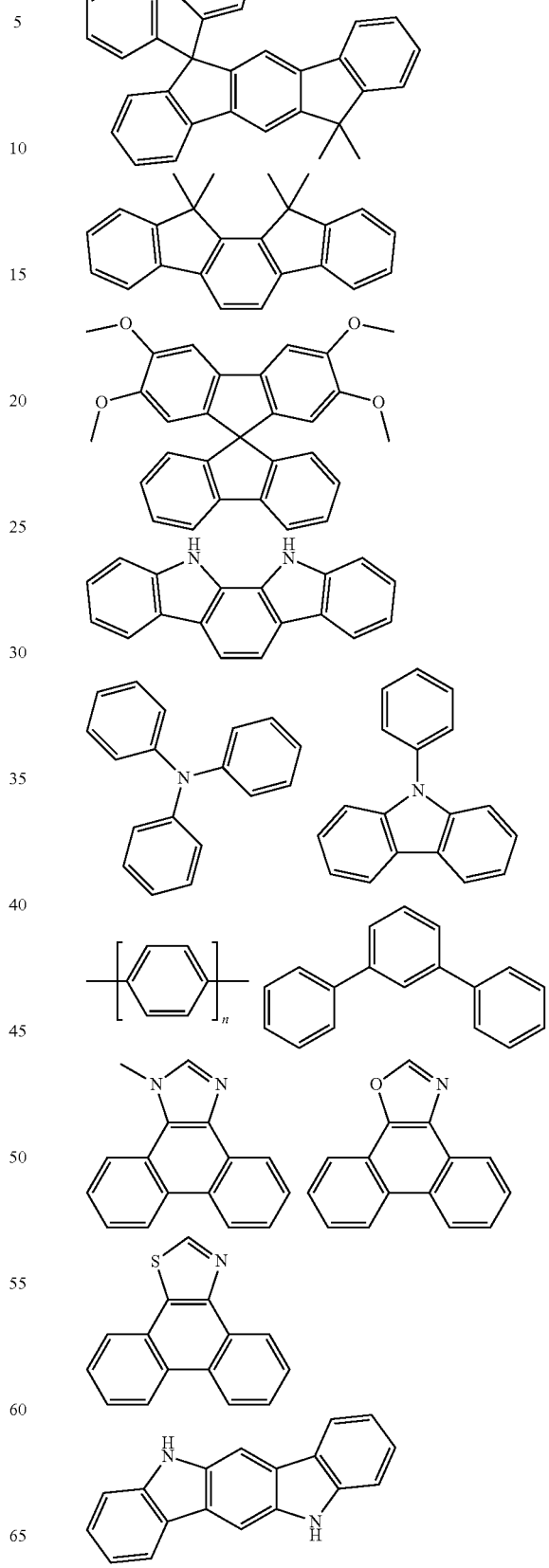

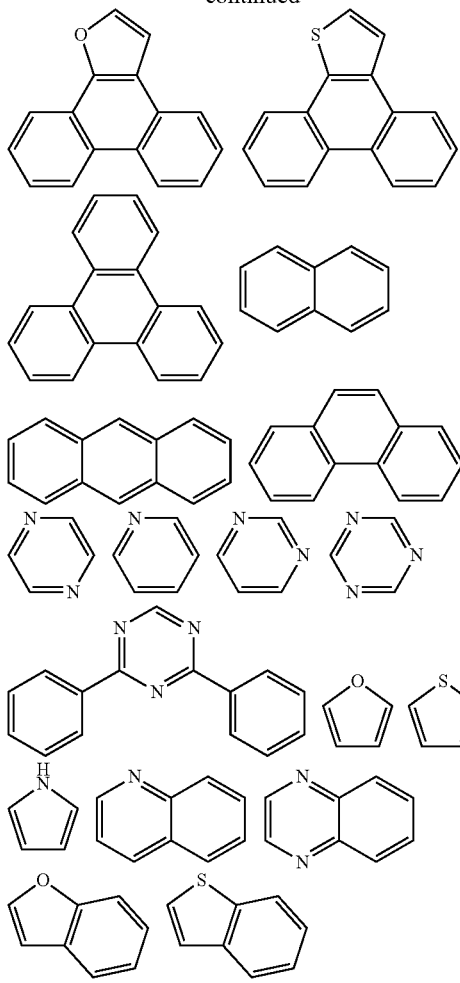

wherein n is selected from 1, 2, 3 or 4.

In an embodiment, $R^1$ is selected from any groups in the above table.

In addition, in order to obtain the thermally-activated delayed fluorescence TADF characteristics, according to the principle of thermally-activated delayed fluorescence TADF material (see Adachi et al., Nature Vol 492, 234, (2012)), the triplet exciton of the organic compound may be converted to singlet exciton via reverse internal conversion if the $\Delta E(S_1-T_1)$ of the organic compound is small enough, so as to achieve efficient light emitting. In general, the TADF material is derived from connecting an electron-donating group with an electron-deficient or electron-accepting group, i.e., having a distinct D-A structure.

In an embodiment, the organic compound has a $\Delta E(S_1-T_1) \leq 0.30$ eV. In another embodiment, the organic compound has a $\Delta E(S_1-T_1) \leq 0.25$ eV. In some embodiment, the organic compound has a $\Delta E(S_1-T_1) \leq 0.20$ eV. In still another embodiment, the organic compound has a $\Delta E(S_1-T_1) \leq 0.10$ eV.

In an embodiment, in multiple occurrences of $R^1$, at least one of $R^1$ comprises an electron-donating group, or at least one of $R^1$ comprises an electron-accepting group. In other embodiments, in multiple occurrences of $R^1$, at least one of $R^1$ comprises an electron-donating group and at least one of $R^1$ comprises an electron-accepting group.

In an embodiment, for the substituent group R of $Ar^1 \sim Ar^3$ in multiple occurrences, at least one of R comprises an electron-donating group, and/or at least one of R comprises an electron-accepting group. That is, in multiple occurrences of Ar, at least one of Ar comprises an electron-donating group, or at least one of Ar comprises an electron-accepting group, wherein Ar is $Ar^1$, $Ar^2$ or $Ar^3$. In other embodiments, in multiple occurrences of Ar, at least one of Ar comprises an electron-donating group, and at least one of Ar comprises an electron-accepting group.

In an embodiment the electron-donating group, comprises any of the following groups.

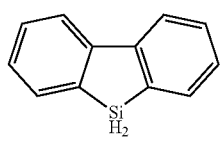

D1

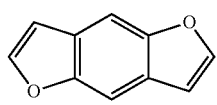

D2

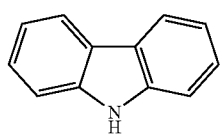

D3

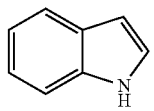

D4

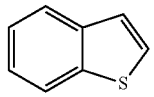

D5

D6

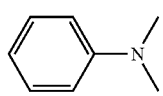

D7

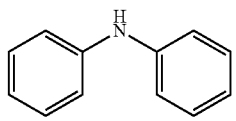

D8

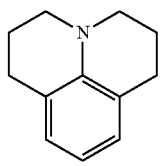

D9

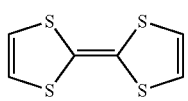

D10

It should be noted that the electron-donating group is selected from any groups in the above table.

In an embodiment, the electron-accepting group is selected from F, cyano or includes any of the following groups.

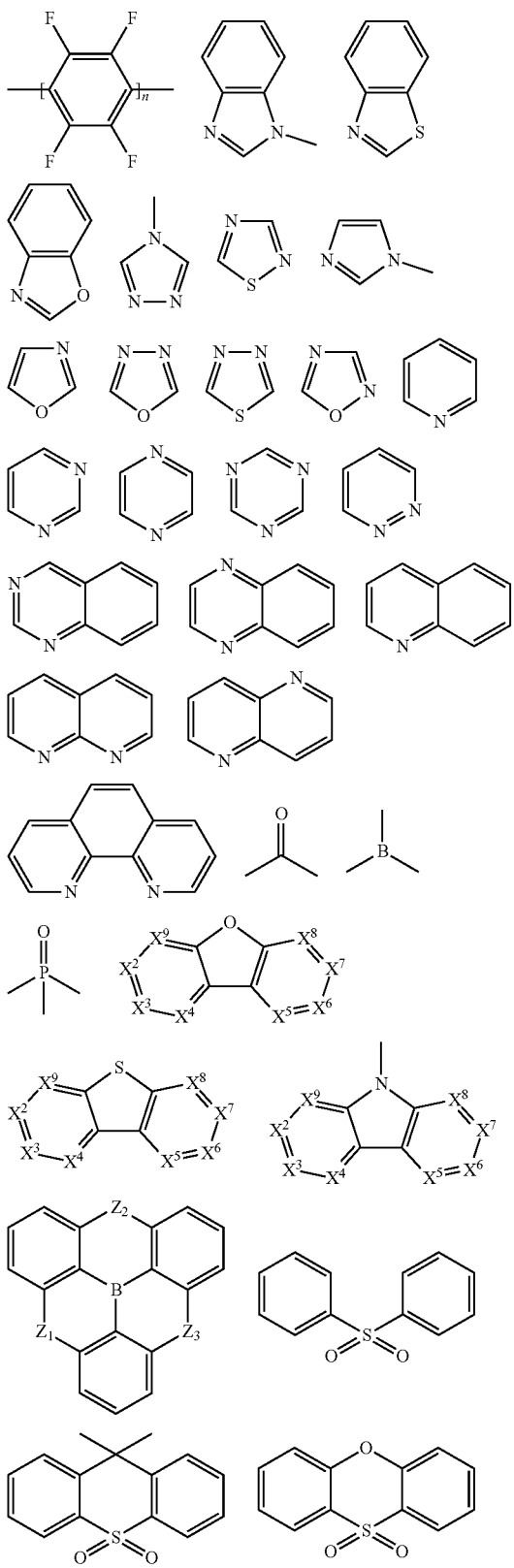

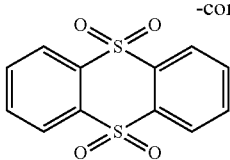

Wherein n is 1, 2 or 3; $X^2$ to $X^9$ are independently selected from $CR^8$ or N, and at least one of $X^1$ to $X^8$ is N; $Z_1$ to $Z_3$ are independently absent, or $Z_1$ to $Z_3$ are independently selected from N, O, S or C, and not all of $Z_1$ to $Z_3$ are absent; $R^8$ is selected from hydrogen, alkyl, alkoxy, amino, alkene, alkyne, aralkyl, heteroalkyl, aryl or heteroaryl. It should be noted the $Z_1$ to $Z_3$ being independently absent means that the two adjacent benzene rings are not connected by a bond.

Further, in an embodiment, the electron-accepting group is selected from any of the above groups.

The term "small molecule" as defined herein refers to a molecule that is not a polymer, oligomer, dendrimer, or blend. In particular, a small molecule has no repeating structures. The molecular weight of the small molecule is no greater than 4000 g/mole, further no greater than 3000 g/mole, and still further no greater than 2000 g/mole.

The term "polymer" as defined herein includes homopolymer, copolymer, and block copolymer. In addition, in the present disclosure, the polymer also includes dendrimer. The synthesis and application of dendrimers are described in Dendrimers and Dendrons, Wiley-VCH Verlag GmbH & Co. KGaA, 2002, Ed. George R. Newkome, Charles N. Moorefield, Fritz Vogtle.

The "conjugated polymer" is a polymer whose backbone is predominantly composed of the $sp^2$ hybrid orbital of carbon (C) atom. Some known examples are: polyacetylene and poly (phenylene vinylene), on the backbone of which the C atom can also be substituted by other non-C atoms, and which is still considered to be a conjugated polymer when the $sp^2$ hybridization on the backbone is interrupted by some natural defects. In addition, the conjugated polymer in the present disclosure may also comprise aryl amine, aryl phosphine and other heteroaromatics, organometallic complexes, and the like on the backbone.

In particular, the solubility of the small molecule organic compound is ensured by the substituents on the units of the formulas (1) to (16) and optionally on the benzene ring unit that is present. In addition, the large steric hindrance of $Ar^1$ to $Ar^4$ with naphthyl groups leads to poor molecular planarity, improving the solubility of small molecule organic compound. Other substituents may also improve solubility if these substituents are present.

Depending on the type of substitution, the structural units of the general formulas (1) to (16) are suitable for a wide variety of functions in small molecule organic compound. Therefore, they are particularly used as the main skeleton of the small molecule compound or as an emitter. In particular, the $Ar^1$~$Ar^4$ groups define compounds that are particularly suitable for certain functions. The $Ar^1$~$Ar^4$ groups have an influence on the electronic properties of the structural units of the general formulas (1) to (16).

In an embodiment, H in the organic compound is at least partially deuterated. In an embodiment, 10% of the H is deuterated. In another embodiment, 20% of the H is deuterated. In some embodiment, 30% of the H is deuterated. In still some embodiment, 40% of the H is deuterated.

In an embodiment, the organic compound is one selected from the compounds represented by the following structures. These structures can be substituted at all possible substitution positions.

(17)
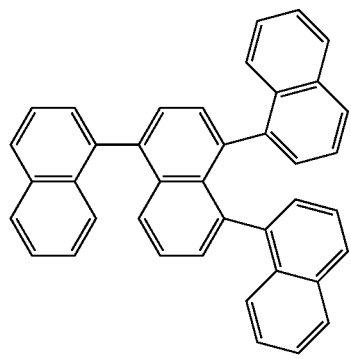
(18)
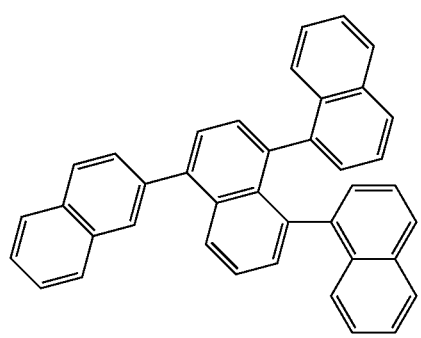
(19)
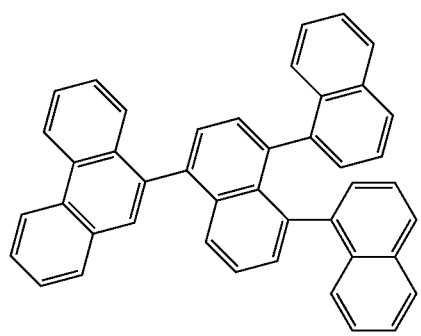
(20)
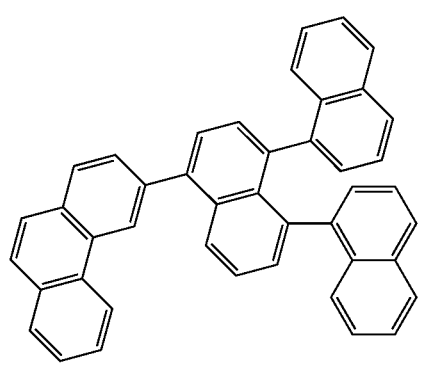
(21)
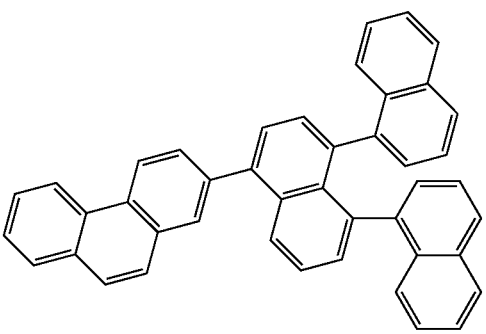
(22)
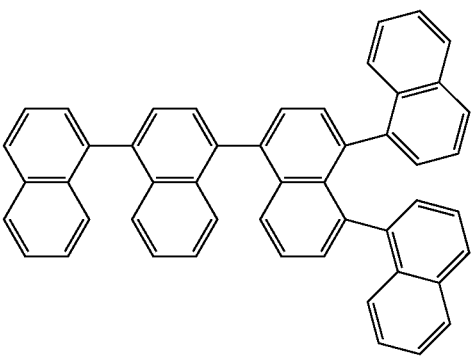
(23)
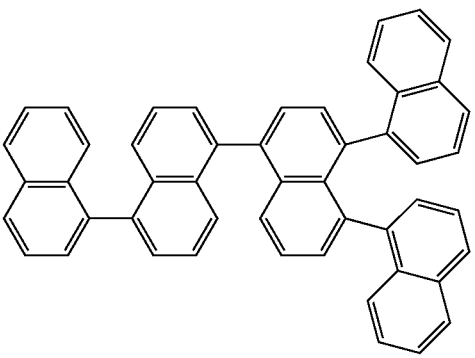
(24)
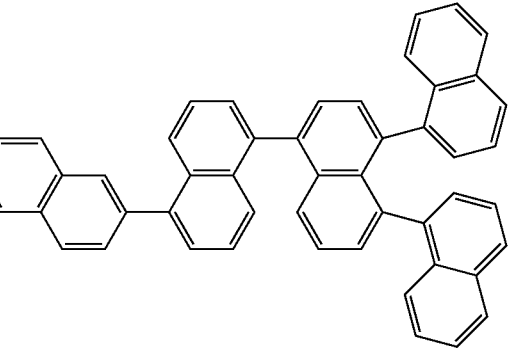

-continued
(25)
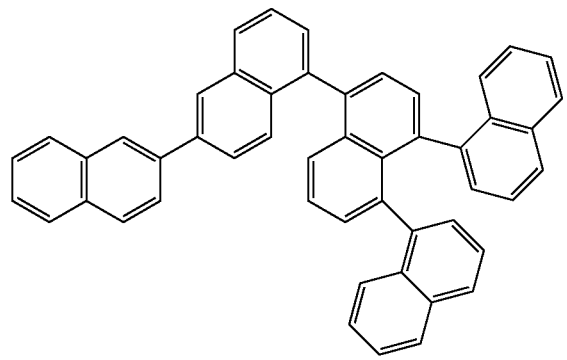
(26)
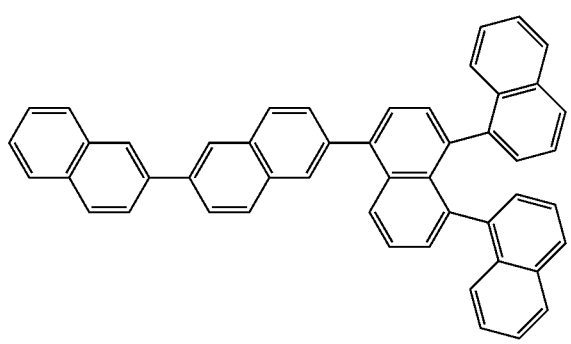
(27)
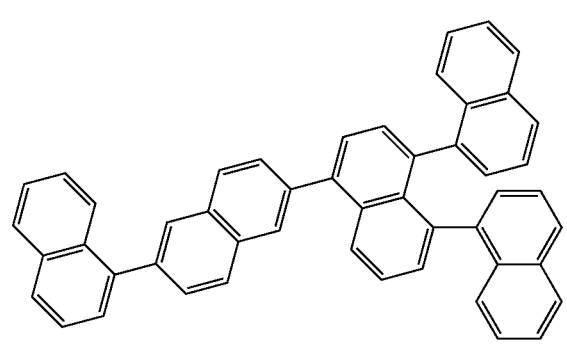
(28)
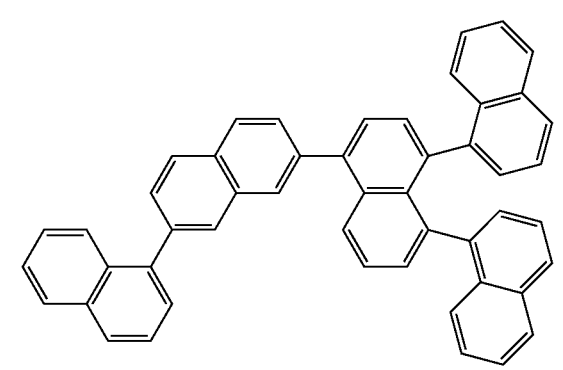
-continued
(29)
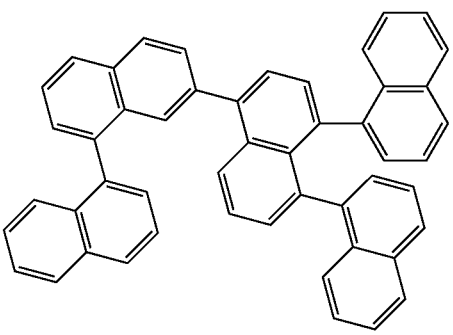
(30)
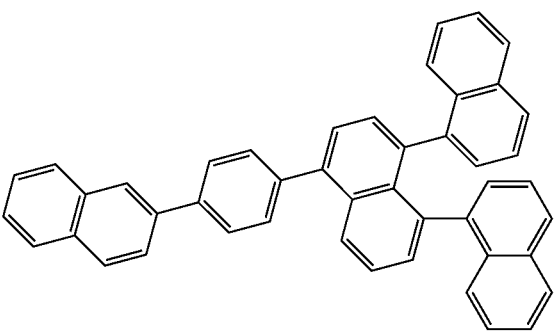
(31)
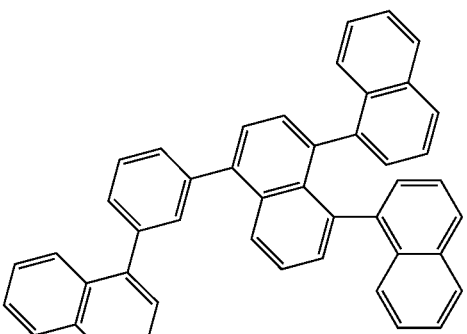
(32)
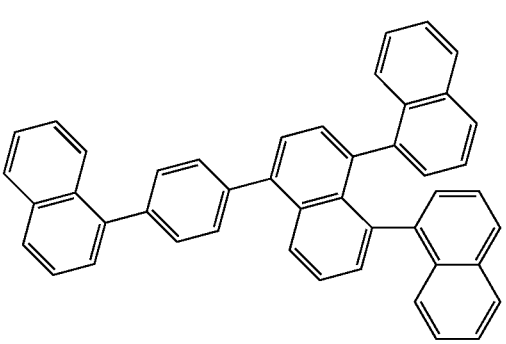

(33)
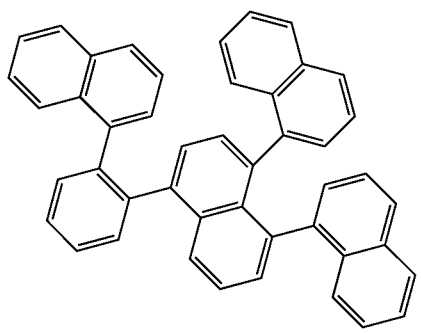
(37)
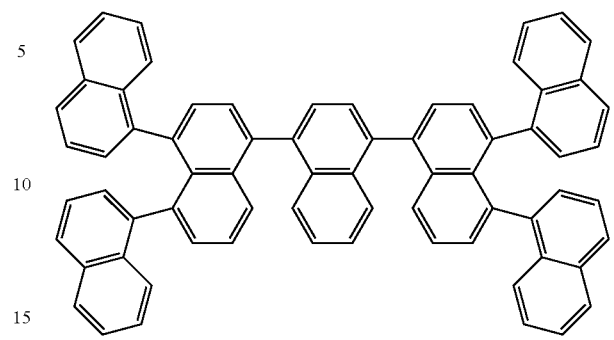
(34)
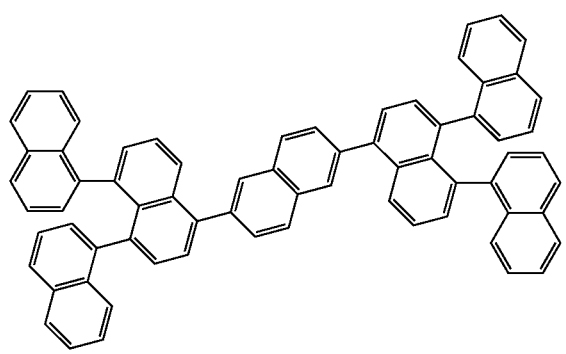
(38)
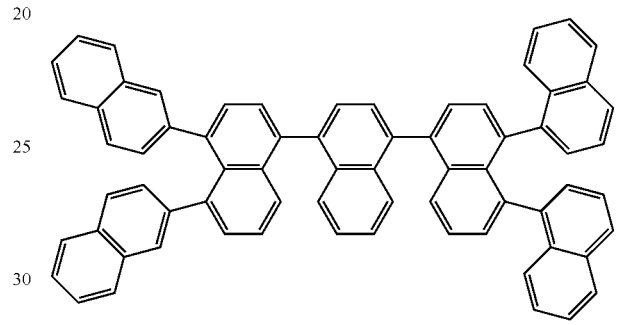
(35)
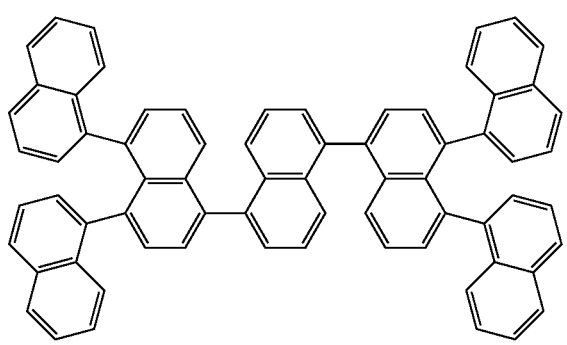
(39)
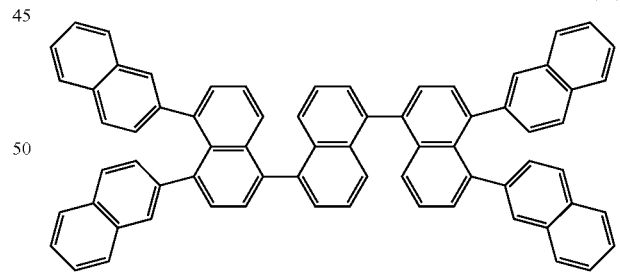
(40)
(36)
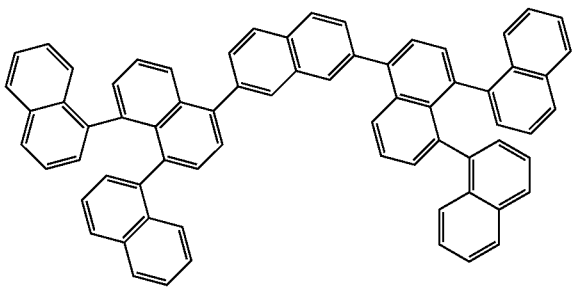
(41)
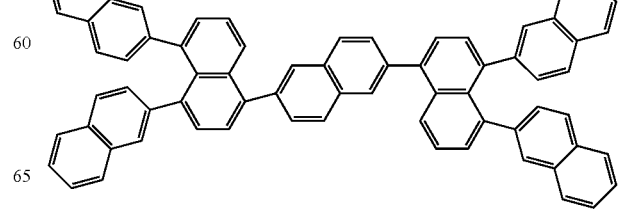

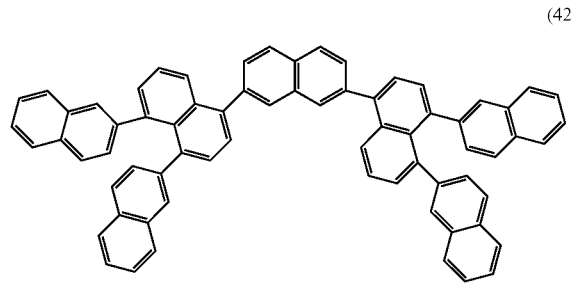
(42)
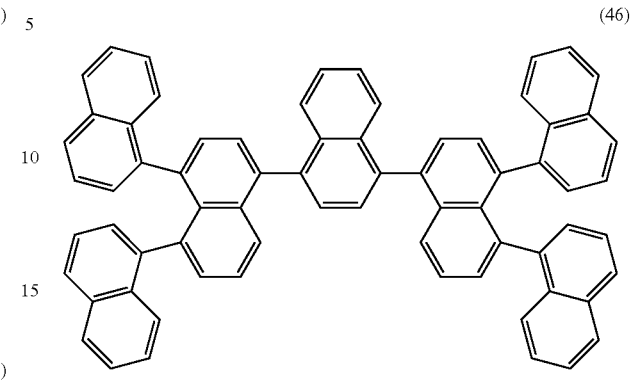
(46)
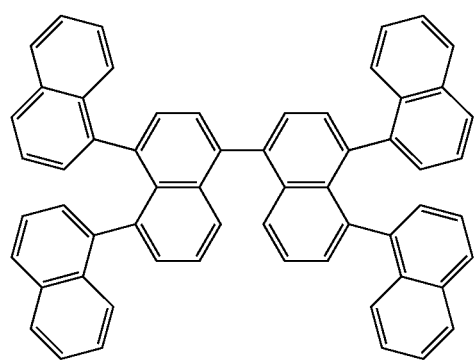
(43)
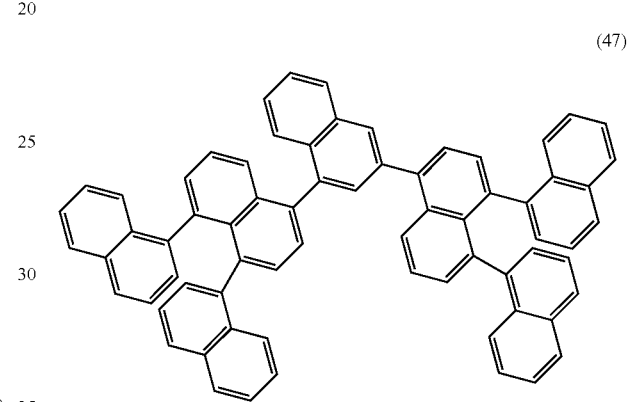
(47)
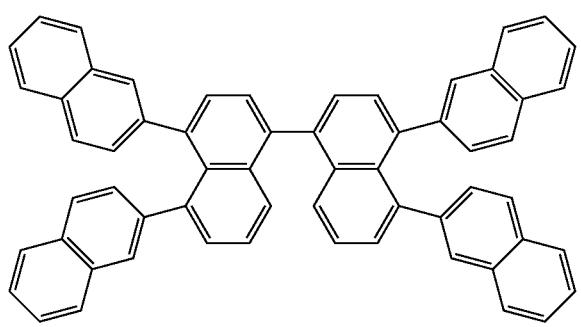
(44)
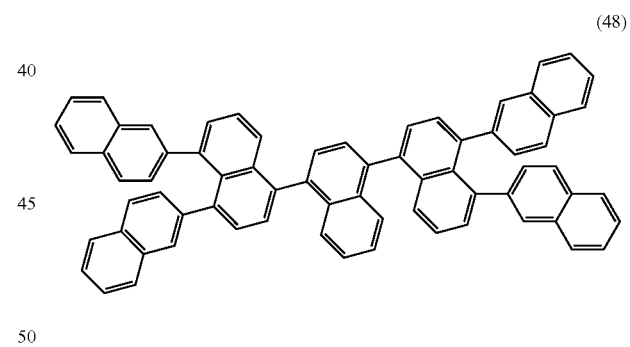
(48)
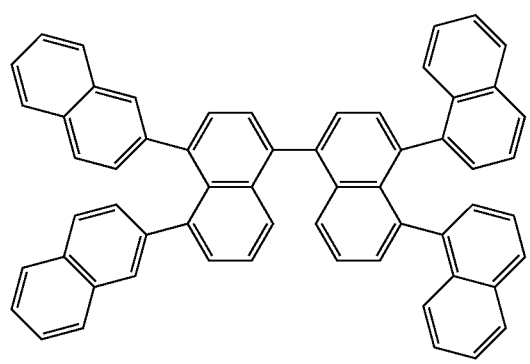
(45)
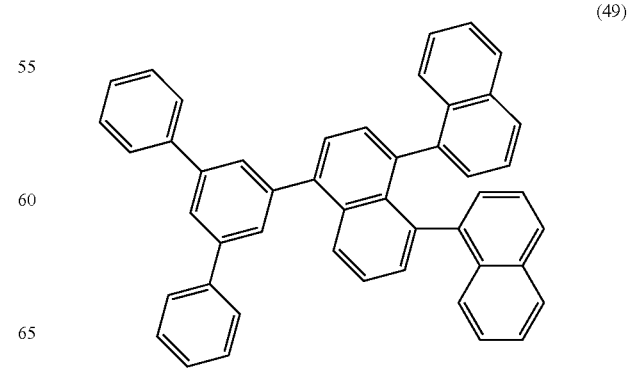
(49)

-continued
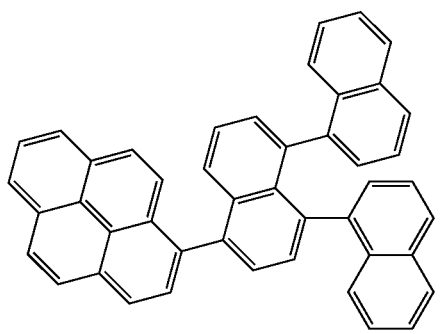
(50)
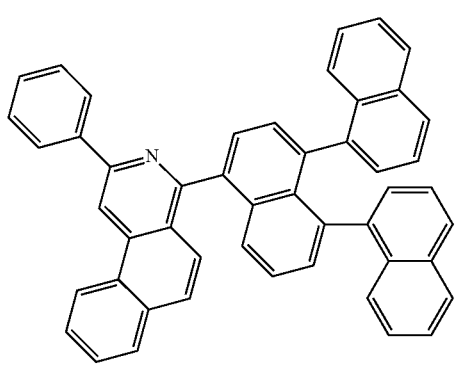
(51)
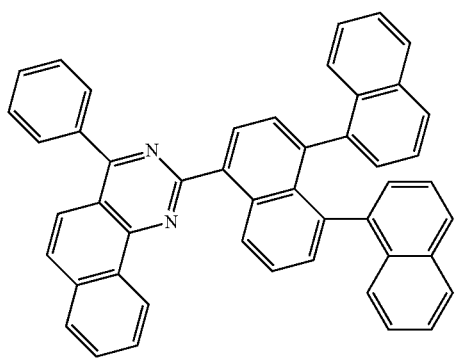
(52)
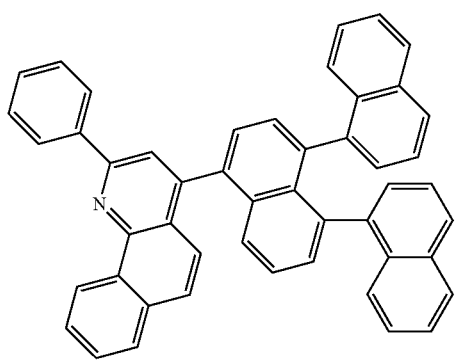
(53)
-continued
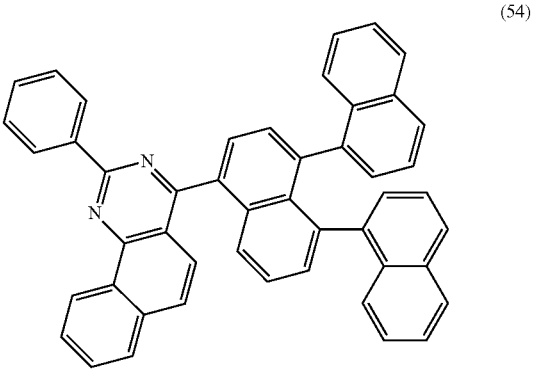
(54)
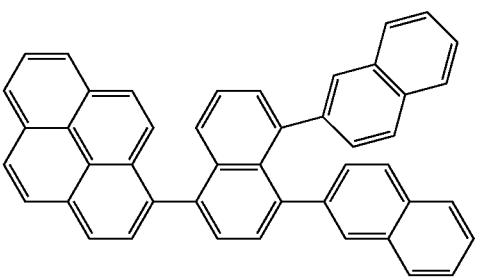
(55)
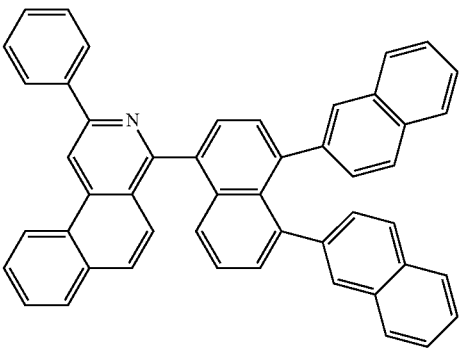
(56)
(57)

(58)
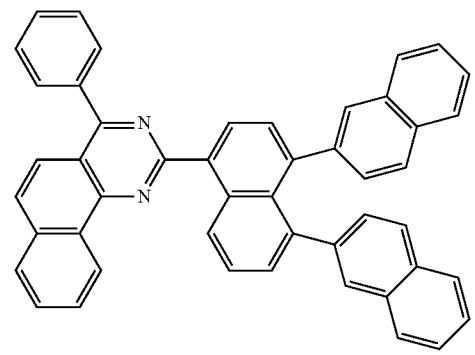
(59)
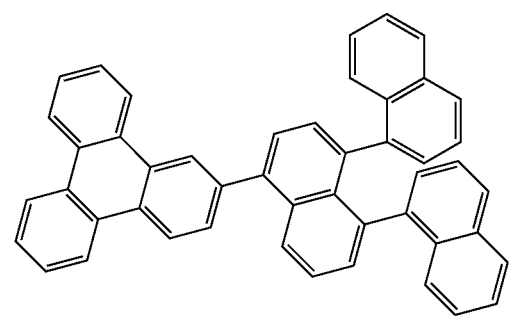
(60)
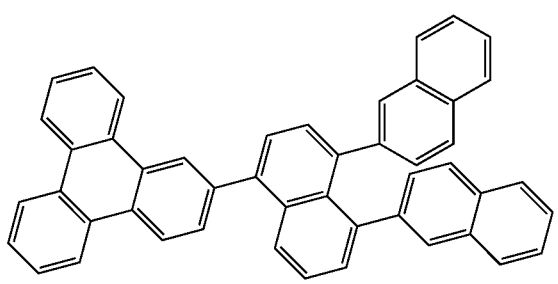
(61)
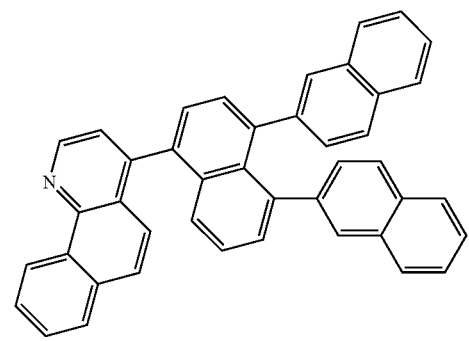
(62)
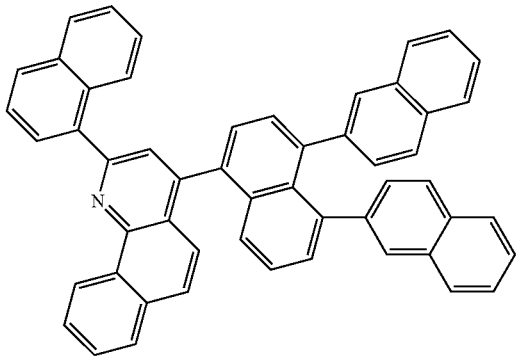
(63)
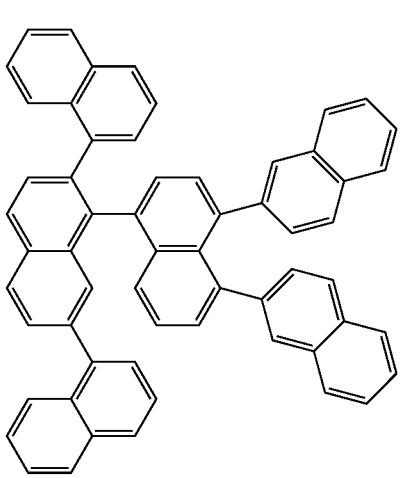
(64)
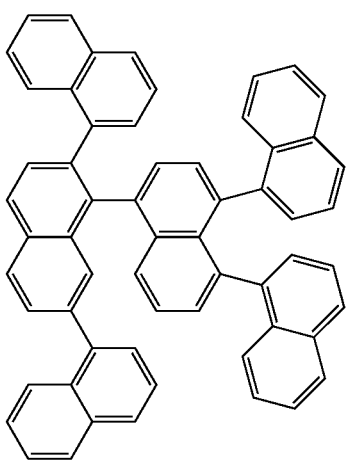

(65)
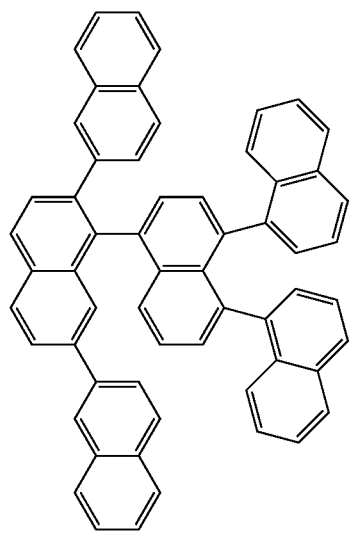
(68)
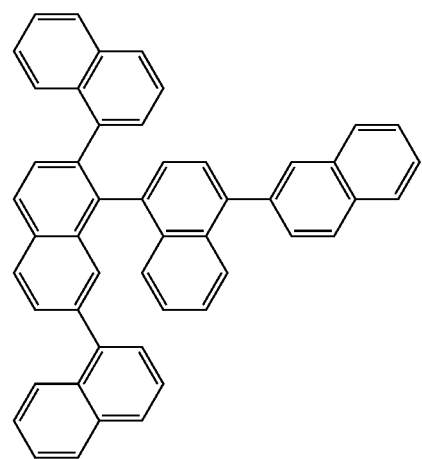
(66)
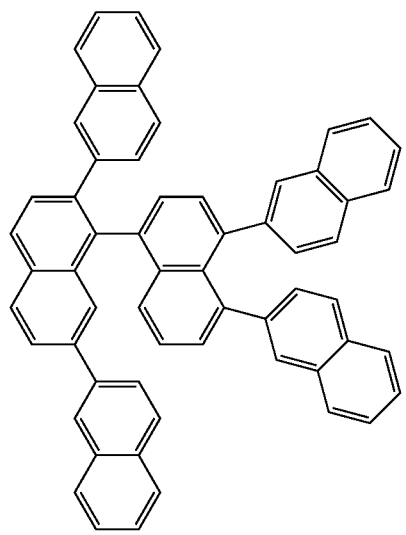
(69)
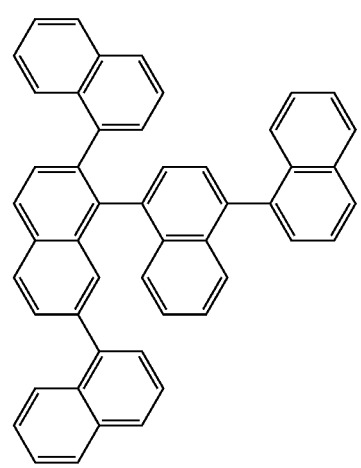
(67)
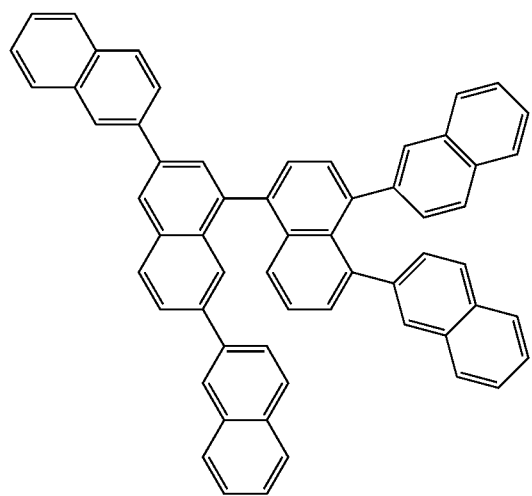
(70)
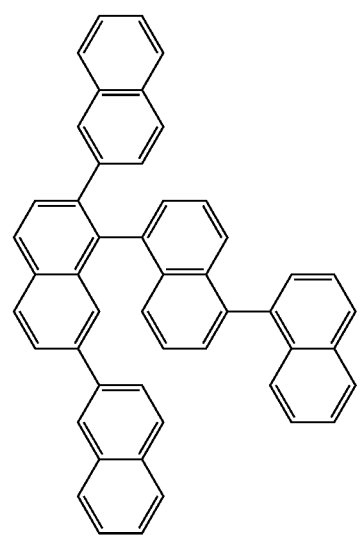

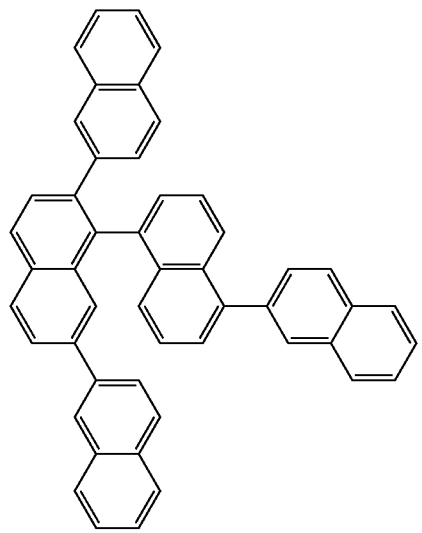
(71)
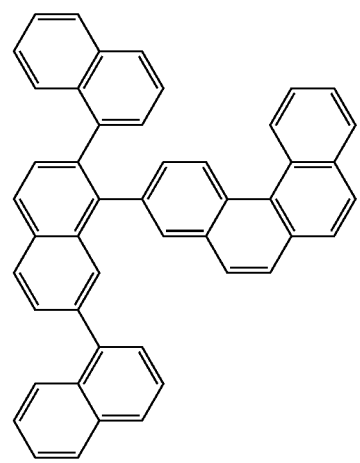
(74)
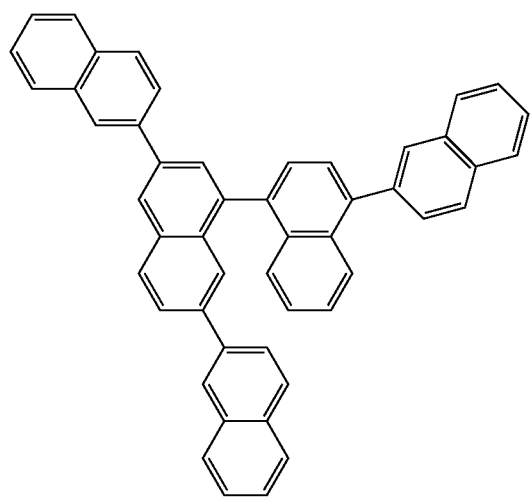
(72)
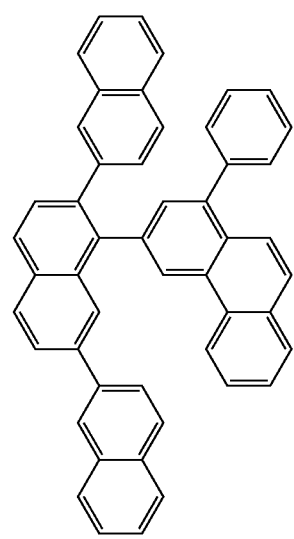
(75)
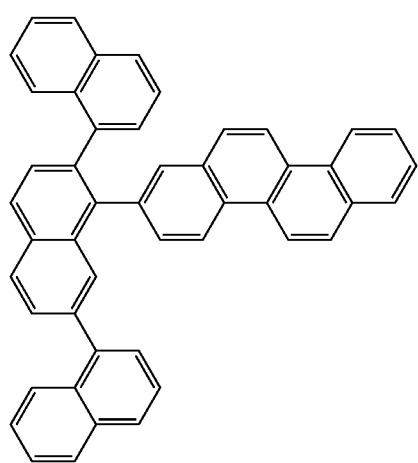
(73)
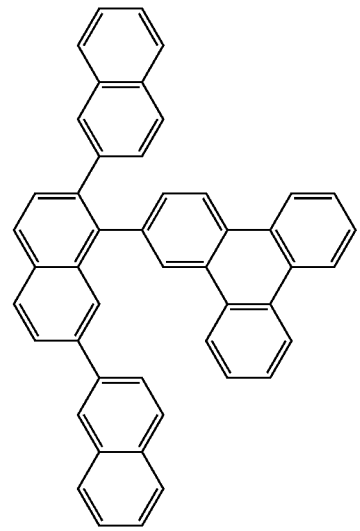
(76)

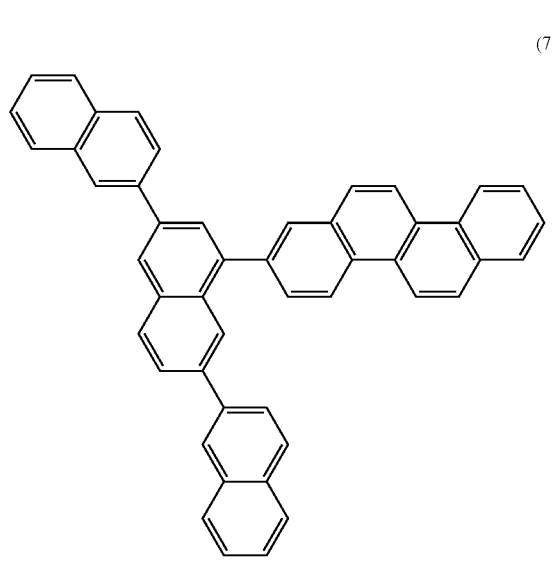
(77)
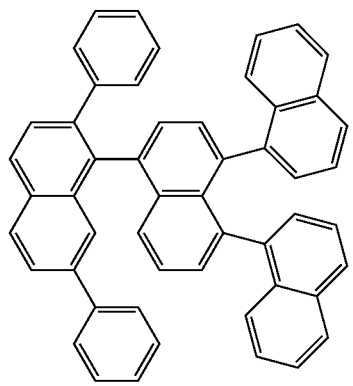
(80)
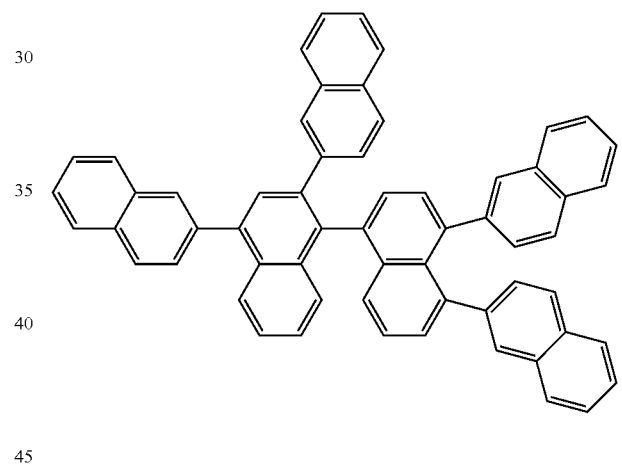
(78)
(81)
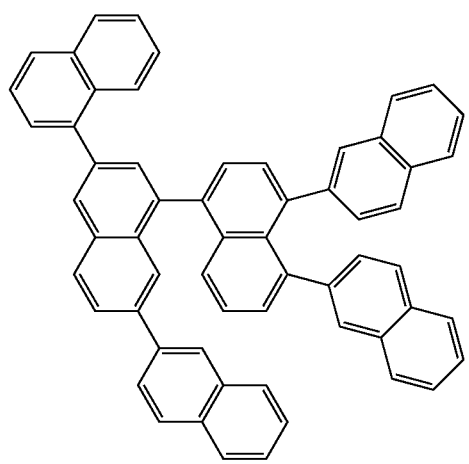
(79)
(82)

(83)
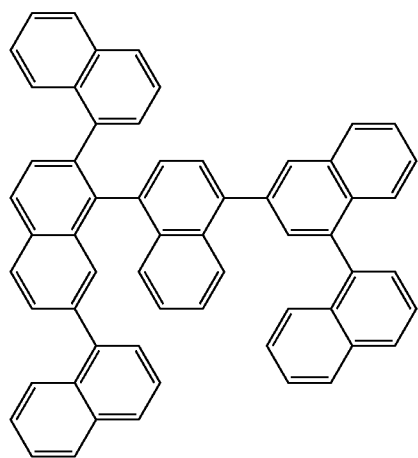
(86)
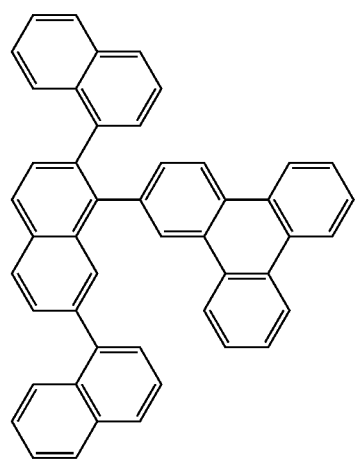
(84)
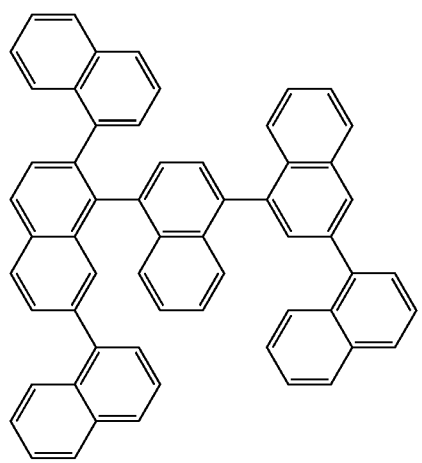
(87)
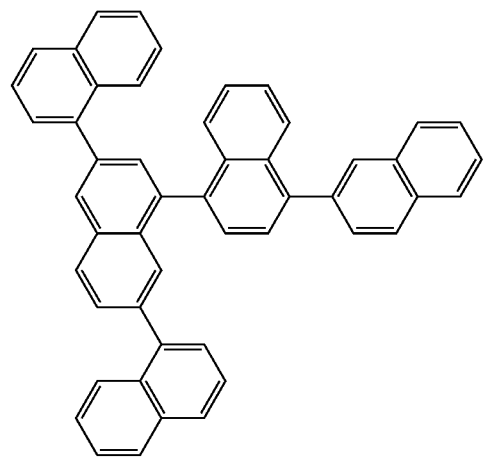
(85)
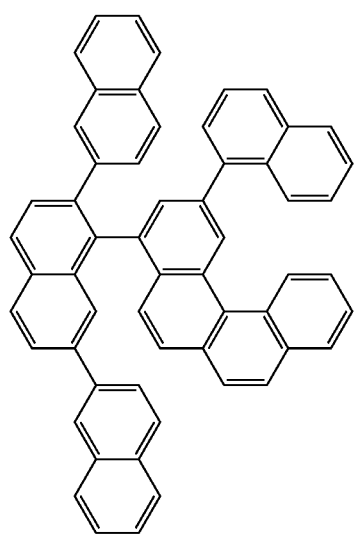
(88)
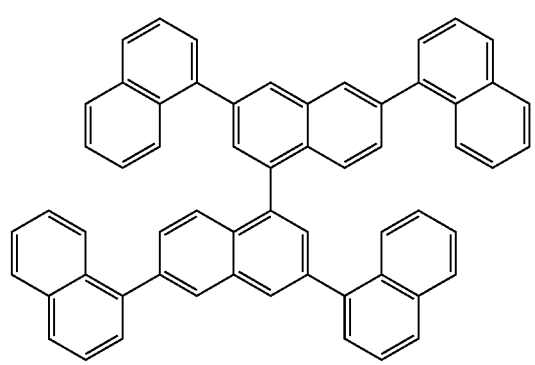

(89)
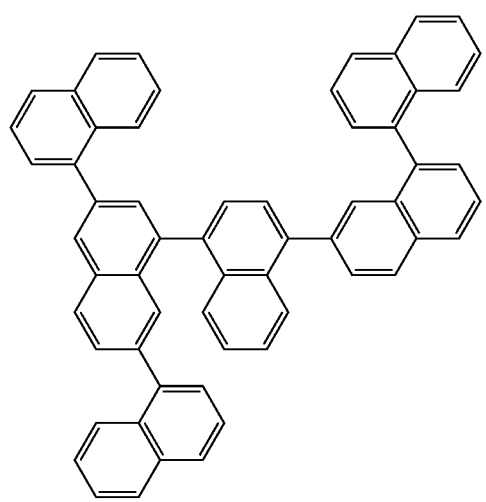
(92)
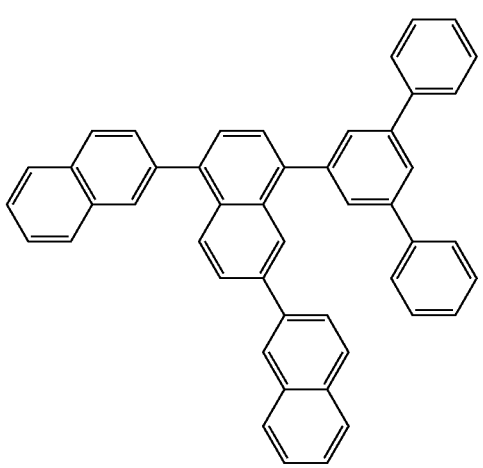
(90)
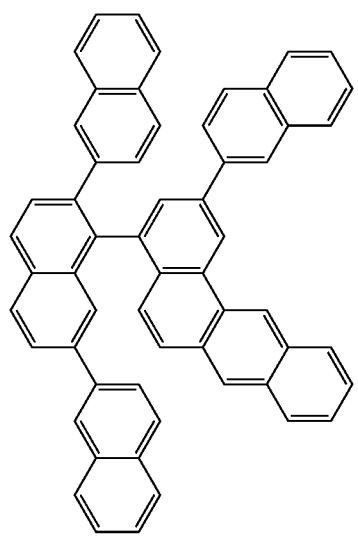
(93)
(91)
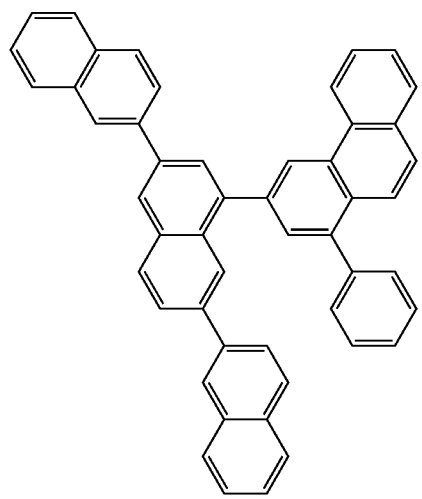
(94)
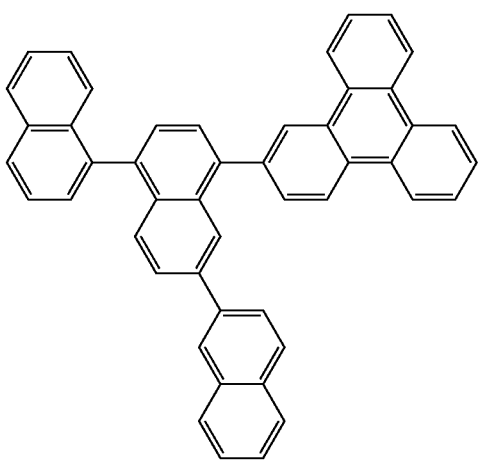

(95)
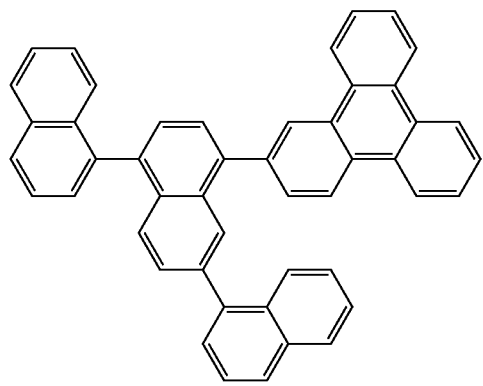
(96)
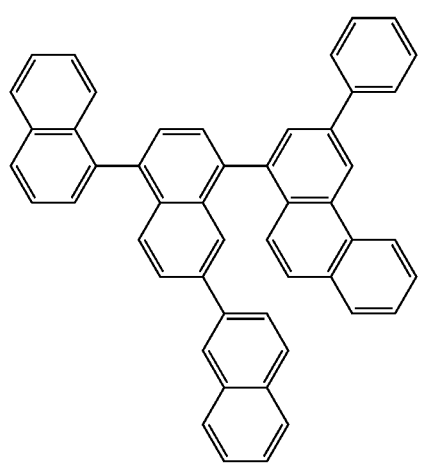
(97)
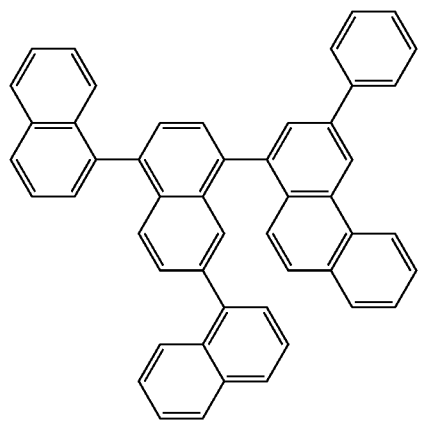
(98)
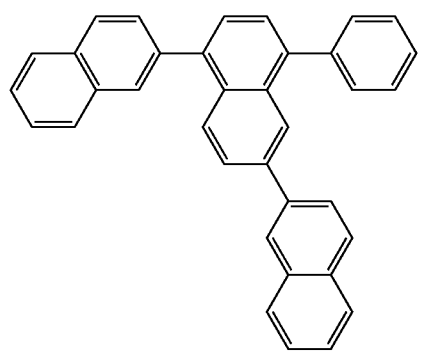
(99)
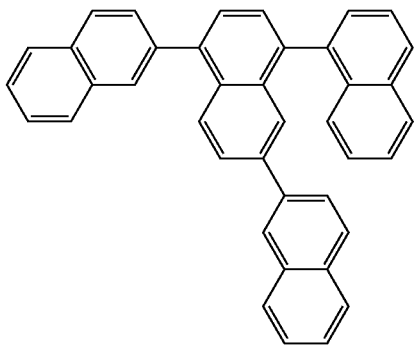
(100)
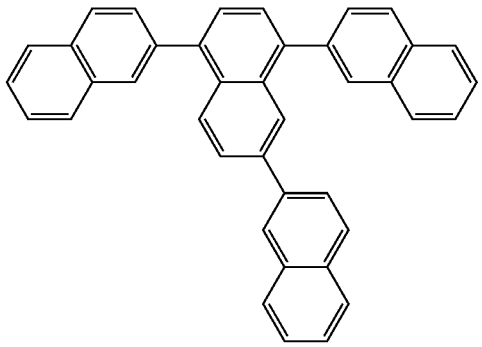
(101)
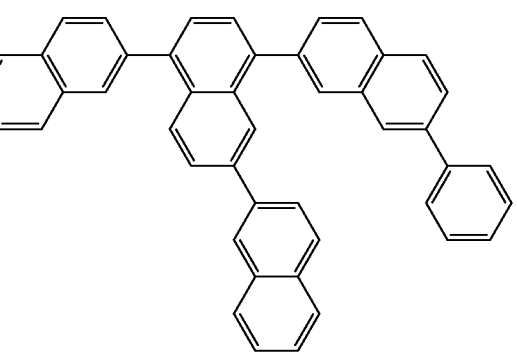
(102)
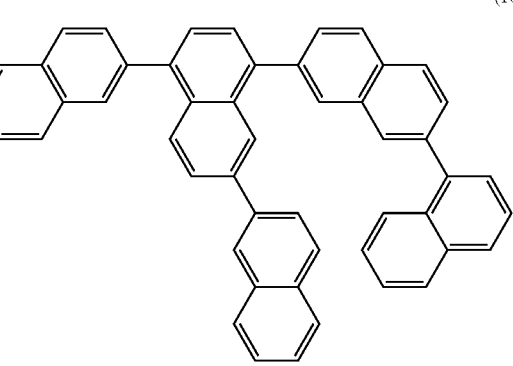

(103)
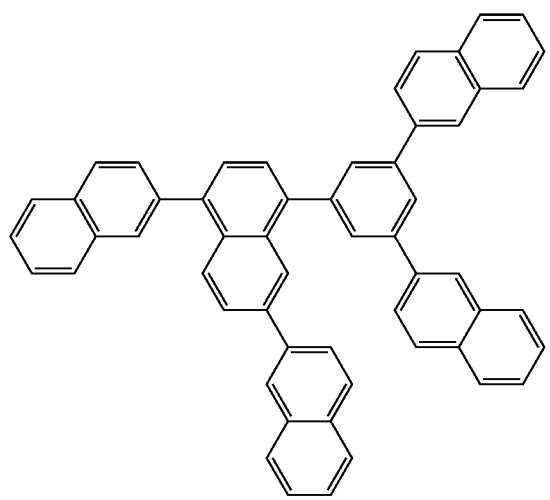
(104)
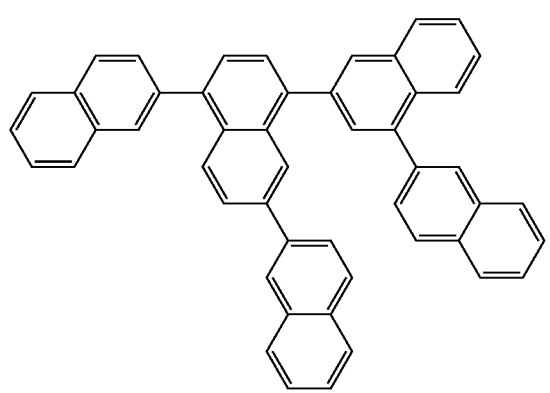
(105)
(106)
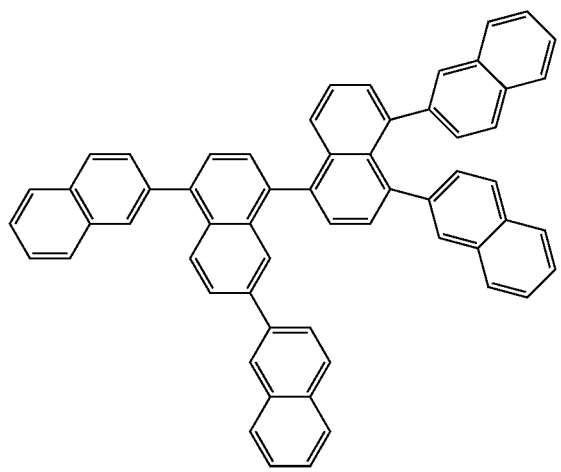
(107)
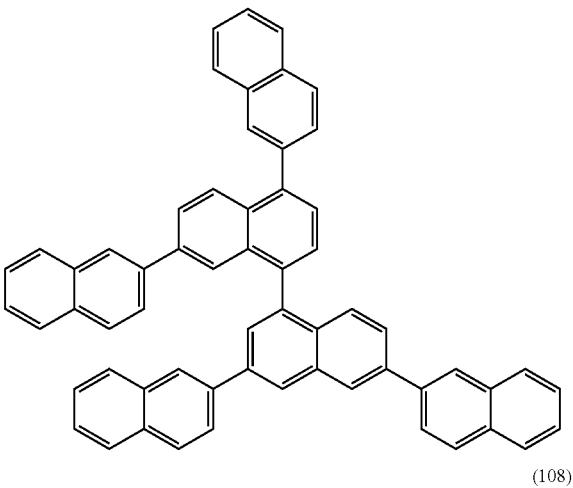
(108)

(109)
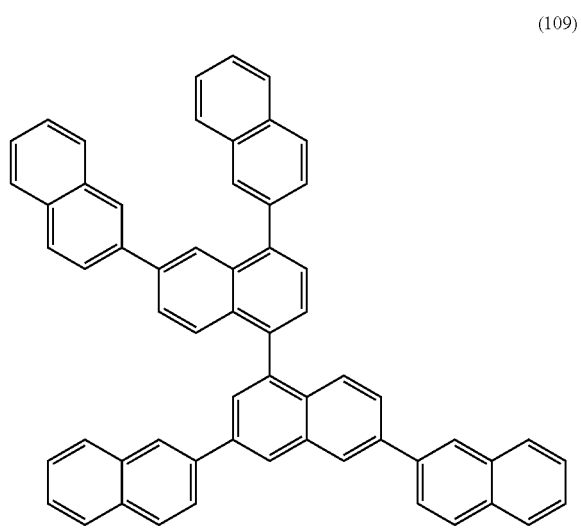
(110)
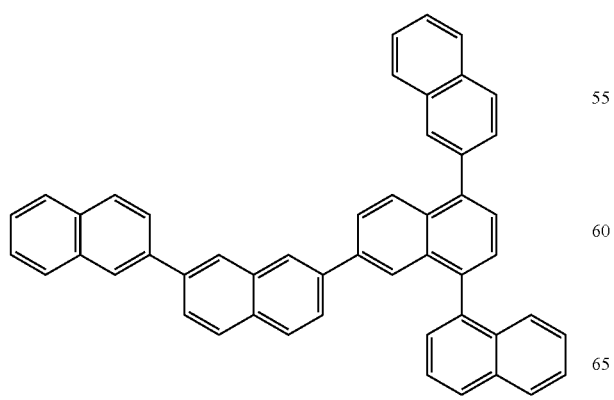
(111)
(112)
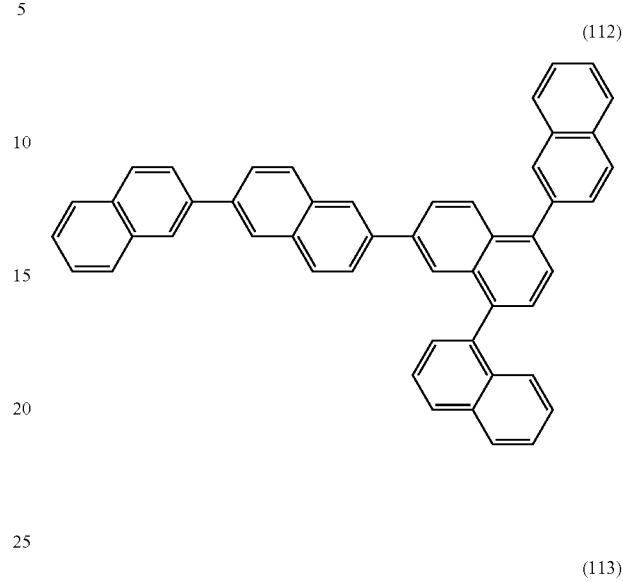
(113)
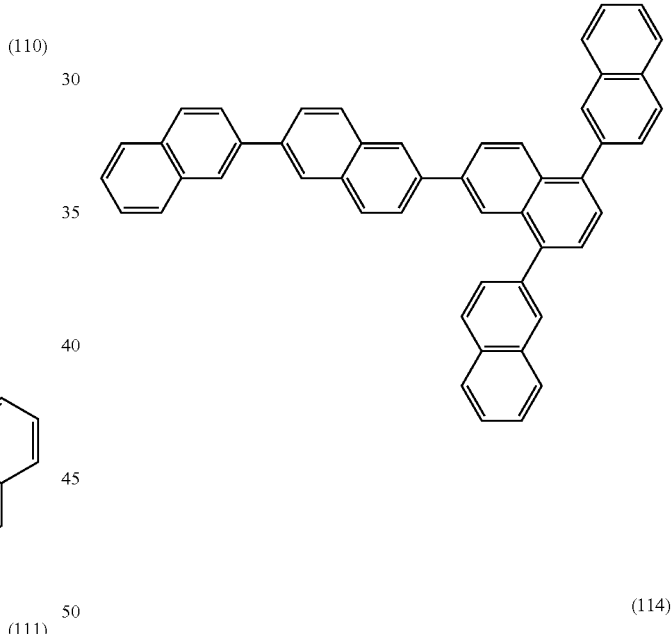
(114)
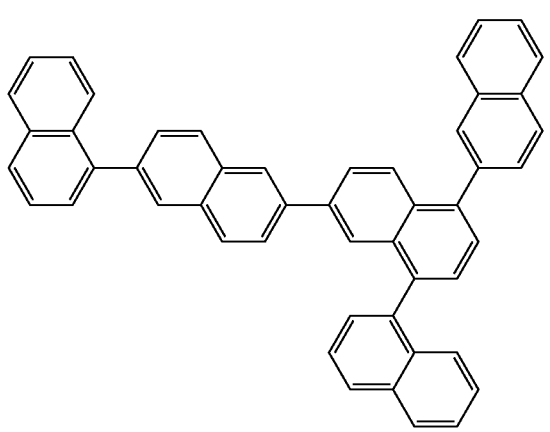

(115)
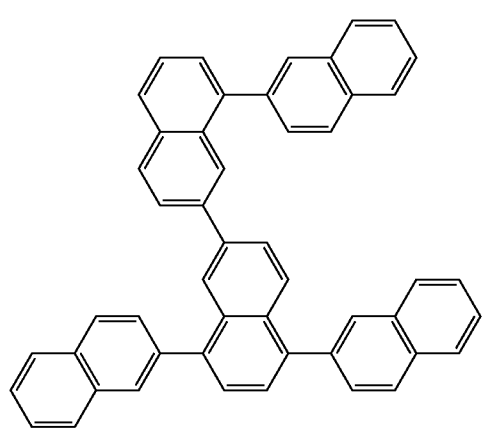
(116)
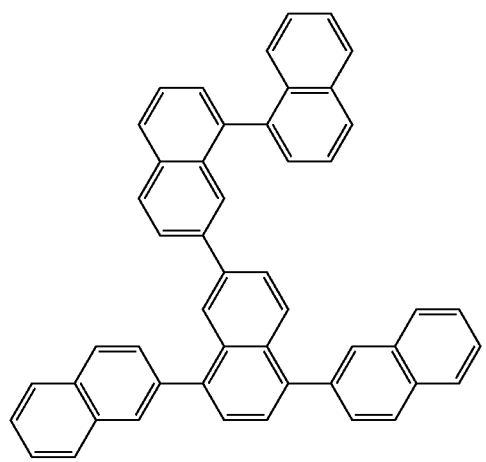
(117)
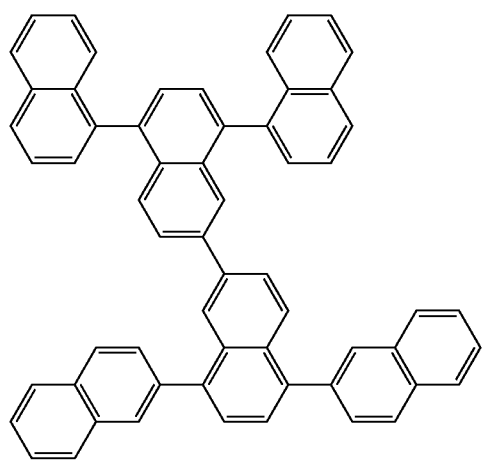
(118)
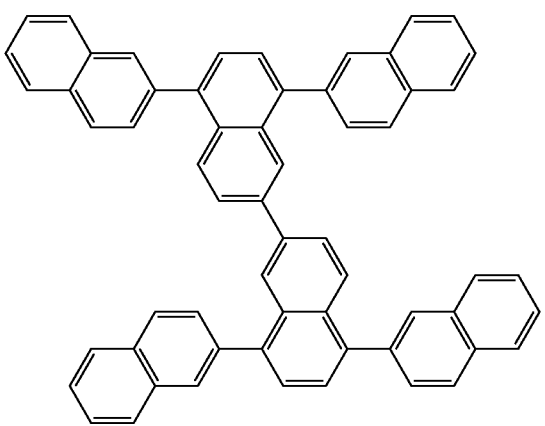
(119)
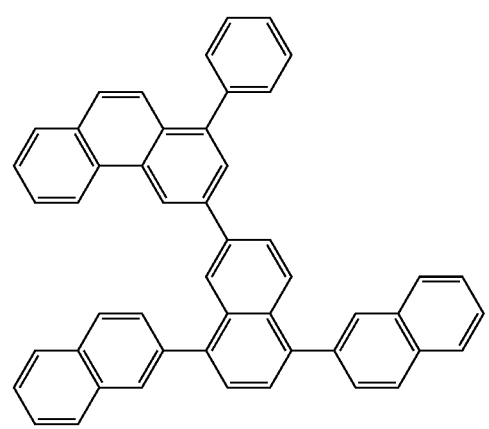
(120)
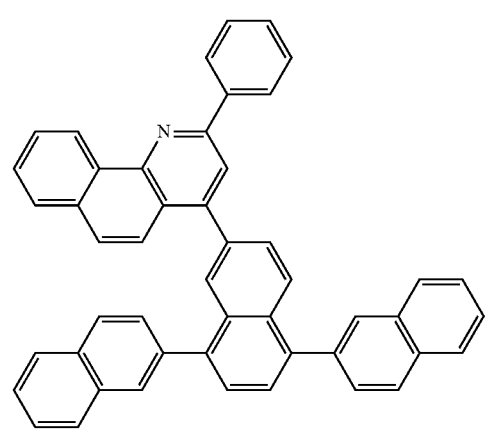

(121) 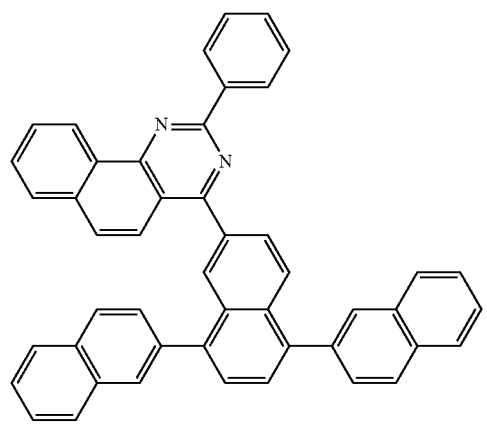
(122) 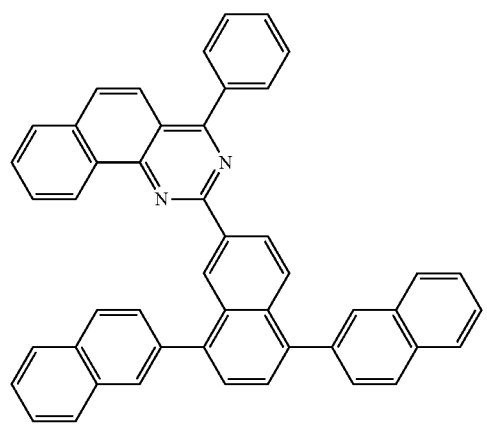
(123) 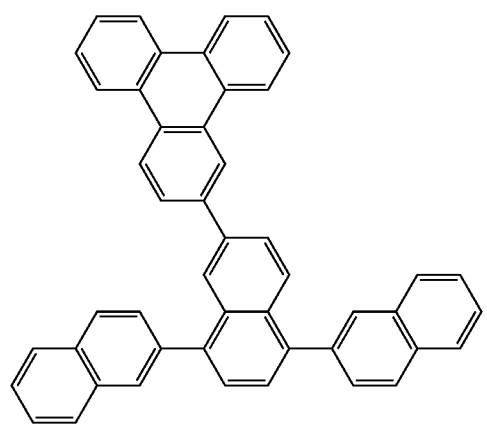
(124) 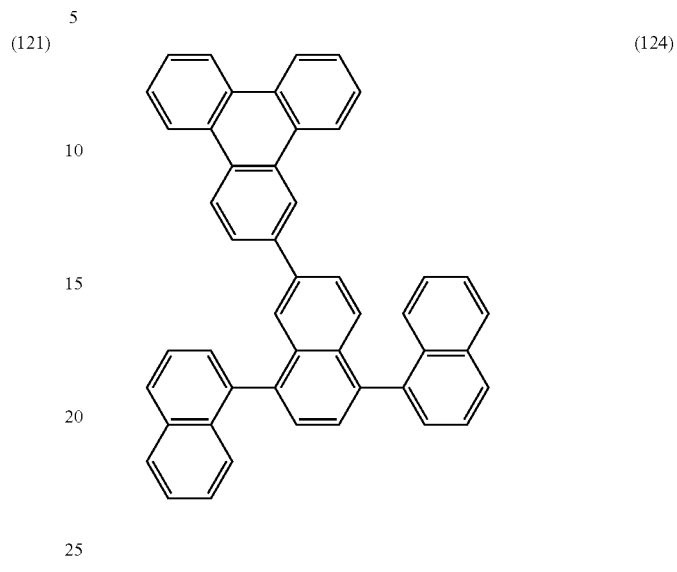
(125) 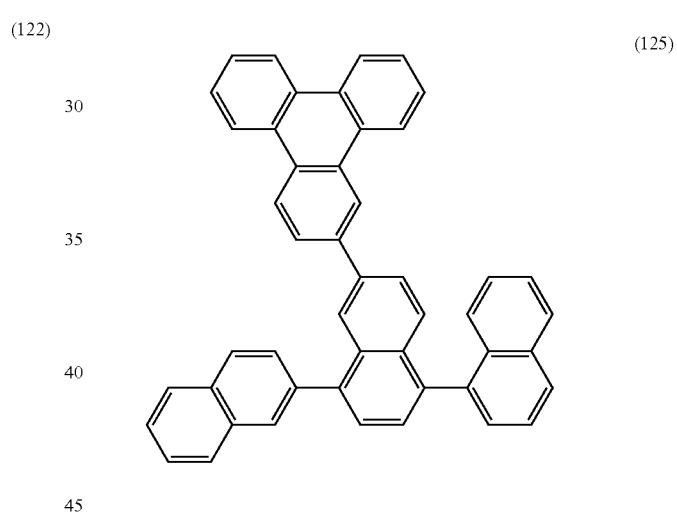
(126) 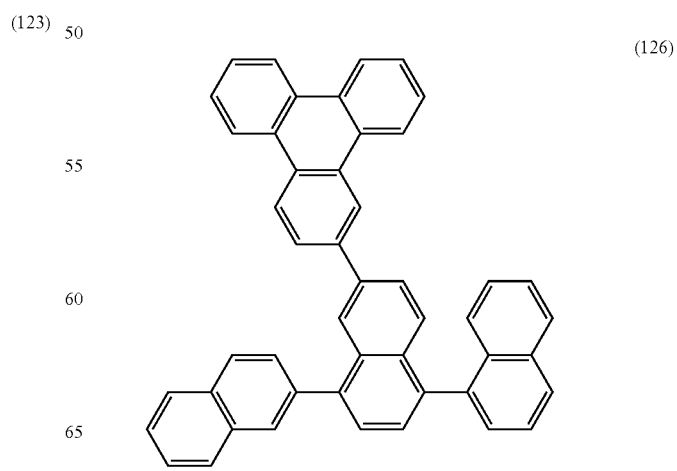

(127)
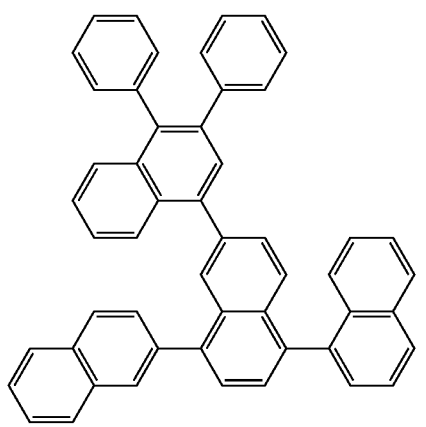
(119)
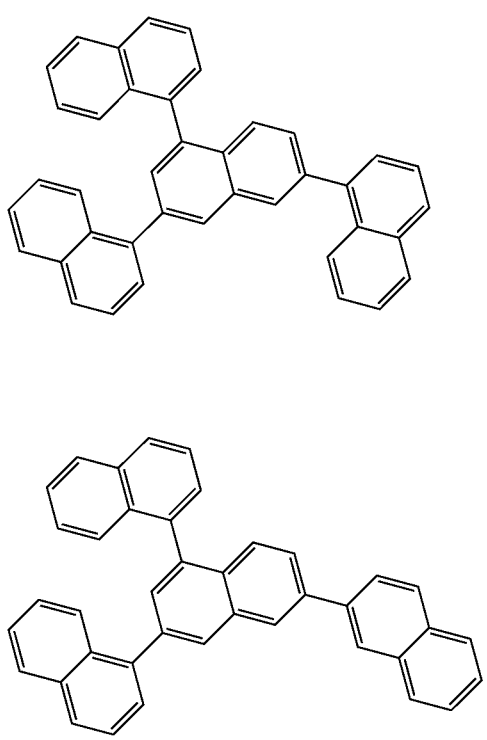
(120)
(121)
(122)
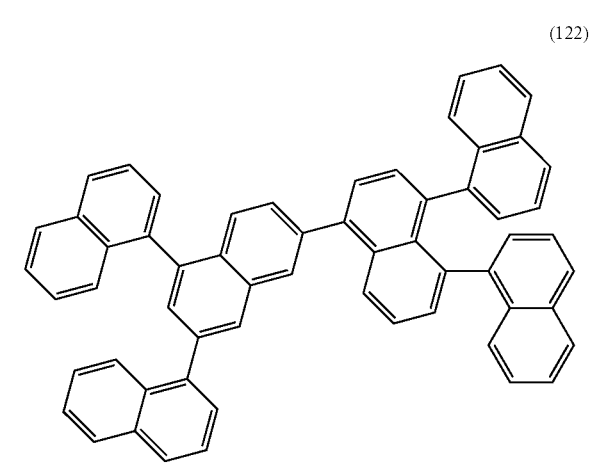
(123)
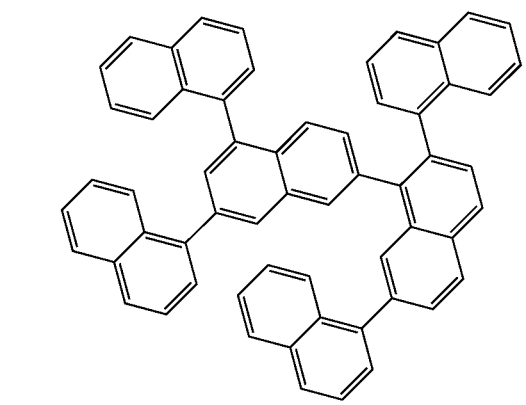
(124)
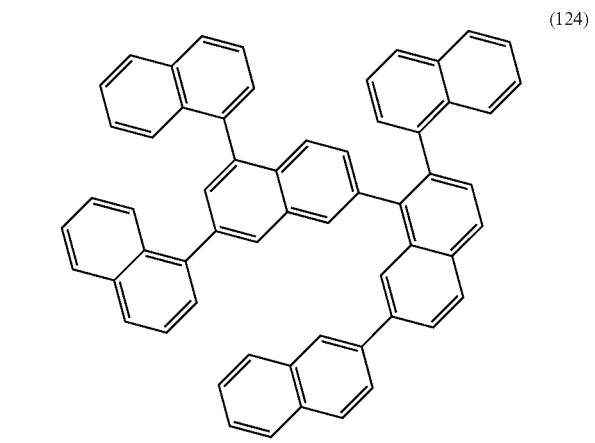

(125)

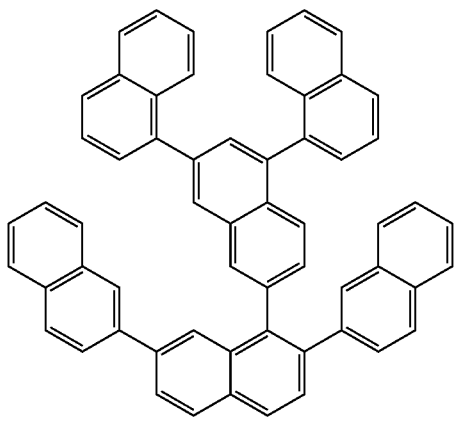

(126)

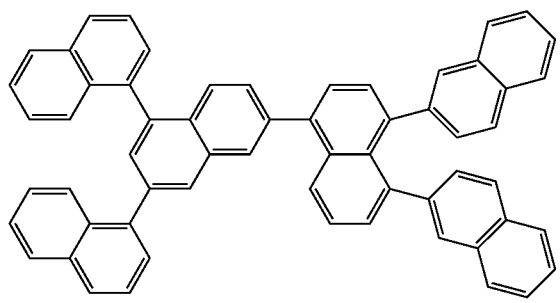

An application of the above organic compounds in a mixture is provided.

An application of the above organic compounds in a formulation is provided.

An application of the above organic compounds in an organic electronic device is provided.

A polymer according to an embodiment has at least one repeat unit comprising an organic compound represented by the general formula (1). In an embodiment, the polymer is a non-conjugated polymer in which the structural unit represented by the general formula (1) is on the side chain. In other embodiments, the polymer is a conjugated polymer.

An application of the above polymers in a formulation is provided. The above polymers may be applied in a mixture. The above polymers may also be applied in an organic electronic device.

An organic mixture according to an embodiment comprises the above organic compounds, and at least one other organic functional material, wherein the organic functional material is selected from the group consisting of a hole (also called electron hole) injection or transport material (HIM/HTM), a hole blocking material (HBM), an electron injection or transport material (EIM/ETM), an electron blocking material (EBM), an organic host material, a singlet emitter (fluorescent emitter), a triplet emitter (phosphorescent emitter), or an organic thermally activated delayed fluorescent material (TADF material). In some embodiment, the organic thermal activated delayed fluorescent material may be an organic light-emitting metal complex. For example, various organic functional materials are described in detail, for example, in WO2010135519A1, 0134784A1 and WO 2011110277A1, the entire contents of which are hereby incorporated by reference. The organic functional material can be a small molecule or a polymer material.

In an embodiment, the organic mixture comprises the above organic compound and a phosphorescent emitter. The organic compound according to the present disclosure can be used as a host, and in this embodiment, the weight percentage of the phosphorescent emitter of the mixture is no greater than 30% by weight. In an embodiment, the weight percentage of the phosphorescent emitter of the mixture is no greater than 25 wt %. In an embodiment, the weight percentage of the phosphorescent emitter of the mixture is no greater than 20 wt %.

In an embodiment, the organic mixture comprises the above organic compound and a host material. The organic compound according to the present disclosure can be used as a light emitting material, and in this embodiment, the weight percentage of the organic compound of the mixture is no greater than 30% by weight. In an embodiment, the weight percent of organic compound of the mixture is no greater than 25 wt %. In an embodiment, the weight percent of organic compound of the mixture is no greater than 20 wt %. In an embodiment, the weight percent of organic compound of the mixture is no greater than 15 wt %.

In an embodiment, the organic mixture comprises the above organic compound and a fluorescent emitter. The organic compound is used as a host material, and the weight percentage of the fluorescent emitter of the mixture is no greater than 15 wt %. In an embodiment, the weight percent of the fluorescent emitter of the mixture is no greater than 10 wt %. In an embodiment, the weight percent of the fluorescent emitter of the mixture is no greater than 8 wt %.

In an embodiment, the organic mixture comprises the above organic compound, a phosphorescent emitter, and a host material. In an embodiment, the organic compound according to the present disclosure may be used as an auxiliary light emitting material and a weight ratio of the organic compound to the fluorescent emitter ranges from 1:2 to 2:1. In another embodiment, the organic compound according to the present disclosure has a higher $T_1$ than the phosphorescent emitter.

In an embodiment, the organic mixture comprises the above organic compound and another TADF material.

The host material, the phosphorescent material and the TADF material are described in detail below (but are not limited thereto).

1. Triplet Host

Examples of a triplet host material are not particularly limited and any metal complex or organic compound can be used as the host as long as its triplet energy is greater than that of the emitter, especially the triplet emitter or phosphorescent emitter. Examples of metal complexes that may be used as triplet hosts may include, but are not limited to, the general structure as follows:

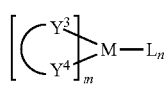

wherein M is a metal; ($Y^3$—$Y^4$) is a bidentate ligand, $Y^3$ and $Y^4$ are independently selected from C, N, O, P, or S; L is an auxiliary ligand; m is an integer with the value from 1 to the maximum coordination number of the metal; and m+n is the maximum number of coordination of the metal.

In an embodiment, the metal complex that can be used as the triplet host has the following formula:

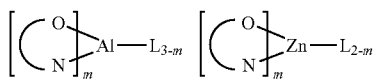

wherein, (O—N) is a bidentate ligand, in which the metal is coordinated to O and N atoms.

In an embodiment, M is selected from Ir or Pt.

Examples of organic compounds that can be used as the triplet host are selected from compounds containing cyclic aryl, such as benzene, biphenyl, triphenyl, benzo, and fluorene; or compounds containing heterocyclic aryl, such as dibenzothiophene, dibenzofuran, dibenzoselenophen, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, oxazole, bibenzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furopyridine, benzothienopyridine, thienopyridine, benzoselenophenopyridine, selenophenobenzodipyridine; or groups containing 2 to 10 ring structures, which may be the same or different types of cyclic aryl or heterocyclic aryl and are linked to each other directly or by at least one of the following groups, such as oxygen atom, nitrogen atom, sulfur atom, silicon atom, phosphorus atom, boron atom, chain structural unit, and aliphatic ring group. Each Ar may be further substituted and the substituents is selected from hydrogen, alkyl, alkoxy, amino, alkenyl, alkynyl, aralkyl, heteroalkyl, aryl, or heteroaryl.

In an embodiment, the triplet host material is selected from compounds including at least one of the following groups:

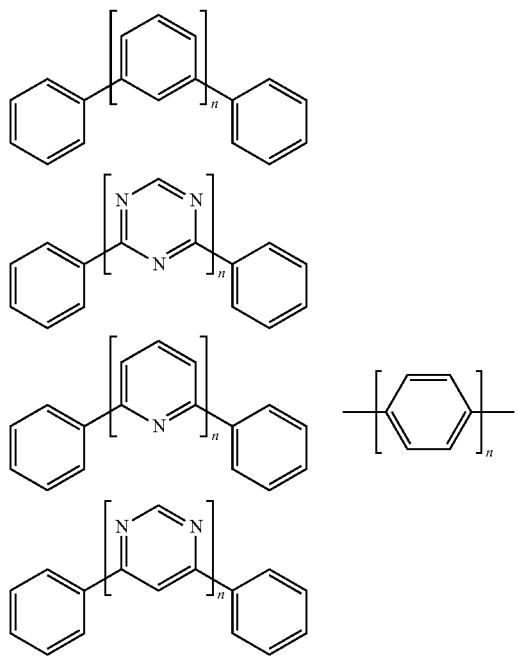

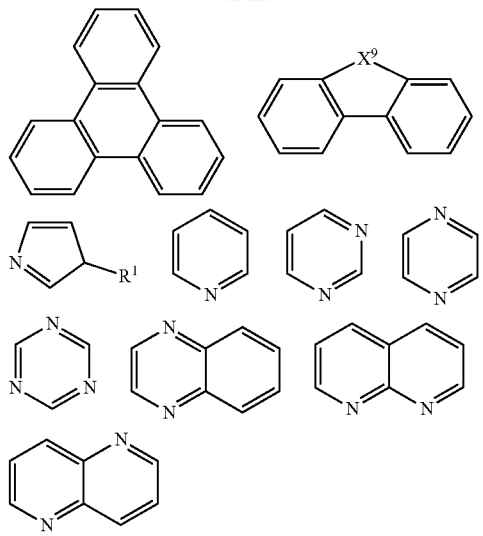

wherein $R^1$ to $R^7$ are independently selected from hydrogen, alkyl, alkoxy, amino, alkenyl, alkynyl, aralkyl, heteroalkyl, aryl or heteroaryl, and when $R^1$ to $R^7$ are aryl or heteroaryl, $R^1$ to $R^7$ have the same meaning as Art and Are described above; n is any integer selected from 0-20; $X^1$ to $X^8$ are selected from CH or N, $X^9$ is selected from $CR^1R^2$ or $NR^1$.

Examples of the suitable triplet host material are listed in the following table.

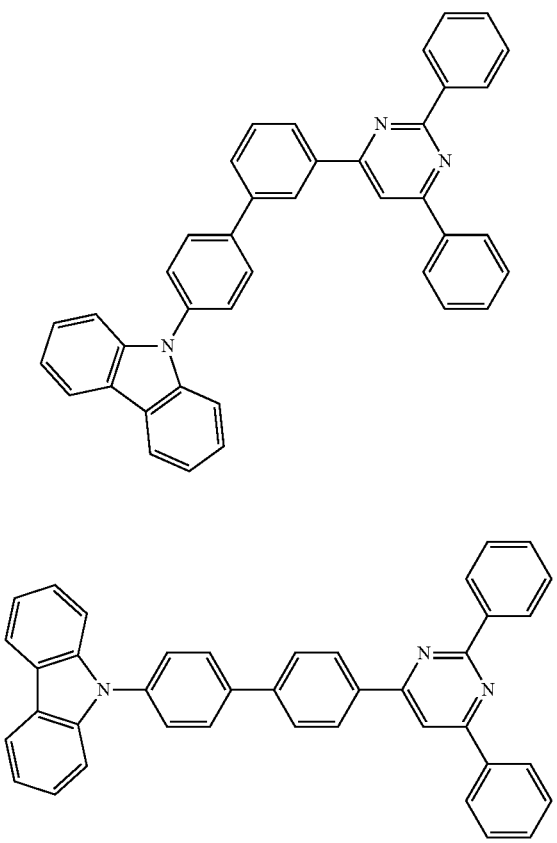

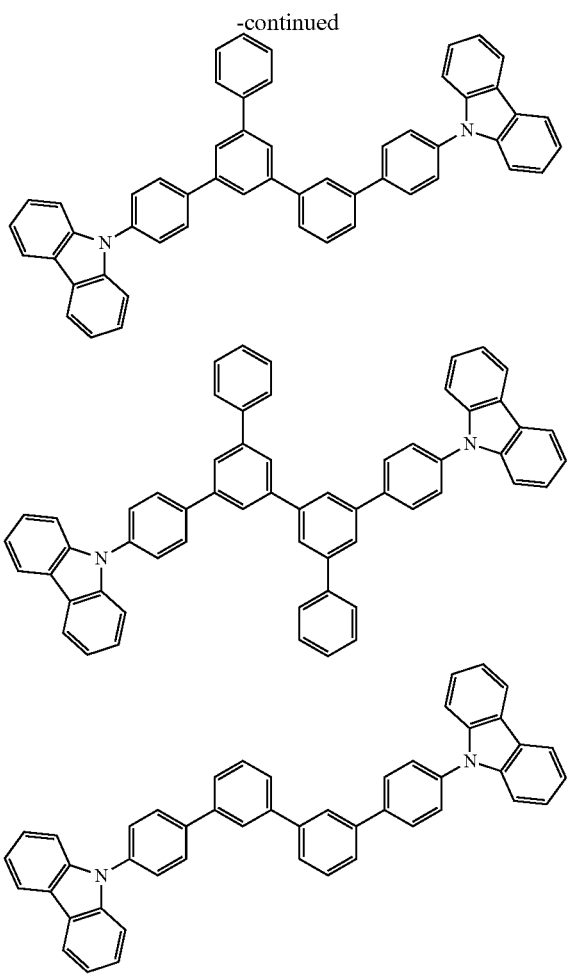

2. Phosphorescent Material

The phosphorescent material is also called a triplet emitter. In an embodiment, the triplet emitter is a metal complex having a general formula $M(L)_n$, wherein M is a metal atom; L may be the same or different organic ligand in each occurrence, and is bonded or coordinated to the metal atom M at one or more positions; and n is an integer greater than 1, especially, n is 1, 2, 3, 4, 5 or 6. In an embodiment, these metal complexes are attached to one polymer by one or more positions, optimally by an organic ligand.

In an embodiment, the metal atom M is selected from the group consisting of transition metal elements, lanthanide elements, and actinide elements. In an embodiment, M is selected from Ir, Pt, Pd, Au, Rh, Ru, Os, Sm, Eu, Gd, Tb, Dy, Re, Cu or Ag. In one embodiment, M is selected from Os, Ir, Ru, Re, Pd or Pt.

In one embodiment, the triplet emitter includes a chelating ligand, i.e., a ligand, coordinated to the metal by at least two bonding sites. In another embodiment, the triplet emitter includes two or three identical or different bidentate or multidentate ligand. Chelating ligands help to improve stability of metal complexes.

Examples of organic ligands are selected from the group consisting of phenylpyridine derivative, 7, 8-benzoquinoline derivative, 2(2-thienyl) pyridine derivative, 2(1-naphthyl) pyridine derivative, and 2 phenylquinoline derivative. All of these organic ligands can be substituted, for example, by fluoromethyl or trifluoromethyl. The auxiliary ligand may be selected from acetylacetonate or picric acid.

In one embodiment, the metal complex which can be used as the triplet emitter has the following form:

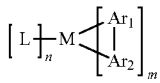

M is a metal and selected from transition metal elements, lanthanide elements, or actinide elements.

$Ar^1$ is a cyclic group, which may be the same or different at each occurrence, and $Ar^1$ contains at least one donor atom, i.e. an atom containing a lone pair of electrons, such as nitrogen or phosphorus, through which the cyclic group is coordinated to the metal; $Ar^2$ is a cyclic group, which may be the same or different at each occurrence, and $Ar^2$ includes at least one C atom and through which the cyclic group is attached to the metal; $Ar_1$ and Ar2 are covalently bonded together, and may each carry one or more substituents, or may also be linked together by substituents; L may be the same or different at each occurrence and is an auxiliary ligand, especially a bidentate chelating ligand, particularly a monoanionic bidentate chelating ligand; m is selected from 1, 2 or 3; and n is selected from 0, 1 or 2. In an embodiment, L is a bidentate chelating ligand. In an embodiment, L is a monoanionic bidentate chelating ligand. In an embodiment, m is 2 or 3. In an embodiment, m is 3. n is 0, 1, or 2. In an embodiment, n is 0 or 1. In an embodiment, n is 0.

Some examples of triplet emitter materials and applications thereof can be found in the following patent documents and references: WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219 A1, US 20090061681 A1, US 20010053462 A1, Baldo, Thompson et al. Nature 403, (2000), 750-753, US 20090061681 A1, US 20090061681 A1, Adachi et al. Appl. Phys. Lett. 78 (2001), 1622-1624, J. Kido et al. Appl. Phys. Lett. 65 (1994), 2124, Kido et al. Chem. Lett. 657, 1990, US 2007/0252517 A1, Johnson et al., JACS 105, 1983, 1795, Wrighton, JACS 96, 1974, 998, Ma et al., Synth. Metals 94, 1998, 245, U.S. Pat. Nos. 6,824,895, 7,029,766, 6,835,469, 6,830,828, US 20010053462 A1, WO 2007095118 A1, US 2012004407A1, WO 2012007088A1, WO2012007087A1, WO 2012007086A1, US 2008027220A1, WO 2011157339A1, CN 102282150A, WO 2009118087A1. All the contents of the above patent documents and references are hereby incorporated by reference.

3. TADF Materials

Traditional organic fluorescent materials can only emit light using 25% singlet excitonic luminescence formed by electrical excitation, and the devices have relatively low internal quantum efficiency (up to 25%). The phosphorescent material enhances the intersystem crossing due to the strong spin-orbit coupling of the heavy atom center, the singlet exciton and the triplet exciton luminescence formed by the electric excitation can be effectively utilized, so that the internal quantum efficiency of the device can reach 100%. However, the phosphor materials are expensive, the material stability is poor, and the device efficiency roll-off is a serious problem, which limit its application in OLED. Thermally-activated delayed fluorescent materials are the third generation of organic light-emitting materials developed after organic fluorescent materials and organic phosphorescent materials. This type of material generally has a small singlet-triplet energy level difference (ΔEst), and triplet excitons can be converted to singlet excitons by intersystem crossing. This can make full use of the singlet excitons and triplet excitons formed under electric excitation. The device can achieve 100% internal quantum efficiency. At the same time, the material is controllable in structure, stable in property, and low cost without precious metals, and has a promising prospect of application in the OLED field.

The TADF material needs to have a small singlet-triplet energy level difference. In an embodiment, $\Delta E_{st}$<0.3 eV. In another embodiment, $\Delta E_{st}$<0.2 eV. In some embodiment, $\Delta E_{st}$<0.1 eV. In an embodiment, the TADF material has a relatively small $\Delta E_{st}$. In another embodiment, TADF has good fluorescence quantum efficiency. Some TADF emitting materials can be found in the following patent documents: CN103483332(A), TW201309696(A), TW201309778(A), TW201343874(A), TW201350558(A), US20120217869 (A1), WO2013133359(A1), WO2013154064 (A1), Adachi, et.al. Adv. Mater., 21, 2009, 4802, Adachi, et.al. Appl. Phys. Lett., 98, 2011, 083302, Adachi, et.al. Appl. Phys. Lett., 101, 2012, 093306, Adachi, et.al. Chem. Commun., 48, 2012, 11392, Adachi, et.al. Nature Photonics, 6, 2012, 253, Adachi, et.al. Nature, 492, 2012, 234, Adachi, et.al. J. Am. Chem. Soc, 134, 2012, 14706, Adachi, et.al. Angew. Chem. Int. Ed, 51, 2012, 11311, Adachi, et.al. Chem. Commun., 48, 2012, 9580, Adachi, et.al. Chem. Commun., 48, 2013, 10385, Adachi, et.al. Adv. Mater., 25, 2013, 3319, Adachi, et.al. Adv. Mater., 25, 2013, 3707, Adachi, et.al. Chem. Mater., 25, 2013, 3038, Adachi, et.al. Chem. Mater., 25, 2013, 3766, Adachi, et. Al. J. Mater. Chem. C., 1, 2013, 4599, Adachi, et.al. J. Phys. Chem. A., 117, 2013, 5607. The entire contents of the above listed patent or literature documents are hereby incorporated by reference.

Some examples of suitable TADF light-emitting materials are listed in the following table:

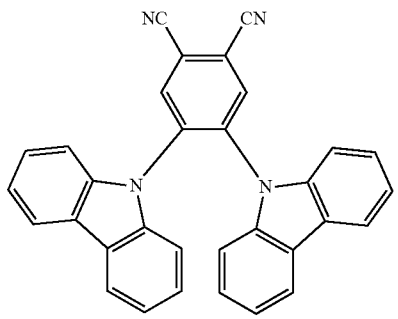 [SMILES: N#Cc1cc(-n2c3ccccc3c3ccccc32)c(-n2c3ccccc3c3ccccc32)cc1C#N]

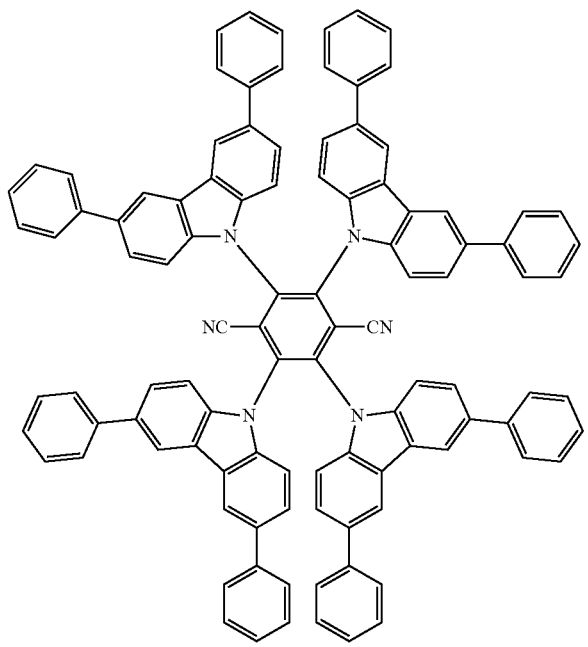 [SMILES: N#Cc1c(-n2c3ccc(-c4ccccc4)cc3c3cc(-c4ccccc4)ccc32)c(-n2c3ccc(-c4ccccc4)cc3c3cc(-c4ccccc4)ccc32)c(C#N)c(-n2c3ccc(-c4ccccc4)cc3c3cc(-c4ccccc4)ccc32)c1-n1c2ccc(-c3ccccc3)cc2c2cc(-c3ccccc3)ccc21]

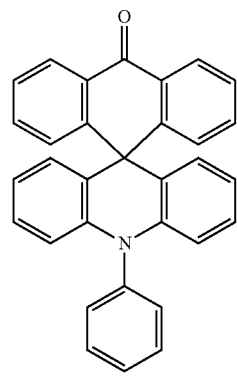 [SMILES: O=C1c2ccccc2C2(c3ccccc31)c1ccccc1N(c1ccccc1)c1ccccc12]
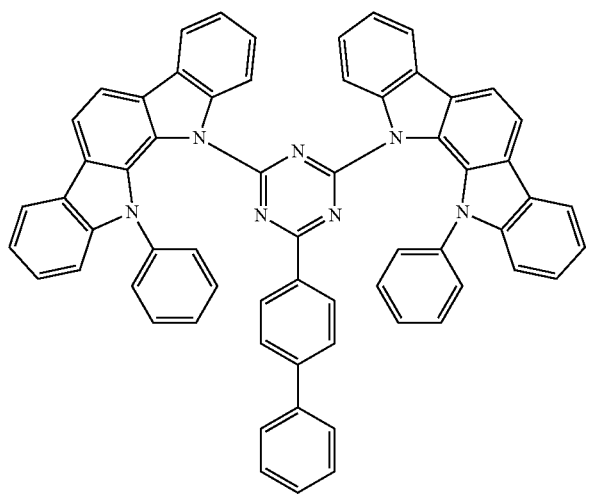 [SMILES: c1ccc(-c2ccc(-c3nc(-n4c5ccccc5c5ccc6c7ccccc7n(-c7ccccc7)c6c54)nc(-n4c5ccccc5c5ccc6c7ccccc7n(-c7ccccc7)c6c54)n3)cc2)cc1]
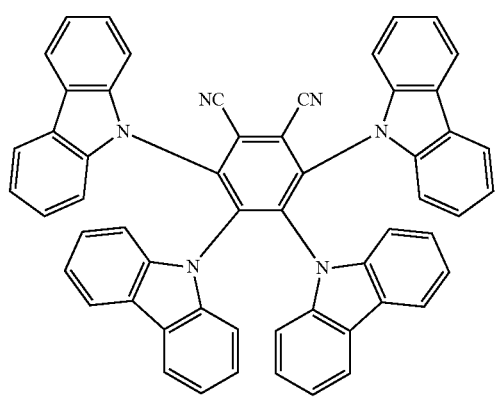 [SMILES: N#Cc1c(C#N)c(-n2c3ccccc3c3ccccc32)c(-n2c3ccccc3c3ccccc32)c(-n2c3ccccc3c3ccccc32)c1-n1c2ccccc2c2ccccc21]

-continued
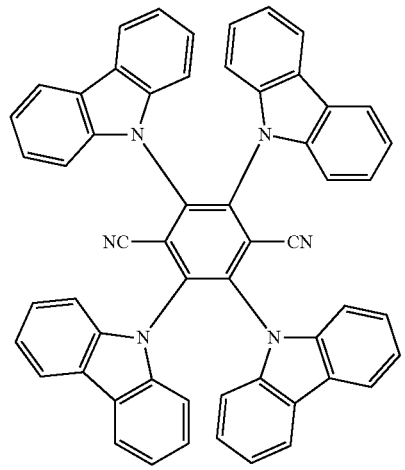 [SMILES: N#Cc1c(-n2c3ccccc3c3ccccc32)c(-n2c3ccccc3c3ccccc32)c(C#N)c(-n2c3ccccc3c3ccccc32)c1-n1c2ccccc2c2ccccc21]
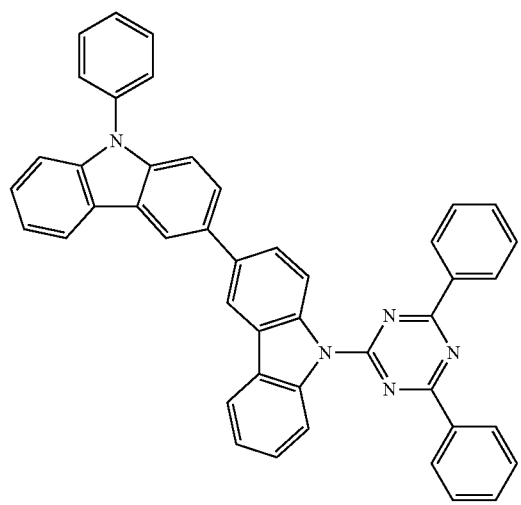 [SMILES: c1ccc(-c2nc(-c3ccccc3)nc(-n3c4ccccc4c4cc(-c5ccc6c(c5)c5ccccc5n6-c5ccccc5)ccc43)n2)cc1]
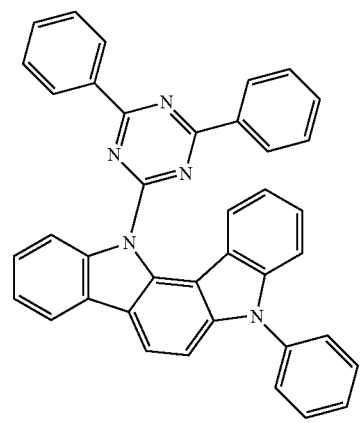 [SMILES: c1ccc(-c2nc(-c3ccccc3)nc(-n3c4ccccc4c4ccc5c(c6ccccc6n5-c5ccccc5)c43)n2)cc1]

-continued
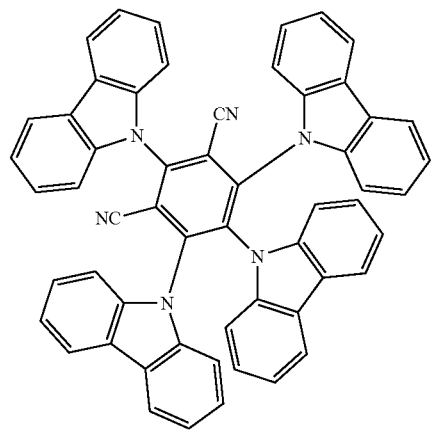 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]
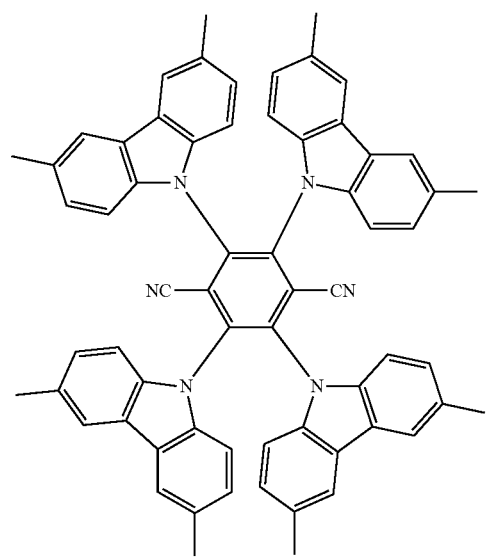
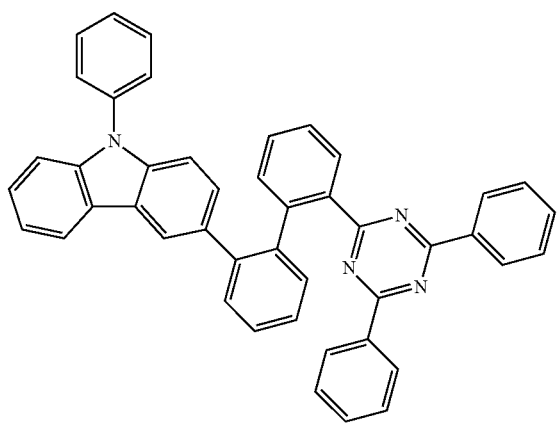 [SMILES: c1ccc(-c2nc(-c3ccccc3)nc(-c3ccccc3-c3ccccc3-c3ccc4c(c3)c3ccccc3n4-c3ccccc3)n2)cc1]

-continued
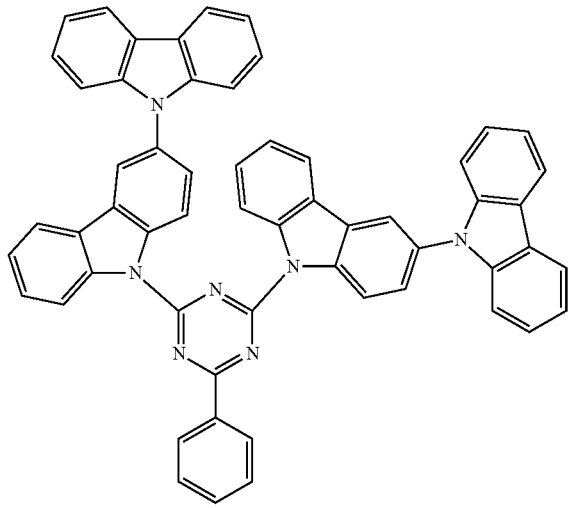 [SMILES: c1ccc(-c2nc(-n3c4ccccc4c4cc(-n5c6ccccc6c6ccccc65)ccc43)nc(-n3c4ccccc4c4cc(-n5c6ccccc6c6ccccc65)ccc43)n2)cc1]
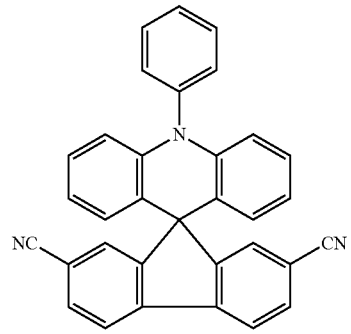 [SMILES: N#Cc1ccc2c(c1)C1(c3cc(C#N)ccc3-2)c2ccccc2N(c2ccccc2)c2ccccc21]
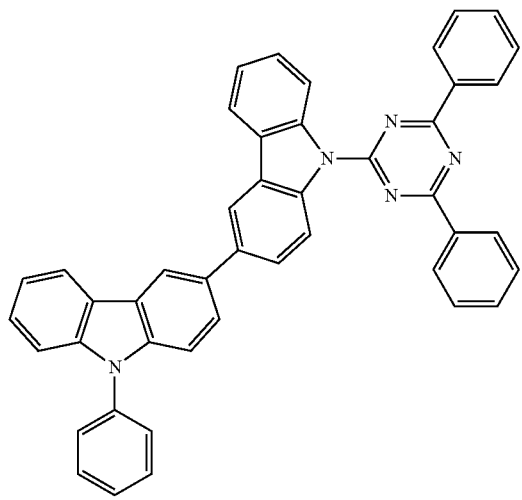 [SMILES: c1ccc(-c2nc(-c3ccccc3)nc(-n3c4ccccc4c4cc(-c5ccc6c(c5)c5ccccc5n6-c5ccccc5)ccc43)n2)cc1]
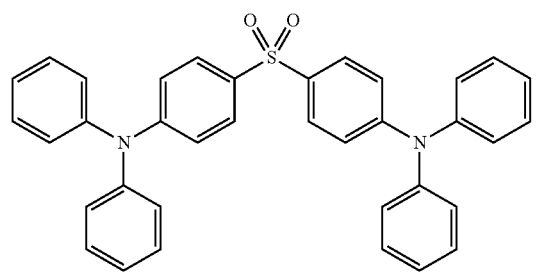 [SMILES: O=S(=O)(c1ccc(N(c2ccccc2)c2ccccc2)cc1)c1ccc(N(c2ccccc2)c2ccccc2)cc1]

-continued
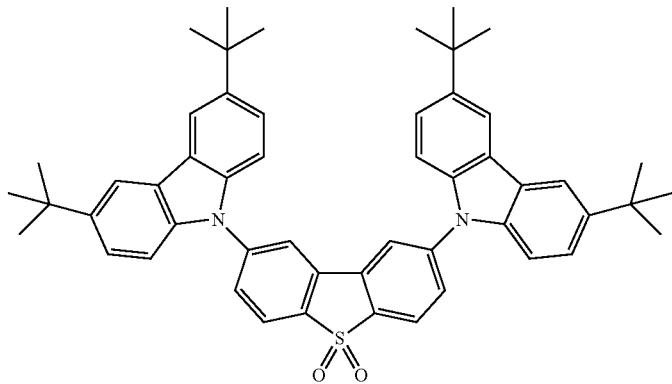 [SMILES: CC(C)(C)c1ccc2c(c1)c1cc(C(C)(C)C)ccc1n2-c1ccc2c(c1)-c1cc(-n3c4ccc(C(C)(C)C)cc4c4cc(C(C)(C)C)ccc43)ccc1S2(=O)=O]
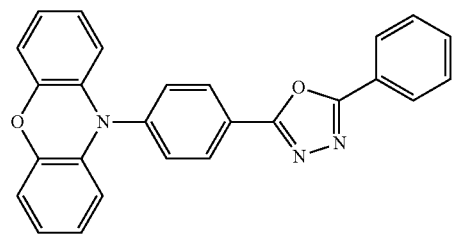 [SMILES: c1ccc(-c2nnc(-c3ccc(N4c5ccccc5Oc5ccccc54)cc3)o2)cc1]
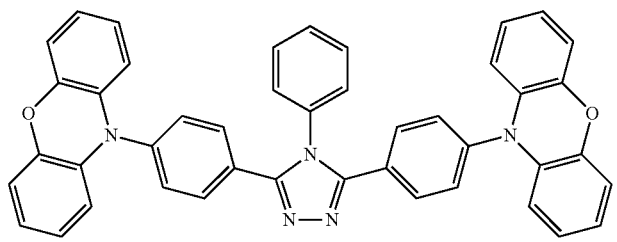 [SMILES: c1ccc(-n2c(-c3ccc(N4c5ccccc5Oc5ccccc54)cc3)nnc2-c2ccc(N3c4ccccc4Oc4ccccc43)cc2)cc1]
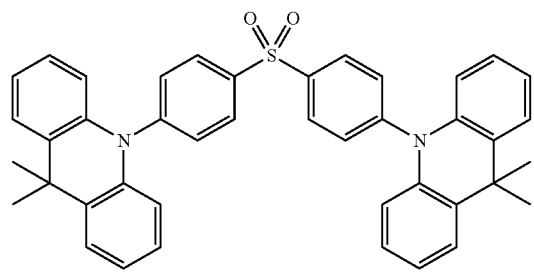 [SMILES: CC1(C)c2ccccc2N(c2ccc(S(=O)(=O)c3ccc(N4c5ccccc5C(C)(C)c5ccccc54)cc3)cc2)c2ccccc21]
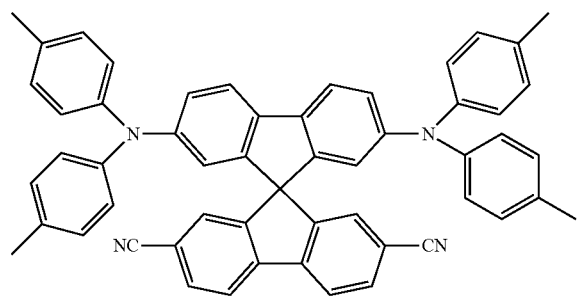

-continued
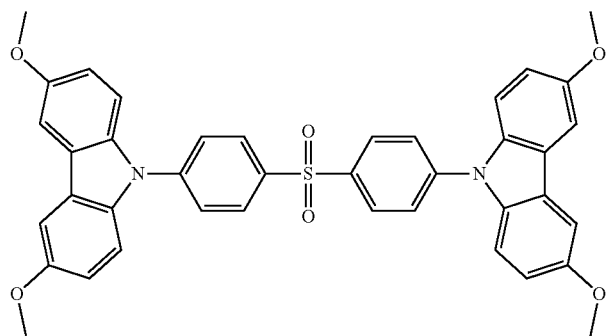 [SMILES: COc1ccc2c(c1)c1cc(OC)ccc1n2-c1ccc(S(=O)(=O)c2ccc(-n3c4ccc(OC)cc4c4cc(OC)ccc43)cc2)cc1]
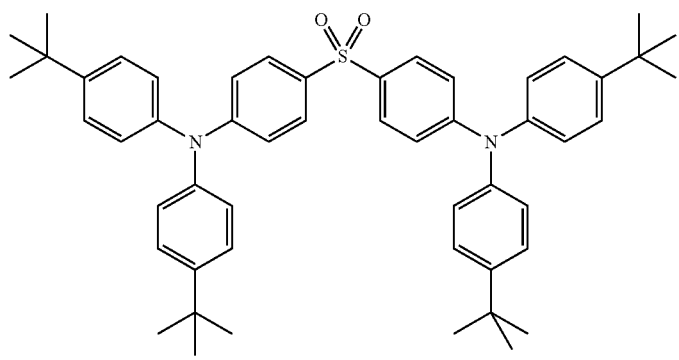 [SMILES: CC(C)(C)c1ccc(N(c2ccc(C(C)(C)C)cc2)c2ccc(S(=O)(=O)c3ccc(N(c4ccc(C(C)(C)C)cc4)c4ccc(C(C)(C)C)cc4)cc3)cc2)cc1]
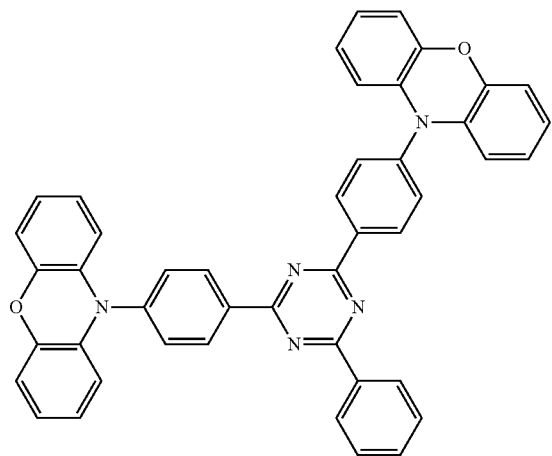 [SMILES: c1ccc(-c2nc(-c3ccc(N4c5ccccc5Oc5ccccc54)cc3)nc(-c3ccc(N4c5ccccc5Oc5ccccc54)cc3)n2)cc1]
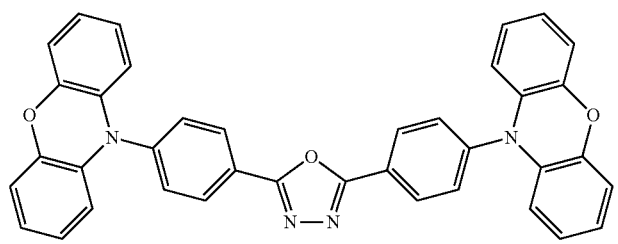 [SMILES: c1ccc2c(c1)Oc1ccccc1N2c1ccc(-c2nnc(-c3ccc(N4c5ccccc5Oc5ccccc54)cc3)o2)cc1]

-continued
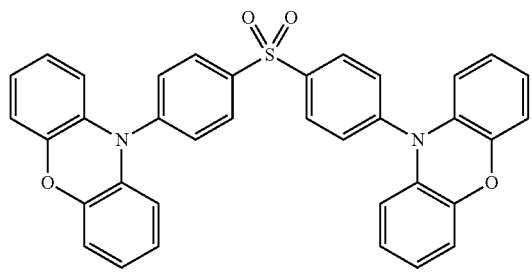 [SMILES: O=S(=O)(c1ccc(N2c3ccccc3Oc3ccccc32)cc1)c1ccc(N2c3ccccc3Oc3ccccc32)cc1]
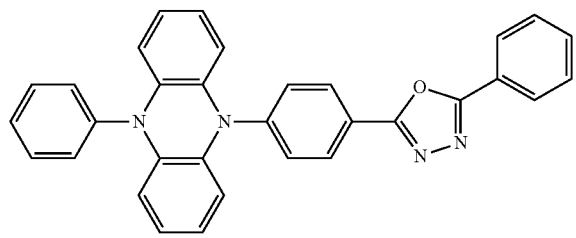 [SMILES: c1ccc(-c2nnc(-c3ccc(N4c5ccccc5N(c5ccccc5)c5ccccc54)cc3)o2)cc1]
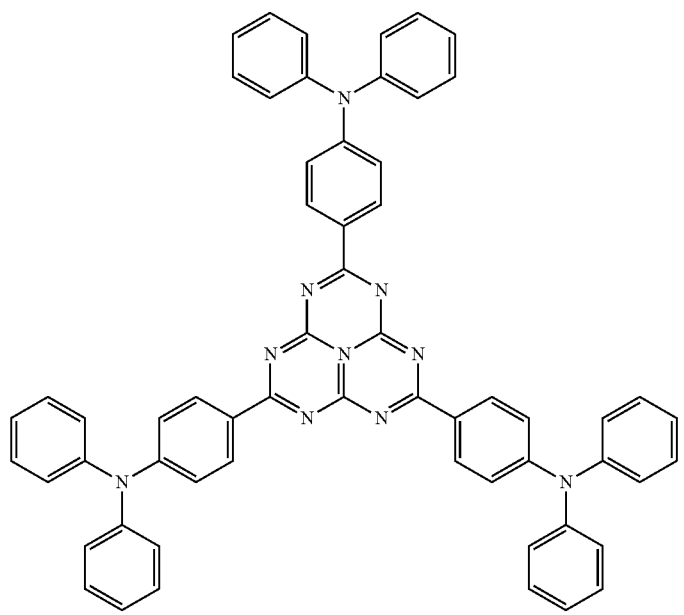
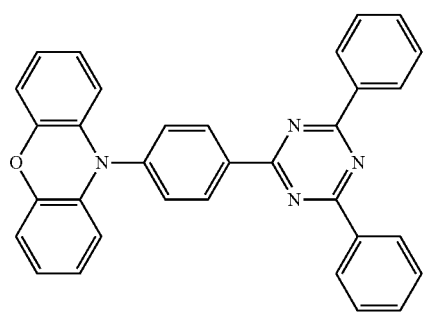 [SMILES: c1ccc(-c2nc(-c3ccccc3)nc(-c3ccc(N4c5ccccc5Oc5ccccc54)cc3)n2)cc1]

-continued
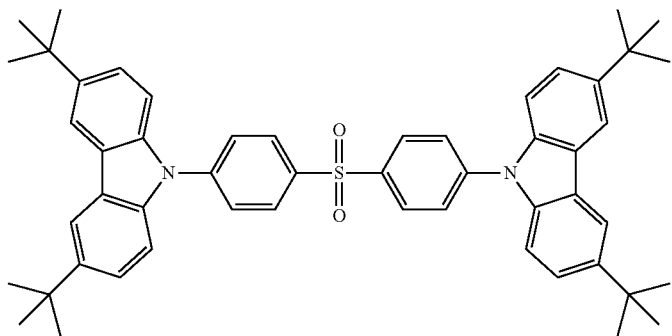 [SMILES: CC(C)(C)c1ccc2c(c1)c1cc(C(C)(C)C)ccc1n2-c1ccc(S(=O)(=O)c2ccc(-n3c4ccc(C(C)(C)C)cc4c4cc(C(C)(C)C)ccc43)cc2)cc1]
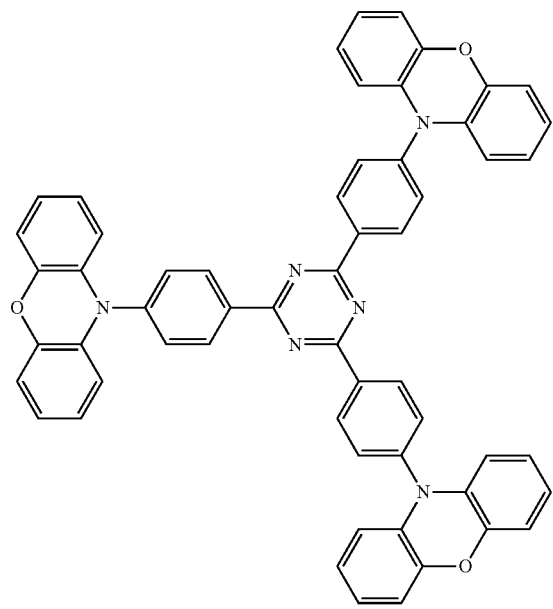 [SMILES: c1ccc2c(c1)Oc1ccccc1N2c1ccc(-c2nc(-c3ccc(N4c5ccccc5Oc5ccccc54)cc3)nc(-c3ccc(N4c5ccccc5Oc5ccccc54)cc3)n2)cc1]
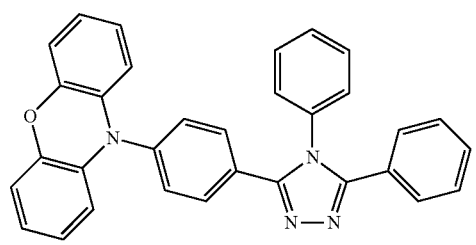 [SMILES: c1ccc(-c2nnc(-c3ccc(N4c5ccccc5Oc5ccccc54)cc3)n2-c2ccccc2)cc1]
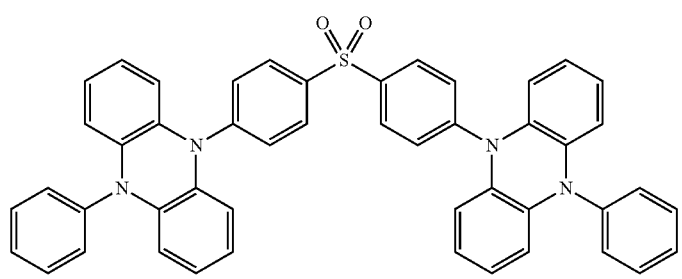 [SMILES: O=S(=O)(c1ccc(N2c3ccccc3N(c3ccccc3)c3ccccc32)cc1)c1ccc(N2c3ccccc3N(c3ccccc3)c3ccccc32)cc1]

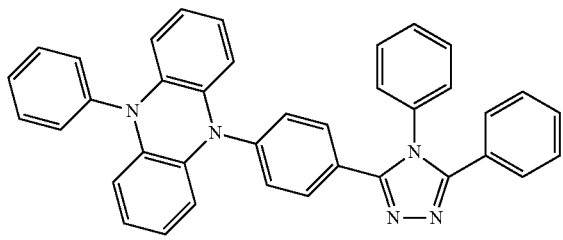 [SMILES: c1ccc(-c2nnc(-c3ccc(N4c5ccccc5N(c5ccccc5)c5ccccc54)cc3)n2-c2ccccc2)cc1]
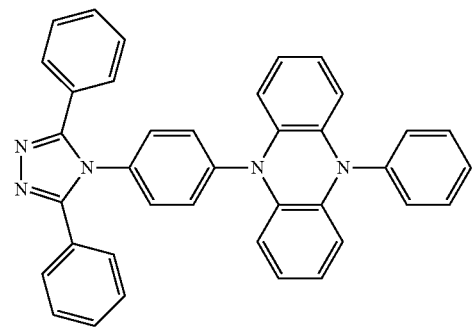 [SMILES: c1ccc(-c2nnc(-c3ccccc3)n2-c2ccc(N3c4ccccc4N(c4ccccc4)c4ccccc43)cc2)cc1]
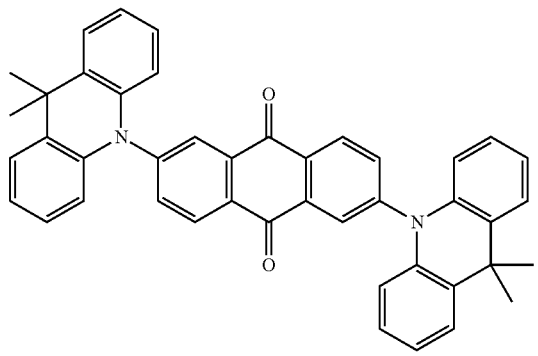 [SMILES: CC1(C)c2ccccc2N(c2ccc3c(c2)C(=O)c2ccc(N4c5ccccc5C(C)(C)c5ccccc54)cc2C3=O)c2ccccc21]
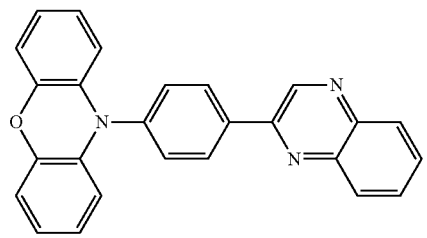 [SMILES: c1ccc2c(c1)Oc1ccccc1N2c1ccc(-c2cnc3ccccc3n2)cc1]
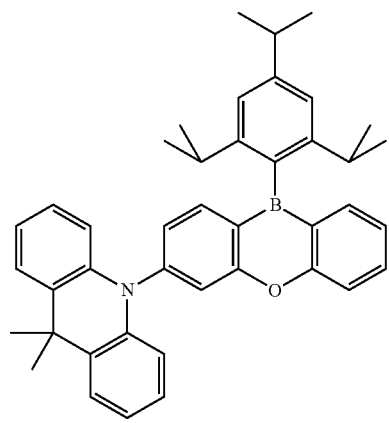 [SMILES: CC(C)c1cc(C(C)C)c(B2c3ccccc3Oc3cc(N4c5ccccc5C(C)(C)c5ccccc54)ccc32)c(C(C)C)c1]

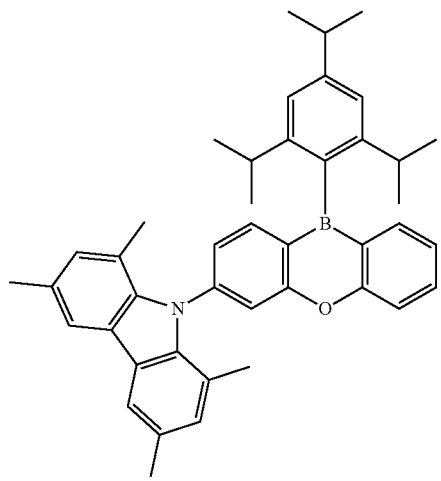 [SMILES: Cc1cc(C)c2c(c1)c1cc(C)cc(C)c1n2-c1ccc2c(c1)Oc1ccccc1B2c1c(C(C)C)cc(C(C)C)cc1C(C)C]
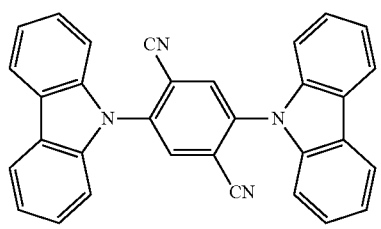 [SMILES: N#Cc1cc(-n2c3ccccc3c3ccccc32)c(C#N)cc1-n1c2ccccc2c2ccccc21]
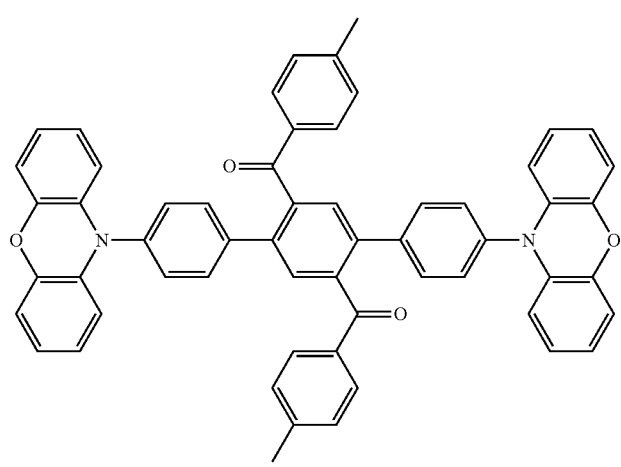 [SMILES: Cc1ccc(C(=O)c2cc(-c3ccc(N4c5ccccc5Oc5ccccc54)cc3)c(C(=O)c3ccc(C)cc3)cc2-c2ccc(N3c4ccccc4Oc4ccccc43)cc2)cc1]
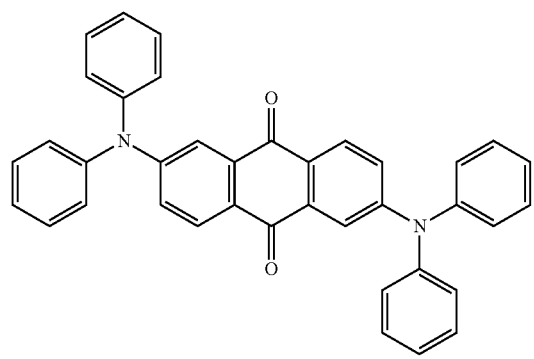 [SMILES: O=C1c2ccc(N(c3ccccc3)c3ccccc3)cc2C(=O)c2ccc(N(c3ccccc3)c3ccccc3)cc21]

-continued
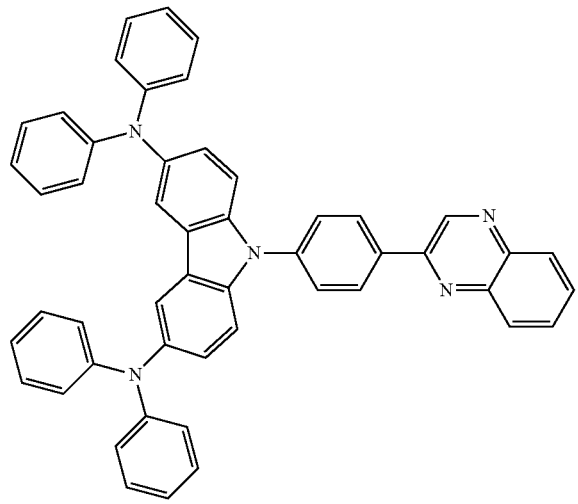 [SMILES: c1ccc(N(c2ccccc2)c2ccc3c(c2)c2cc(N(c4ccccc4)c4ccccc4)ccc2n3-c2ccc(-c3cnc4ccccc4n3)cc2)cc1]
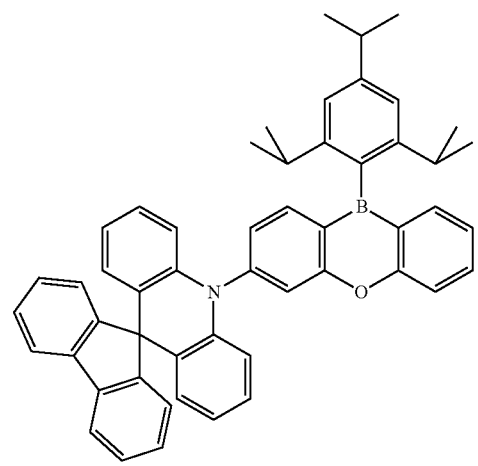 [SMILES: CC(C)c1cc(C(C)C)c(B2c3ccccc3Oc3cc(N4c5ccccc5C5(c6ccccc6-c6ccccc65)c5ccccc54)ccc32)c(C(C)C)c1]
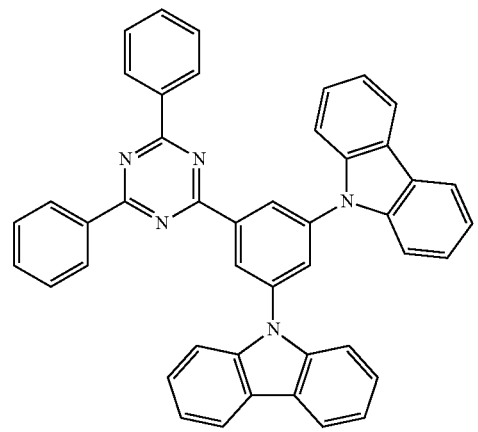 [SMILES: c1ccc(-c2nc(-c3ccccc3)nc(-c3cc(-n4c5ccccc5c5ccccc54)cc(-n4c5ccccc5c5ccccc54)c3)n2)cc1]
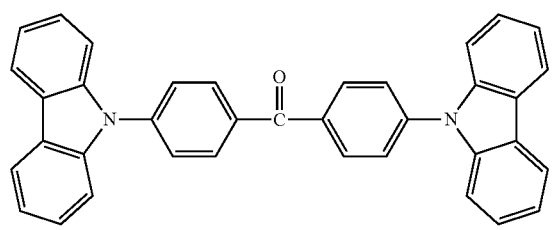 [SMILES: O=C(c1ccc(-n2c3ccccc3c3ccccc32)cc1)c1ccc(-n2c3ccccc3c3ccccc32)cc1]

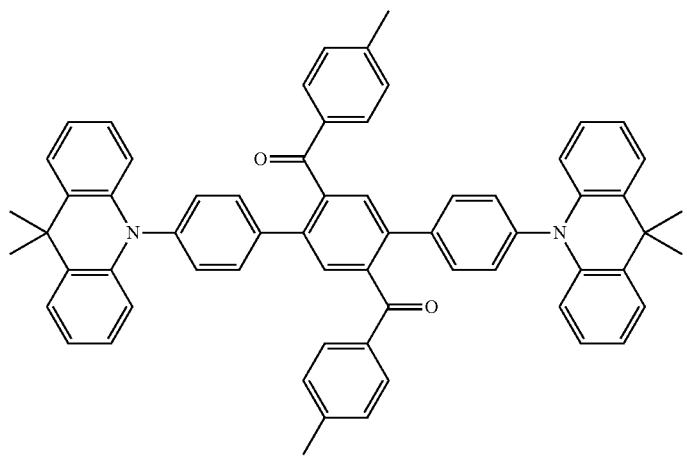
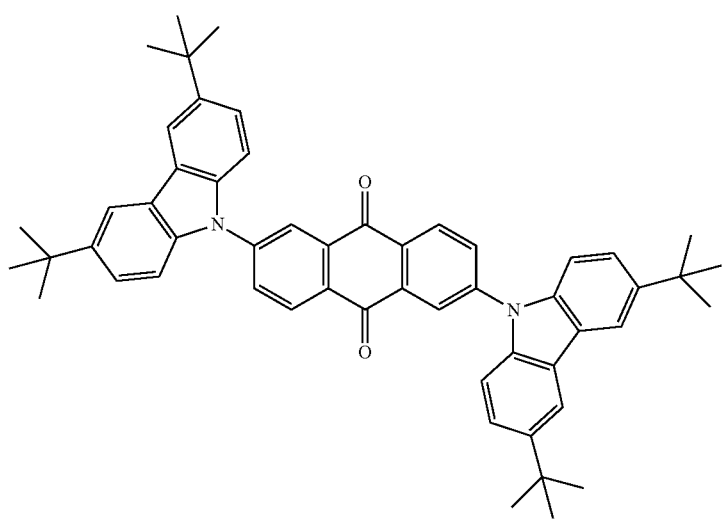 [SMILES: CC(C)(C)c1ccc2c(c1)c1cc(C(C)(C)C)ccc1n2-c1ccc2c(c1)C(=O)c1ccc(-n3c4ccc(C(C)(C)C)cc4c4cc(C(C)(C)C)ccc43)cc1C2=O]
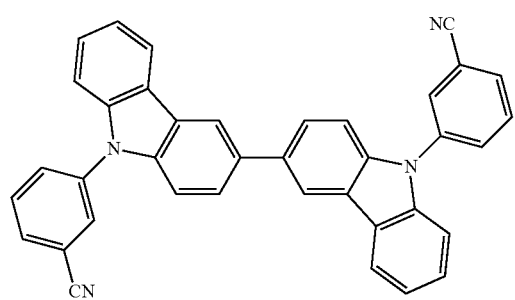 [SMILES: N#Cc1cccc(-n2c3ccccc3c3cc(-c4ccc5c(c4)c4ccccc4n5-c4cccc(C#N)c4)ccc32)c1]

-continued
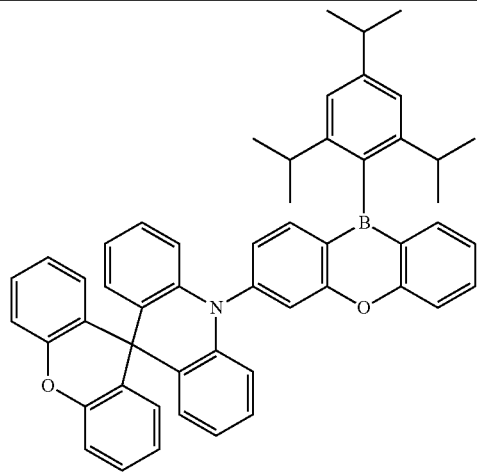
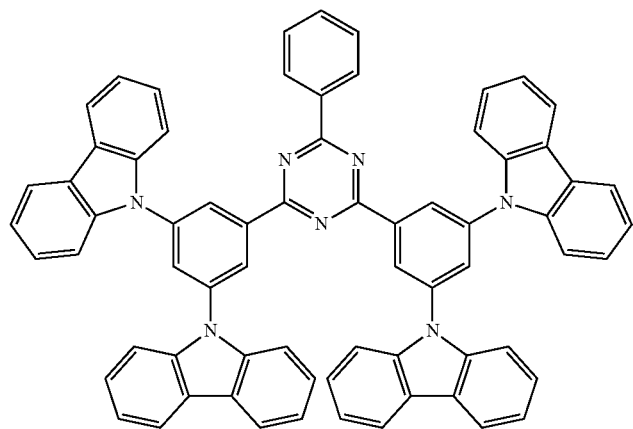 [SMILES: c1ccc(-c2nc(-c3cc(-n4c5ccccc5c5ccccc54)cc(-n4c5ccccc5c5ccccc54)c3)nc(-c3cc(-n4c5ccccc5c5ccccc54)cc(-n4c5ccccc5c5ccccc54)c3)n2)cc1]
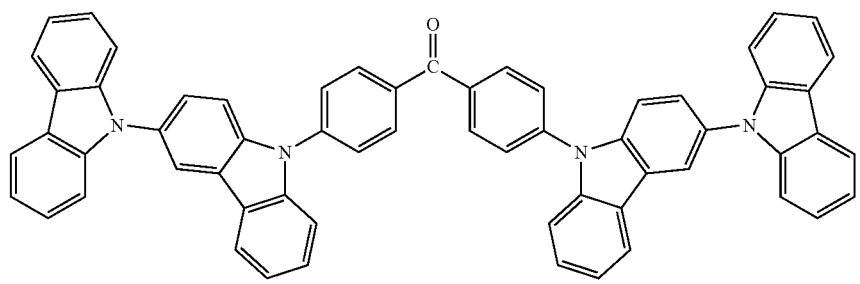 [SMILES: O=C(c1ccc(-n2c3ccccc3c3cc(-n4c5ccccc5c5ccccc54)ccc32)cc1)c1ccc(-n2c3ccccc3c3cc(-n4c5ccccc5c5ccccc54)ccc32)cc1]
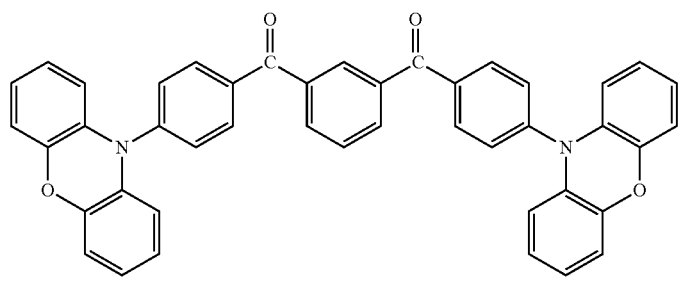 [SMILES: O=C(c1ccc(N2c3ccccc3Oc3ccccc32)cc1)c1cccc(C(=O)c2ccc(N3c4ccccc4Oc4ccccc43)cc2)c1]

-continued
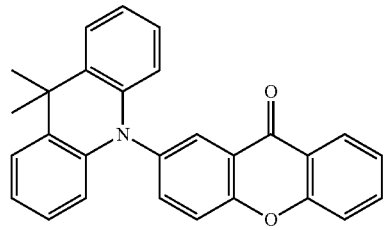 [SMILES: CC1(C)c2ccccc2N(c2ccc3oc4ccccc4c(=O)c3c2)c2ccccc21]
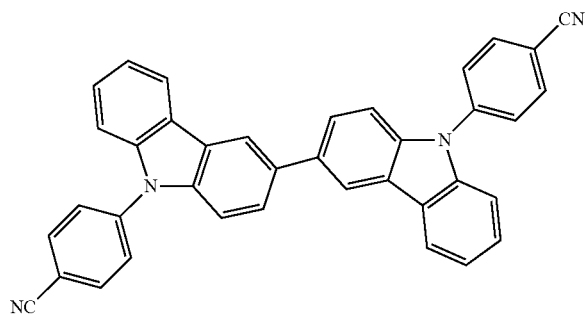 [SMILES: N#Cc1ccc(-n2c3ccccc3c3cc(-c4ccc5c(c4)c4ccccc4n5-c4ccc(C#N)cc4)ccc32)cc1]
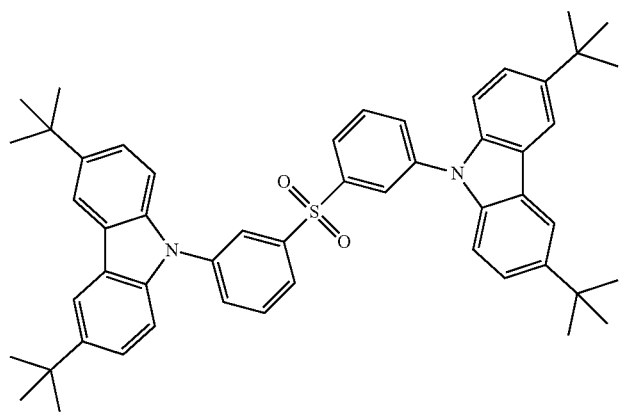 [SMILES: CC(C)(C)c1ccc2c(c1)c1cc(C(C)(C)C)ccc1n2-c1cccc(S(=O)(=O)c2cccc(-n3c4ccc(C(C)(C)C)cc4c4cc(C(C)(C)C)ccc43)c2)c1]
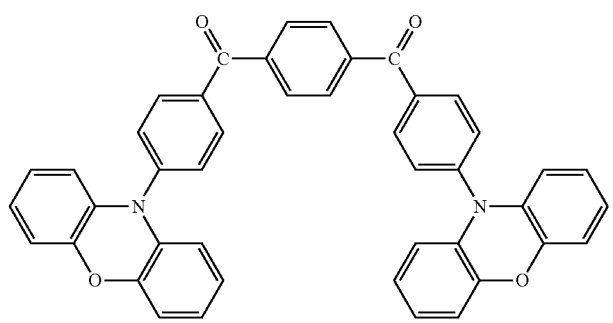 [SMILES: O=C(c1ccc(C(=O)c2ccc(N3c4ccccc4Oc4ccccc43)cc2)cc1)c1ccc(N2c3ccccc3Oc3ccccc32)cc1]
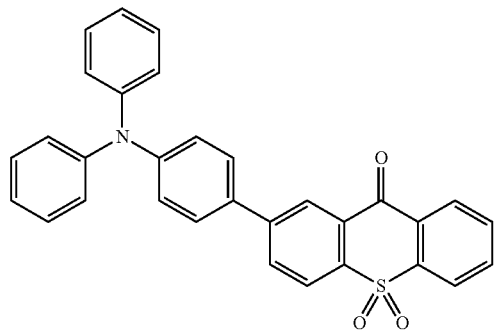 [SMILES: O=C1c2ccccc2S(=O)(=O)c2ccc(-c3ccc(N(c4ccccc4)c4ccccc4)cc3)cc21]

-continued
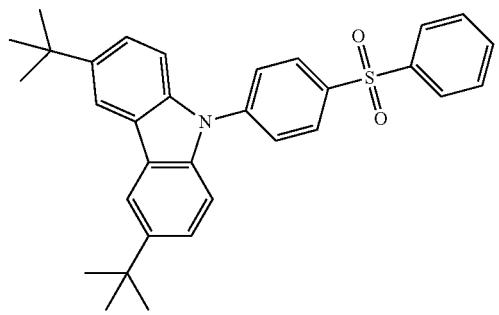 [SMILES: CC(C)(C)c1ccc2c(c1)c1cc(C(C)(C)C)ccc1n2-c1ccc(S(=O)(=O)c2ccccc2)cc1]
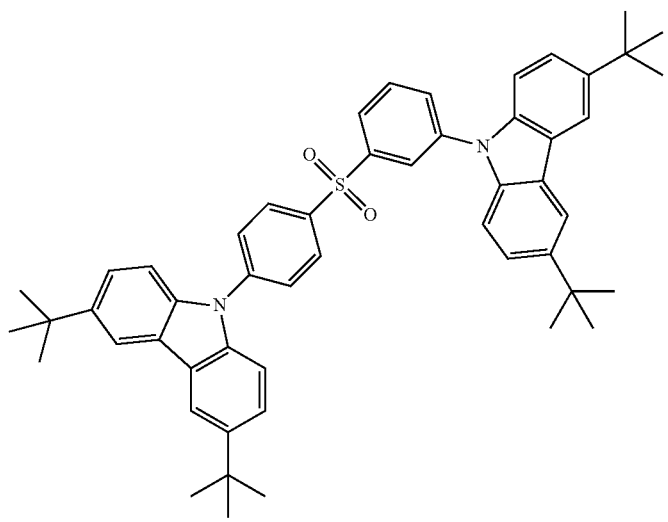 [SMILES: CC(C)(C)c1ccc2c(c1)c1cc(C(C)(C)C)ccc1n2-c1ccc(S(=O)(=O)c2cccc(-n3c4ccc(C(C)(C)C)cc4c4cc(C(C)(C)C)ccc43)c2)cc1]
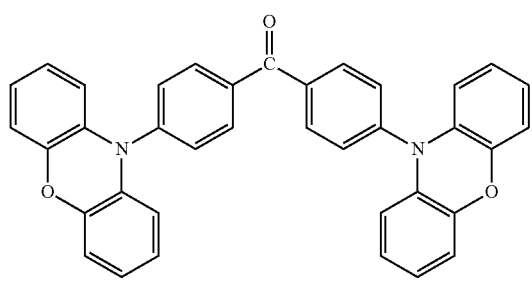 [SMILES: O=C(c1ccc(N2c3ccccc3Oc3ccccc32)cc1)c1ccc(N2c3ccccc3Oc3ccccc32)cc1]
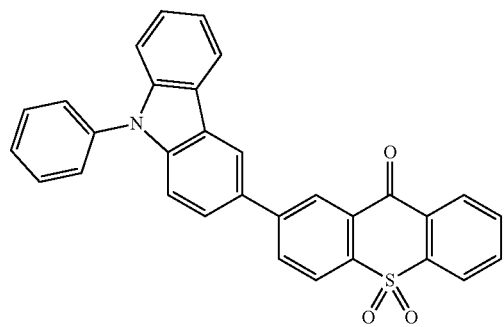 [SMILES: O=C1c2ccccc2S(=O)(=O)c2ccc(-c3ccc4c(c3)c3ccccc3n4-c3ccccc3)cc21]

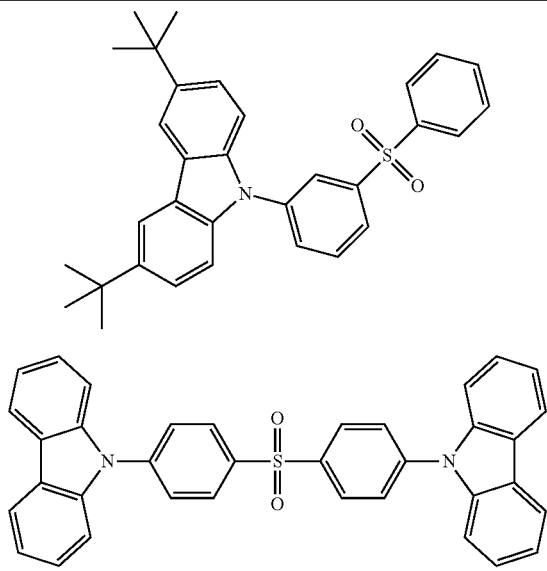

In an embodiment, the above organic compound is used for printing OLEDs, and has a molecular weight greater than or equal to 700 g/mol. In an embodiment, the organic compound has a molecular weight greater than or equal to 800 g/mol. In an embodiment, the organic compound has a molecular weight greater than or equal to 900 g/mol. In an embodiment, the organic compound has a molecular weight greater than or equal to 1,000 g/mol. In an embodiment, the organic compound has a molecular weight greater than or equal to 1,100 g/mol.

In an embodiment, the above organic compound is used in an evaporated OLED, and has a molecular weight less than or equal to 1,100 g/mol. In an embodiment, the organic compound has a molecular weight less than or equal to 1,000 g/mol. In an embodiment, the organic compound has a molecular weight less than or equal to 900 g/mol. In an embodiment, the organic compound has a molecular weight less than or equal to 800 g/mol. In an embodiment, the organic compound has a molecular weight less than or equal to 750 g/mol.

In an embodiment, the solubility of the organic compound in toluene is greater than or equal to 10 mg/ml at 25° C. In an embodiment, the solubility of the organic compound in toluene is greater than or equal to 15 mg/ml. In an embodiment, the solubility of the organic compound in toluene is greater than or equal to 20 mg/ml.

The application of the above organic mixture in an organic electronic device is provided.

The organic mixture in another embodiment includes the above-mentioned polymer, and the various components and contents of the organic mixture are the same as those of the organic mixture in the above embodiments, and will not be described herein again.

The formulation in an embodiment comprises an organic solvent and the above organic compound or polymer. In this embodiment, the formulation is an ink. The viscosity and surface tension of ink are important parameters when the formulation is used in the printing process. The suitable surface tension parameters of ink are suitable for a particular substrate and a particular printing method.

In an embodiment, the ink has a surface tension within a range of 19 dyne/cm to 50 dyne/cm at the operating temperature or at 25° C. In an embodiment, the ink has a surface tension within a range of 22 dyne/cm to 35 dyne/cm at the operating temperature or at 25° C. In an embodiment, the ink has a surface tension within a range of 25 dyne/cm to 33 dyne/cm at the operating temperature or at 25° C.

In an embodiment, the ink has a viscosity within a range of 1 cps to 100 cps at the operating temperature or at 25° C. In an embodiment, the ink has a viscosity within a range of 1 cps to 50 cps at the operating temperature or at 25° C. In an embodiment, the ink has a viscosity at the operating temperature or at 25° C. In an embodiment, the ink has a viscosity within a range of 1.5 cps to 20 cps at the operating temperature or at 25° C. In an embodiment, the ink has a viscosity within a range of 4.0 cps to 20 cps at the operating temperature or at 25° C. The formulation thus formulated will be suitable for inkjet printing.

The viscosity can be adjusted by different methods, such as by selecting a suitable solvent and a concentration of the functional material in the ink. An ink containing a metal organic complex or a polymer can facilitate the adjustment of the printing ink in an appropriate range according to the printing method used. The organic functional material is contained in the formulation in a weight ratio of 0.3 wt % to 30 wt %. In an embodiment, the organic functional material is contained in the formulation in a weight ratio of 0.5 wt % to 20 wt %. In an embodiment, the organic functional material is contained in the formulation in a weight ratio of 0.5 wt % to 15 wt %. In an embodiment, the organic functional material is contained in the formulation in a weight ratio of 0.5 wt % to 10 wt %. In an embodiment, the organic functional material is contained in the formulation in a weight ratio of 1 wt % to 5 wt %.

In an embodiment, the organic solvent comprises a first solvent selected from aromatic and/or heteroaromatic solvents. Further, the first solvent may be an aliphatic chain/ring substituted aromatic solvent, an aromatic ketone solvent, or an aromatic ether solvent.

Examples of the first solvent include, but are not limited to, solvents based on aromatics or heteroaromatics, such as p-diisopropylbenzene, pentylbenzene, tetrahydronaphthalene, cyclohexyl benzene, chloronaphthalene, 1,4-dimethylnaphthalene, 3-isopropylbiphenyl, p-cymene, dipentylbenzene, tripentylbenzene, pentyltoluene, o-xylene, m-xylene, p-xylene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, 1-methoxynaphthalene, cyclohexylbenzene, dimethylnaphthalene, 3-isopropylbiphenyl, p-cymene, 1-methylnaphthalene, 1,2,4-trichlorobenzene, 1,3-dipropoxybenzene, 4,4-difluorodiphenylmethane, 1,2-dimethoxy-4-(1-propenyl)benzene, diphenylmethane, 2-phenylpyridine, 3-phenylpyridine, N-methyldiphenylamine 4-isopropylbiphenyl, α,α-dichlorodiphenylmethane, 4-(3-phenylpropyl)pyridine, benzylbenzoate, 1,1-di(3,4-dimethylphenyl)ethane, 2-isopropylnaphthalene, dibenzylether, and the like; solvents based on ketones: 1-tetralone, 2-tetralone, 2-(phenylepoxy)tetralone, 6-(methoxyl)tetralone, acetophenone, phenylacetone, benzophenone, and derivatives thereof, such as 4-methylacetophenone, 3-methylacetophenone, 2-methylacetophenone, 4-methylphenylacetone, 3-methylphenylacetone, 2-methylphenylacetone, isophorone, 2,6,8-trimethyl-4-nonanone, fenchone, 2-nonanone, 3-nonanone, 5-nonanone, 2-demayone, 2,5-hexanedione, phorone, di-n-amyl ketone; aromatic ether solvents: 3-phenoxytoluene, butoxybenzene, benzylbutylbenzene, p-anisaldehyde dimethyl acetal, tetrahydro-2-phenoxy-2H-pyran, 1,2-dimethoxy 4-(1-propenyl)benzene, 1,4-benzodioxane, 1,3-dipropylbenzene, 2,5-dimethoxytoluene, 4-ethylphenetole, 1,2,4-trimethoxybenzene, 4-(1-propenyl)-1,2-dimethoxybenzene, 1,3-dimethoxybenzene, glycidyl phenyl ether, dibenzyl ether, 4-tert-butylanisole, trans-p-propenylanisole, 1,2-dimethoxybenzene, 1-methoxynaphthalene, diphenyl ether, 2-phenoxymethyl ether, 2-phenoxytetrahydrofuran, ethyl-2-naphthyl ether, pentyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether; and ester solvents: alkyl octoate, alkyl sebacate, alkyl stearate, alkyl benzoate, alkyl phenylacetate, alkyl cinnamate, alkyl oxalate, alkyl maleate, alkyl lactone, alkyl oleate, and the like.

Further, the first organic solvent may also be one or more solvents selected from aliphatic ketones, such as 2-nonanone, 3-nonanone, 5-nonanone, 2-decanone, 2,5-hexanedione, 2,6,8-trimethyl-4-demayone, phorone, di-n-pentyl ketone, and the like; or aliphatic ethers, such as amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethyl ether alcohol ethyl methyl ether, triethylene glycol butyl methyl ether, tripropylene glycol dimethyl ether, tetraethylene glycol dimethyl ether, and the like.

In an embodiment, the organic solvent further includes a second organic solvent, and the second organic solvent is one or more solvents selected from methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxy toluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin, indene, and/or mixtures thereof.

In an embodiment, the formulation can be a solution or suspension, depending on the compatibility between the organic mixture and the organic solvent.

In an embodiment, the organic compound in the formulation is present in a weight percentage of 0.01 wt % to 20 wt %. In an embodiment, the organic compound in the formulation is present in a weight percentage of 0.1 wt % to 15 wt %. In an embodiment, the organic compound in the formulation is present in a weight percentage of 0.2 wt % to 10 wt %. In an embodiment, the organic compound in the formulation in a weight percentage of 0.25 wt % to 5 wt %.

In an embodiment, the application of the above formulation in preparing an organic electronic device is provided, in particular the application of the above formulation as a coating or printing ink in preparing an organic electronic device, particularly by a printing method or a coating method.

The appropriate printing technology or coating technology includes, but is not limited to inkjet printing, nozzle printing, typography, screen printing, dip coating, spin coating, blade coating, roller printing, twist roller printing, lithography, flexography, rotary printing, spray coating, brush coating or transfer printing, slot die coating, and the like, especially gravure printing, nozzle printing and inkjet printing. The formulation may further includes one or more component, for example, selected from of a surfactant compound, a lubricant, a wetting agent, a dispersant, a hydrophobic agent and a binder, to adjust the viscosity and the film forming property and to improve the adhesion property. The detailed information relevant to the printing technology and requirements of the printing technology to the solution, such as solvent, concentration, and viscosity, may be referred to Handbook of Print Media: Technologies and Production Methods, Helmut Kipphan, ISBN 3-540-67326-1.

In an embodiment, the application of the above organic compound or polymer in an organic electronic device is an application of the organic compound or polymer in an organic electronic device. The organic electronic devices can be selected from the group consisting of an organic light-emitting diode (OLED), an organic photovoltaic cell (OPV), an organic light-emitting electrochemical cell (OLEEC), an organic field effect transistor (OFET), an organic light-emitting field effect transistor, an organic laser, an organic spintronic device, an organic sensor, and an organic plasmon emitting diode. In an embodiment, the organic electronic device is an electroluminescent device such as an OLED, an OLEEC and an organic light-emitting field effect transistor. Further, the organic compound is used in a light-emitting layer of the electroluminescent device.

The organic electronic device in an embodiment includes at least one organic compound or organic mixture as described above. The organic electronic device may include a cathode, an anode and a functional layer between the cathode and the anode, and the functional layer includes the aforementioned organic mixture. Specifically, the organic electronic device comprises at least a cathode, an anode and a functional layer between the cathode and the anode, the functional layer comprising at least one organic compound or polymer as described above or being prepared from the above formulation. The functional layer is one or more selected from a hole injection layer, a hole transport layer, a hole blocking layer, an electron injection layer, an electron transport layer, an electron blocking layer and a light-emitting layer.

The organic electronic devices can be selected from the group consisting of an organic light-emitting diode (OLED), an organic photovoltaic cell (OPV), an organic light-emitting electrochemical cell (OLEEC), an organic field effect transistor (OFET), an organic light-emitting field effect transistor, an organic laser, an organic spintronic device, an organic sensor, and an organic plasmon emitting diode. In an embodiment, the organic electronic device is an organic electroluminescent device such as an OLED, an OLEEC or an organic light-emitting field effect transistor. Further, the organic light-emitting diode may be an evaporated organic light-emitting diode or a printed organic light-emitting diode.

In an embodiment, the light-emitting layer of the organic electroluminescent device, especially the organic light-emitting diode comprises one of the above organic compounds or polymers. Further, in an embodiment, the light-emitting layer further comprises a light emitting material and/or a host material. In an embodiment, the light emitting material is a phosphorescent or fluorescent emitter. That is, the organic light-emitting diode comprises the organic compound or polymer as mentioned above and a phosphorescent emitter. The organic light-emitting diode may also comprise the organic compound or polymer as mentioned above and a host material. Further, the organic light-emitting diode may also comprise the organic compound or polymer as mentioned above, a phosphorescent emitter, and a host material.

In an embodiment, the organic electroluminescent device includes a substrate, an anode, a light-emitting layer and a cathode which are sequentially stacked. The light-emitting layer has at least one layer. It should be noted that the organic electroluminescent device may be an organic light-emitting diode.

The substrate may be opaque or transparent. A transparent substrate may be used to make transparent light-emitting device, which may be referred to Bulovic et al. Nature 1996, 380, p 29 and Gu et al. Appl. Phys. Lett. 1996, 68, p 2606. The substrate may be rigid or flexible. The substrate may be plastic, metal, semiconductor wafer or glass. In one embodiment, the substrate has a smooth surface. The substrate free of any surface defects is particular desirable. In an embodiment, the substrate is flexible and may be selected from a polymer thin film or plastic which has a glass transition temperature Tg greater than 150° C. The flexible substrate may be poly(ethylene terephthalate) (PET) or polyethylene glycol (2,6-naphthalene) (PEN). In an embodiment, the glass transition temperature Tg of the substrate is greater than 200° C. In an embodiment, the glass transition temperature Tg of the substrate is greater than 250° C. In an embodiment, the glass transition temperature Tg of the substrate is greater than 300° C.

The anode may include a conductive metal or a metal oxide, or a conductive polymer. The anode may easily inject holes into the hole injection layer (HIL) or the hole transport layer (HTL) or the light-emitting layer. In one embodiment, the absolute value of the difference between the work function of the anode and the HOMO energy level or the valence band energy level of the emitter in the light-emitting layer or of the p-type semiconductor material as the HIL or HTL or the electron blocking layer (EBL) is less than 0.5 eV. In one embodiment, the absolute value of the difference between the work function of the anode and the HOMO energy level or the valence band energy level of the emitter in the light-emitting layer or of the p-type semiconductor material as the HIL or HTL or the electron blocking layer (EBL) is less than 0.3 eV. In one embodiment, the absolute value of the difference between the work function of the anode and the HOMO energy level or the valence band energy level of the emitter in the light-emitting layer or of the p-type semiconductor material as the HIL or HTL or the electron blocking layer (EBL) is less than 0.2 eV. Examples of anode materials include, but are not limited to, Al, Cu, Au, Ag, Mg, Fe, Co, Ni, Mn, Pd, Pt, ITO, aluminum-doped zinc oxide (AZO), and the like. Other materials may also be used as the anode material. The anode material can be deposited using any suitable technique, such as a suitable physical vapor deposition method, including radio frequency magnetron sputtering, vacuum thermal evaporation, electron beam (e-beam), and the like. In other embodiments, the anode is patterned. The patterned ITO conductive substrate is commercially available and can be used to fabricate the device according to the present embodiment.

The cathode may include a conductive metal or a metal oxide. The cathode can easily inject electrons into the EIL or ETL or directly into the light-emitting layer. In an embodiment, the absolute value of the difference between the work function of the cathode and the LUMO energy level or the conduction band energy level of the emitter in the light-emitting layer or of the n-type semiconductor material as the electron injection layer (EIL) or the electron transport layer (ETL) or the hole blocking layer (HBL) is less than 0.5 eV. In one embodiment, the absolute value of the difference between the work function of the cathode and the LUMO energy level or the conduction band energy level of the emitter in the light-emitting layer or of the n-type semiconductor material as the electron injection layer (EIL) or the electron transport layer (ETL) or the hole blocking layer (HBL) is less than 0.3 eV. In one embodiment, the absolute value of the difference between the work function of the cathode and the LUMO energy level or the conduction band energy level of the emitter in the light-emitting layer or of the n-type semiconductor material as the electron injection layer (EIL) or the electron transport layer (ETL) or the hole blocking layer (HBL) is less than 0.2 eV. All the materials that can be used as the cathode of the OLED can serve as a cathode material of the organic electronic device according to the present embodiment. Examples of the cathode material include, but are not limited to, Al, Au, Ag, Ca, Ba, Mg, LiF/Al, MgAg alloy, $BaF_2$/Al, Cu, Fe, Co, Ni, Mn, Pd, Pt, ITO, and the like. The cathode material can be deposited using any suitable technique, such as a suitable physical vapor deposition method, including radio frequency magnetron sputtering, vacuum thermal evaporation, electron beam (e-beam), and the like.

The OLED may further include other functional layers such as a hole injection layer (HIL), a hole transport layer (HTL), an electron blocking layer (EBL), an electron injection layer (EIL), an electron transport layer (ETL) or a hole blocking layer (HBL). Materials suitable for use in these functional layers are described in detail above and in WO2010135519A1, US20090134784A1 and WO2011110277A1, the entire contents of which are hereby incorporated herein by reference.

In an embodiment, the light-emitting layer of the organic electroluminescent device is prepared with the above formulation.

In an embodiment, the organic electroluminescent device has a light emission wavelength between 300 and 1000 nm. In an embodiment, the light emission wavelength of the organic electroluminescent device is between 350 and 900 nm. In an embodiment, the light emission wavelength of the organic electroluminescent device is between 400 and 800 nm.

In an embodiment, the aforementioned organic electronic device is applied in an electronic device. The electronic device is selected from display devices, lighting devices, light sources, or sensors. The organic electronic device may be an organic electroluminescent device.

An electronic device comprises the aforementioned organic electronic device.

The disclosure will be described with reference to the preferred embodiments, but the disclosure is not to be construed as being limited to the following examples. It is to be understood that the appended claims are intended to cover the scope of the disclosure. Those skilled in the art will understand that modifications can be made to various embodiments of the disclosure with the teaching of the present disclosure, which will be covered by the spirit and scope of the claims of the disclosure.

Example 1

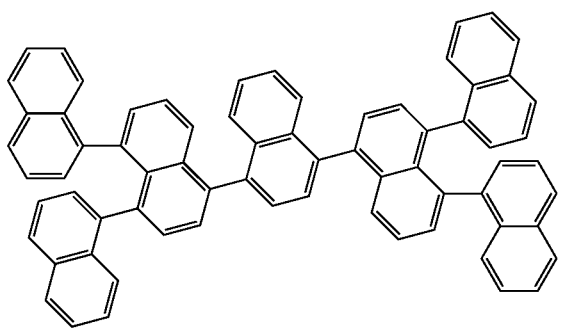

(1)

5''',8'-bis(naphthalen-1-yl)-1,1':4',1'':5'',1''':4'''',1''''-pentanaphthyl naphthalene 2.9 g of 10 mmol 1,4-dibromonaphthalene, 9.3 g of 22 mmol [1,1':8',1''-trinaphthyl]-4'-yl boric acid, 6.9 g of 50 mmol potassium carbonate, 1.15 g of 1 mmol Pd(PPh$_3$)$_4$, 100 ml of toluene, 25 ml of water and 25 ml of ethanol were added to a 250 ml three-necked flask under a N$_2$ atmosphere, and reacted at 110° C. The reaction progress was monitored by TLC, and when the reaction completed and the reaction solution was cooled to room temperature, the reaction solution was poured into and washed with water for the removal of K$_2$CO$_3$ and then suction filtered to obtain a solid product. The solid product was then washed with dichloromethane and recrystallized from dichloromethane/ethanol to get 7.0 g of the product 5''',8'-bis(naphthalen-1-yl)-1,1':4',1'':5'',1''':4'''',1''''-pentanaphthyl naphthalene as a white solid powder. MS (ASAP)=884.4.

Example 2

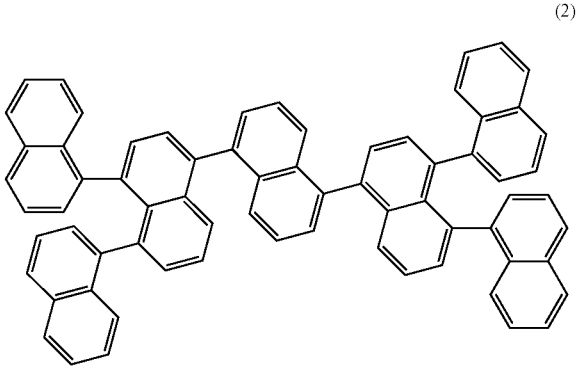 [SMILES: c1ccc2c(-c3cccc4c(-c5cccc6c(-c7ccc(-c8cccc9ccccc89)c8c(-c9cccc%10ccccc9%10)cccc78)cccc56)ccc(-c5cccc6ccccc56)c34)cccc2c1]

(2)

5''',8'-bis(naphthalen-1-yl)-1,1':4',1'':5'',1''':4'''',1''''-pentanaphthyl naphthalene 2.9 g of 10 mmol 1,5-dibromonaphthalene, 9.3 g of 22 mmol [1,1':8',1''-trinaphthyl]-4'-yl boric acid, 6.9 g of 50 mmol potassium carbonate, 1.15 g of 1 mmol Pd(PPh$_3$)$_4$, 100 ml of toluene, 25 ml of water and 25 ml of ethanol were added to a 250ml three-necked flask under a N$_2$ atmosphere, and reacted at 110° C. The reaction progress was monitored by TLC, and when the reaction completed and the reaction solution was cooled to room temperature, the reaction solution was poured into and washed with water for the removal of K$_2$CO$_3$ and then suction filtered to get a solid product. The solid product was washed with dichloromethane and recrystallized from a mixed toluene/methanol solvent to get the product 5''',8'-bis(naphthalen-1-yl)-1,1':4',1'':5'',1''':4'''',1''''-pentanaphthyl naphthalene as a white solid powder. MS (ASAP)=884.2.

Example 3

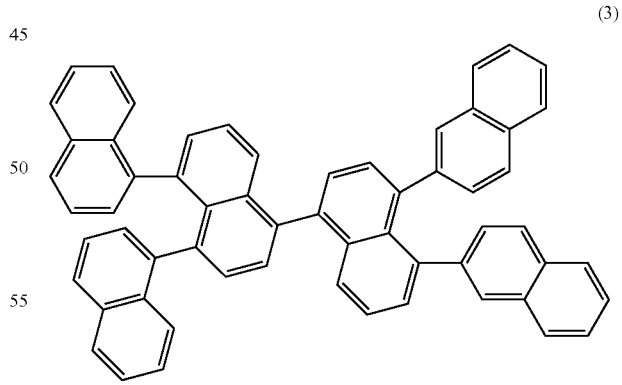

(3)

8'-bis(naphthalen-1-yl)-5''(naphthalen-2-yl)-1,1':4', 1'':4'',2'''-tetranaphthyl naphthalene 4.58 g of 10 mmol 4'-bromo-1,1':8',1''-dinaphthyl naphthalene, 4.66 g of 11 mmol [2,1':8',2''-dinaphthyl]-4'-yl naphthyl boronic acid, 3.45 g of 25 mmol potassium carbonate, 1.15 g of 1 mmol Pd(PPh$_3$)$_4$, 100 ml of toluene, 25 ml of water and 25 ml of ethanol were added to a 250 ml three-necked flask under a $N_2$ atmosphere, and reacted at 110° C. The reaction progress was monitored by TLC, and when the reaction completed and the reaction solution was cooled to room temperature, the reaction solution was poured into and washed with water for the removal of $K_2CO_3$ and then suction filtered to get a solid product. The solid product was washed with dichloromethane and recrystallized from a mixed toluene/petroleum ether solvent to get the product 1,8-bis(4-(diphenylboryl-3',5'-dioxy))phenyl-9-methylcarbazole as a white solid powder. MS (ASAP)=758.4.

Example 4

(4)

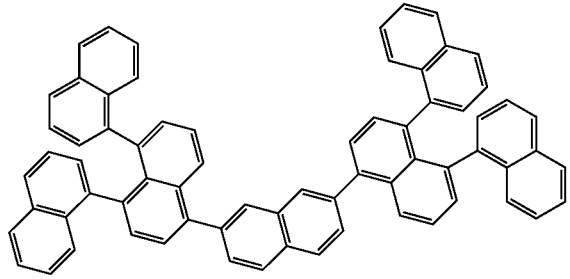

5''',8'-bis(naphthalen-1-yl)-1,1':4',1'':7'',2''':4''',1''''-pentanaphthyl naphthalene In this example, the final product 5''',8'-bis(naphthalen-1-yl)-1,1':4',1'':7'',2''':4''',1''''-pentanaphthyl naphthalene was synthesized in the same procedure with the reaction temperature and reaction time used in the reaction process as the product of Example 1 5''',8'-bis(naphthalen-1-yl)-1,1':4',1'':5'',1''':4''',1''''-pentanaphthyl naphthalene, except that the intermediate 1,4-dibromonaphthalene is replaced by 2,7-dibromonaphthalene. The final product 5''',8'-bis(naphthalen-1-yl)-1,1':4',1'':7'',2''':4''',1''''-pentanaphthyl naphthalene (4) was formed in a Suzuki reaction under of Pd(0) catalysis. MS (ASAP)=884.5.

Example 5

(5)

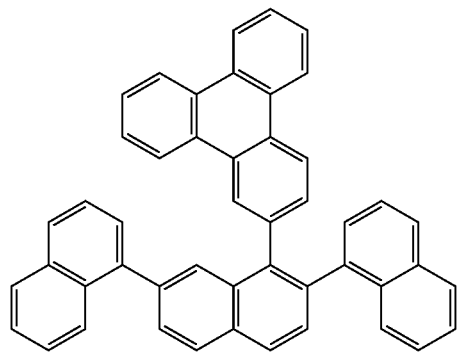

2-([1,2':7',1''-trinaphthyl]-1'-yl)triphenylene 4.58 g of 10 mmol 1'-bromo-1,2':7',1''-dinaphthyl naphthalene, 3.0 g of 11 mmol triphenylene-2-boronic acid, 3.45 g of 25 mmol potassium carbonate, 1.15 g of 1 mmol Pd(PPh$_3$)$_4$, 100 ml of toluene, 25 ml of water and 25 ml of ethanol were added to a 250 ml three-necked flask under a $N_2$ atmosphere, and reacted at 110° C. The reaction progress was monitored by TLC, and when the reaction completed and the reaction solution was cooled to room temperature, the reaction solution was poured into and washed with water for the removal of $K_2CO_3$ and then suction filtered to get a solid product. The solid product was washed with dichloromethane and recrystallized from a mixed toluene/ethanol solvent to get the product 2-([1,2':7',1''-trinaphthyl]-1'-yl) triphenylene (5) as a white solid powder. MS (ASAP)=606.4.

The energy level of the organic material can be calculated by quantum computation, for example, using TD-DFT (time-dependent density functional theory) by Gaussian09W (Gaussian Inc.), the specific simulation methods of which can be found in WO2011141110. Firstly, the molecular geometry is optimized by semi-empirical method "Ground State/Semi-empirical/Default Spin/AM1" (Charge 0/Spin Singlet), and then the energy structure of organic molecules is calculated by TD-DFT (time-density functional theory) "TD-SCF/DFT/Default Spin/B3PW91" and the basis set "6-31G (d)" (Charge 0/Spin Singlet). The HOMO and LUMO levels are calculated using the following calibration formula, wherein $S_1$, $T_1$, and resonance factor $f(S_1)$ are used directly.

$$HOMO(eV)=((HOMO(G)\times 27.212)-0.9899)/1.1206$$

$$LUMO(eV)=((LUMO(G)\times 27.212)-2.0041)/1.385$$

wherein HOMO (G) and LUMO (G) are the direct calculation results of Gaussian 09W, in units of Hartree. The results are shown in Table 1:

TABLE I

| material | HOMO [eV] | LUMO [eV] | f ($S_1$) | $T_1$ [eV] | $S_1$ [eV] | $\Delta E_{ST}$ |
|---|---|---|---|---|---|---|
| (1) | −5.66 | −2.47 | 0.063 | 2.39 | 2.49 | 0.10 |
| (2) | −5.67 | −2.47 | 0.054 | 2.40 | 2.60 | 0.20 |
| (3) | −5.68 | −2.46 | 0.045 | 2.40 | 2.65 | 0.25 |
| (4) | −5.65 | −2.55 | 0.088 | 2.38 | 2.49 | 0.11 |
| (5) | −5.87 | −2.46 | 0.043 | 2.51 | 2.77 | 0.25 |

The respective resonant factor $f(S_1)$ is in a range of 0.043 to 0.088, and the fluorescence quantum luminescence efficiency of the materials can be improved effectively. Meanwhile, the value of $\Delta E(S_1-T_1)$ is no higher than 0.25 eV, which satisfies the conditions of less than 0.30 eV for delayed fluorescent emission.

As a comparison with the above-mentioned fluorescent emitter materials, the delayed fluorescent emitter material of the D-A system is denoted by Ref 1:

Ref1

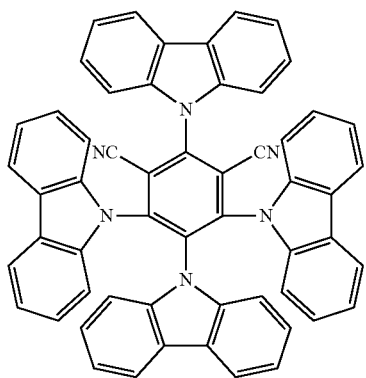

Preparation of OLED Devices:

The preparation steps of OLED devices with ITO/NPD (35 nm)/5%(1)~(5):mCP(15 nm)/TPBi(65 nm)/LiF (1 nm)/Al (150 nm)/cathode are as follows:

a, cleaning the conductive glass substrate: when used for the first time, washing with various solvents, such as chloroform, ketone or isopropyl alcohol, and then treating with ultraviolet ozone plasma;

b. HTL(35 nm), EML(15 nm), and ETL(65 nm): thermal evaporation deposition in high vacuum ($1 \times 10^{-6}$ mbar);

c, cathode: thermal evaporation deposition in high vacuum ($1 \times 10^{-6}$ mbar) with LiF/Al (1 nm/150 nm);

d, encapsulating: encapsulating the device in a nitrogen glove box with UV curable resin.

The current-voltage (J-V) characteristics of each OLED device are characterized by characterization equipment, while important parameters such as efficiency, lifetime and external quantum efficiency were recorded. It was determined that the luminous efficiency and lifetime of OLED1 (corresponding to raw material (1)) were both 3 times or above of that of OLED Ref1 (corresponding to raw material (Ref1)). The OLED3 (corresponding to raw material (3)) had a luminous efficiency 4 times of and a lifetime more than 6 times of those of OLED Ref1. Particularly, the OLED3 has a maximum external quantum efficiency up to 10% or above. It can be seen that the luminous efficiency and lifetime of the OLED device prepared by using the organic compound of the present disclosure is greatly improved.

What is claimed is:

1. An organic compound for an organic electronic device, wherein the organic compound is one selected from compounds represented by following structural formulas (2) to (16):

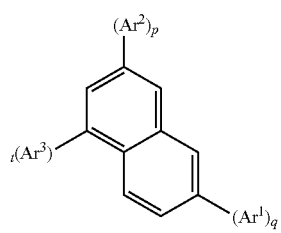

(2)

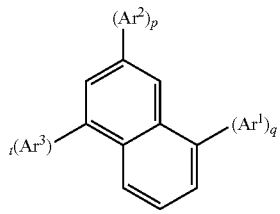

(3)

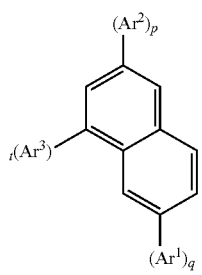

(4)

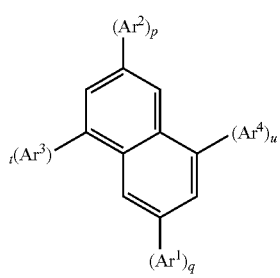

(5)

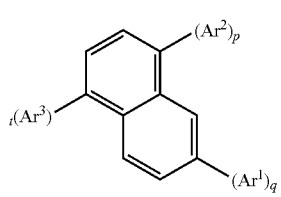

(6)

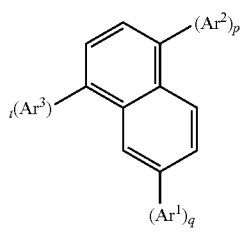

(7)

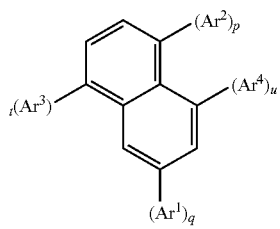

(8)

-continued

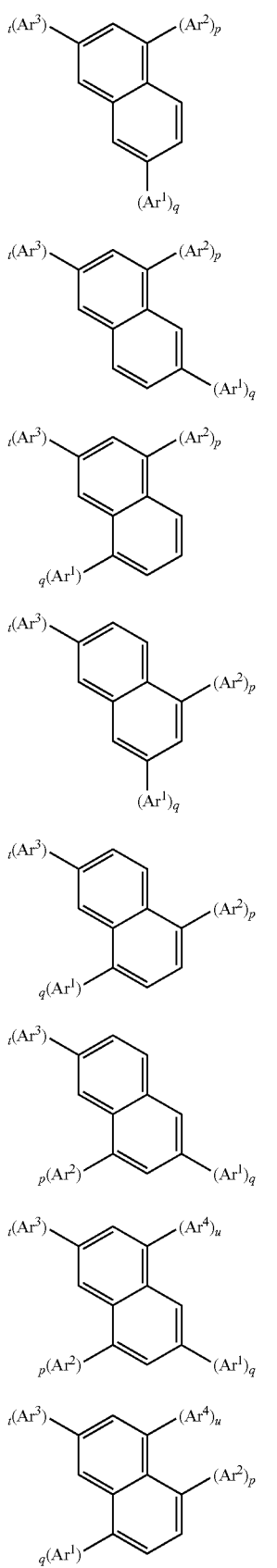

(9)

(10)

(11)

(12)

(13)

(14)

(15)

(16)

wherein p is selected from 0, 1, 2 or 3, q is selected from 0, 1, 2, 3 or 4, t is selected from 0, 1, 2, 3, 4 or 5, and p+t+q≥3 in formulas (2)-(4), (6), (7) or (9)-(14);

p is selected from 0, 1, 2 or 3, q is selected from 0, 1, 2, 3 or 4, t is selected from 0, 1, 2, 3, 4 or 5, p+t+q≥3, and u is selected from 0, 1, 2, 3, 4 or 5 in formulas (5), (15) or (16);

p is selected from 1, 2 or 3, q is selected from 0, 1, 2, 3 or 4, t is selected from 3, 4 or 5, p+t+q≥3, and u is selected from 1, 2, 3, 4 or 5 in formula (8);

$Ar^4$ is independently selected from naphthalene and derivatives thereof;

$Ar^1$, $Ar^2$ and $Ar^3$ are independently selected from:

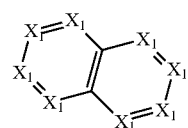

$X_1$ is selected from $CR^2$ or N;

$R^2$ is one or more groups independently selected from the group consisting of H, D, a linear alkyl group containing 1 to 20 C atoms, an linear alkoxy group containing 1 to 20 C atoms, a linear thioalkoxy group containing 1 to 20 C atoms, a branched or cyclic alkyl group containing 3 to 20 C atoms, a branched or cyclic alkoxy group containing 3 to 20 C atoms, a branched or cyclic thioalkoxy group containing 3 to 20 C atoms, a branched or cyclic silyl group containing 3 to 20 C atoms, a substituted ketone group containing 1 to 20 C atoms, an alkoxycarbonyl group containing 2 to 20 C atoms, an aryloxycarbonyl group containing 7 to 20 C atoms, a cyano group, a carbamoyl group, a haloformyl group, a formyl group, an isocyano group, an isocyanate group, a thiocyanate group, an isothiocyanate group, a hydroxyl group, a nitro group, a CF3 group, Cl, Br, F, a crosslinkable group, a substituted or unsubstituted aromatic ring system containing 5 to 40 ring atoms or substituted or unsubstituted heteroaromatic ring system containing 5 to 40 ring atoms, and an aryloxy group containing 5 to 40 ring atoms or heteroaryloxy group containing 5 to 40 ring atoms; wherein $R^2$ forms a monocyclic or polycyclic aliphatic or aromatic ring with a ring bonded to the group.

2. The organic compound according to claim 1, wherein Ar1, Ar2, and Ar3 are independently selected from naphthalene and derivatives thereof.

3. The organic compound according to claim 1, wherein the organic compound has a ΔE(S1-T1) less than or equal to 0.30 eV, and wherein the ΔE(S1-T1) represents a energy level difference between a triplet excited state $T_1$ and a singlet excited state $S_1$ of the organic compound.

4. The organic compound according to claim 1, wherein the organic compound is one selected from compounds represented by the following structures:

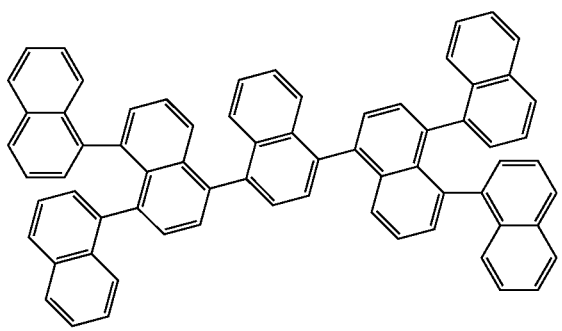

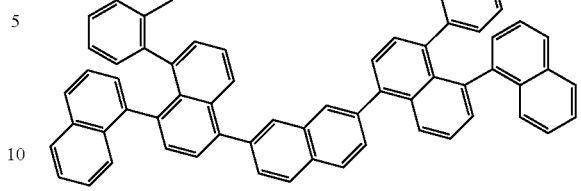

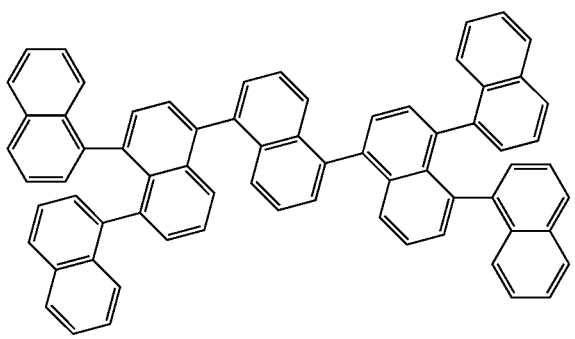

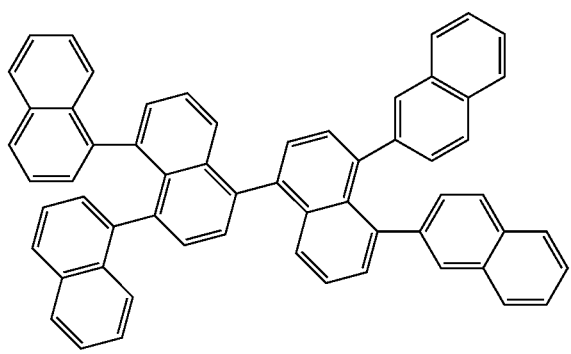

5. An organic mixture, wherein the organic mixture comprises the organic compound according to claim 1 and at least one organic solvent or at least one organic functional material selected from the group consisting of a hole injection material, a hole transport material, a hole blocking material, an electron injection material, an electron transport material, an electron blocking material, an organic host material and a light-emitting material.

6. An organic electronic device, wherein the organic electronic device comprises a functional layer, the functional layer comprising the organic compound according to claim 1.

7. The organic electronic device according to claim 6, wherein the organic electronic device is an organic light emitting diode, an organic photovoltaic cell, an organic light-emitting electrochemical cell, an organic field effect transistor, an organic light-emitting field effect transistor, an organic laser, an organic spintronic device, an organic sensor or an organic plasmon emitting diode.

8. The organic electronic device according to claim 7, wherein the organic electronic device is an organic light-emitting diode, the functional layer is a light-emitting layer, and the light-emitting layer comprises the organic compound.

9. The organic electronic device according to claim 8, wherein the light-emitting layer further comprises a light emitting material and/or a host material.

10. The organic compound according to claim 1, wherein $Ar^1$, $Ar^2$ and $Ar^3$ are independently selected from naphthalene.

11. The organic compound according to claim 10, wherein p is selected from 1, 2 or 3, q is selected from 1, 2, 3 or 4, and t is selected from 2, 3, 4 or 5 in formulas(2)-(7) or (9)-(16).

12. The organic compound according to claim 3, wherein p is selected from 1, 2 or 3, q is selected from 1, 2, 3 or 4, and t is selected from 3, 4 or 5.

* * * * *